US008821365B2

(12) United States Patent
Ozaki et al.

(10) Patent No.: US 8,821,365 B2
(45) Date of Patent: Sep. 2, 2014

(54) ROTATION DRIVE DEVICE AND CENTRIFUGAL PUMP APPARATUS USING THE SAME

(75) Inventors: Takayoshi Ozaki, Iwata (JP); Hiroyuki Yamada, Iwata (JP); Kenichi Suzuki, Iwata (JP); Ken Sugiura, Iwata (JP)

(73) Assignee: Thoratec Corporation, Pleasanton, CA (US)

( * ) Notice: Subject to any disclaimer, the term of this patent is extended or adjusted under 35 U.S.C. 154(b) by 0 days.

(21) Appl. No.: 13/387,637

(22) PCT Filed: Jul. 6, 2010

(86) PCT No.: PCT/JP2010/061439
§ 371 (c)(1),
(2), (4) Date: Jan. 27, 2012

(87) PCT Pub. No.: WO2011/013483
PCT Pub. Date: Feb. 3, 2011

(65) Prior Publication Data
US 2012/0130152 A1    May 24, 2012

(30) Foreign Application Priority Data
Jul. 29, 2009 (JP) .................................. 2009-176498

(51) Int. Cl.
*A61M 1/12* (2006.01)

(52) U.S. Cl.
USPC ........................................... 600/16; 623/3.13

(58) Field of Classification Search
CPC ... A61M 1/101; A61M 2001/1013–2001/1017
USPC ...................... 600/16; 623/3.13, 3.14; 607/16
See application file for complete search history.

(56) References Cited

U.S. PATENT DOCUMENTS

| 1,093,868 A | 4/1914 | Leighty |
| 2,684,035 A | 7/1954 | Kemp |
| 3,510,229 A | 5/1970 | Smith |
| 3,960,468 A | 6/1976 | Boorse et al. |

(Continued)

FOREIGN PATENT DOCUMENTS

| CN | 102239334 A | 11/2011 |
| CN | 102341600 A | 2/2012 |

(Continued)

OTHER PUBLICATIONS

Supplementary European Search Report issued in European Application No. 09/831,788.6, dated Jan. 7, 2013, 7 pages.

(Continued)

*Primary Examiner* — George Evanisko
(74) *Attorney, Agent, or Firm* — Kilpatrick Townsend & Stockton LLP

(57) ABSTRACT

A centrifugal blood pump apparatus includes an impeller provided in a blood chamber, a plurality of permanent magnets provided in the impeller, and a plurality of sets of magnetic materials and coils provided in a motor chamber for driving the impeller to rotate with a diaphragm interposed therebetween. The plurality of permanent magnets are aligned with a gap therebetween in a rotation direction of the impeller. Accordingly, if the weight of the permanent magnets is maintained at a constant value, a magnetic field can be strengthened even with a wide motor gap due to the diaphragm, as compared to an example where there is no gap between the permanent magnets.

10 Claims, 44 Drawing Sheets

(56) References Cited

U.S. PATENT DOCUMENTS

| | | |
|---|---|---|
| 4,149,535 A | 4/1979 | Volder |
| 4,382,199 A | 5/1983 | Isaacson |
| 4,392,836 A | 7/1983 | Sugawara |
| 4,507,048 A | 3/1985 | Belenger et al. |
| 4,540,402 A | 9/1985 | Aigner |
| 4,549,860 A | 10/1985 | Yakich |
| 4,686,982 A | 8/1987 | Nash |
| 4,688,998 A | 8/1987 | Olsen et al. |
| 4,753,221 A | 6/1988 | Kensey et al. |
| 4,769,006 A | 9/1988 | Papantonakos |
| 4,790,843 A | 12/1988 | Carpentier et al. |
| 4,806,080 A | 2/1989 | Mizobuchi et al. |
| 4,817,586 A | 4/1989 | Wampler |
| 4,846,152 A | 7/1989 | Wampler et al. |
| 4,895,557 A | 1/1990 | Moise et al. |
| 4,900,227 A | 2/1990 | Trouplin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,930,997 A | 6/1990 | Bennett |
| 4,944,722 A | 7/1990 | Carriker et al. |
| 4,957,504 A | 9/1990 | Chardack |
| 4,964,864 A | 10/1990 | Summers et al. |
| 4,969,865 A | 11/1990 | Hwang et al. |
| 4,985,014 A | 1/1991 | Orejola |
| 4,995,857 A | 2/1991 | Arnold |
| 5,021,048 A | 6/1991 | Buckholtz |
| 5,078,741 A | 1/1992 | Bramm et al. |
| 5,092,844 A | 3/1992 | Schwartz et al. |
| 5,092,879 A | 3/1992 | Jarvik |
| 5,106,263 A | 4/1992 | Irie |
| 5,106,273 A | 4/1992 | Lemarquand et al. |
| 5,106,372 A | 4/1992 | Ranford |
| 5,112,349 A | 5/1992 | Summers et al. |
| 5,129,883 A | 7/1992 | Black |
| 5,145,333 A | 9/1992 | Smith |
| 5,147,186 A | 9/1992 | Buckholtz |
| 5,190,528 A | 3/1993 | Fonger et al. |
| 5,201,679 A | 4/1993 | Velte et al. |
| 5,211,546 A | 5/1993 | Isaacson et al. |
| 5,275,580 A | 1/1994 | Yamazaki |
| 5,290,227 A | 3/1994 | Pasque |
| 5,300,112 A | 4/1994 | Barr |
| 5,306,295 A | 4/1994 | Kolff et al. |
| 5,312,341 A | 5/1994 | Turi |
| 5,332,374 A * | 7/1994 | Kricker et al. ............... 417/420 |
| 5,346,458 A | 9/1994 | Afield |
| 5,354,331 A | 10/1994 | Schachar |
| 5,360,445 A | 11/1994 | Goldowsky |
| 5,370,509 A | 12/1994 | Golding et al. |
| 5,376,114 A | 12/1994 | Jarvik |
| 5,385,581 A | 1/1995 | Bramm et al. |
| 5,405,383 A | 4/1995 | Barr |
| 5,449,342 A | 9/1995 | Hirose et al. |
| 5,504,978 A | 4/1996 | Meyer, III |
| 5,507,629 A | 4/1996 | Jarvik |
| 5,533,957 A | 7/1996 | Aldea |
| 5,569,111 A | 10/1996 | Cho et al. |
| 5,575,630 A | 11/1996 | Nakazawa et al. |
| 5,595,762 A | 1/1997 | Derrieu et al. |
| 5,611,679 A | 3/1997 | Ghosh et al. |
| 5,613,935 A | 3/1997 | Jarvik |
| 5,643,226 A | 7/1997 | Cosgrove et al. |
| 5,678,306 A | 10/1997 | Bozeman, Jr. et al. |
| 5,692,882 A | 12/1997 | Bozeman, Jr. et al. |
| 5,695,471 A | 12/1997 | Wampler |
| 5,725,357 A | 3/1998 | Nakazeki et al. |
| 5,738,649 A | 4/1998 | Macoviak |
| 5,746,575 A | 5/1998 | Westphal et al. |
| 5,746,709 A | 5/1998 | Rom et al. |
| 5,749,855 A | 5/1998 | Reitan |
| 5,755,784 A | 5/1998 | Jarvik |
| 5,776,111 A | 7/1998 | Tesio |
| 5,800,559 A | 9/1998 | Higham et al. |
| 5,807,311 A | 9/1998 | Palestrant |
| 5,814,011 A | 9/1998 | Corace |
| 5,824,069 A | 10/1998 | Lemole |
| 5,851,174 A | 12/1998 | Jarvik et al. |
| 5,853,394 A | 12/1998 | Tolkoff et al. |
| 5,868,702 A | 2/1999 | Stevens et al. |
| 5,868,703 A | 2/1999 | Bertolero et al. |
| 5,890,883 A | 4/1999 | Golding et al. |
| 5,911,685 A | 6/1999 | Siess et al. |
| 5,921,913 A | 7/1999 | Siess |
| 5,924,848 A | 7/1999 | Izraelev |
| 5,924,975 A | 7/1999 | Goldowsky |
| 5,938,412 A | 8/1999 | Izraelev |
| 5,941,813 A | 8/1999 | Sievers et al. |
| 5,947,703 A | 9/1999 | Nojiri et al. |
| 5,951,263 A | 9/1999 | Taylor et al. |
| 5,964,694 A | 10/1999 | Siess et al. |
| 6,004,269 A | 12/1999 | Crowley et al. |
| 6,007,479 A | 12/1999 | Rottenberg et al. |
| 6,042,347 A | 3/2000 | Scholl et al. |
| 6,058,593 A | 5/2000 | Siess |
| 6,066,086 A | 5/2000 | Antaki et al. |
| 6,071,093 A | 6/2000 | Hart |
| 6,074,180 A | 6/2000 | Khanwilkar et al. |
| 6,080,133 A | 6/2000 | Wampler |
| 6,083,260 A | 7/2000 | Aboul-Hosn |
| 6,086,527 A | 7/2000 | Talpade |
| 6,123,659 A | 9/2000 | leBlanc et al. |
| 6,123,726 A | 9/2000 | Mori et al. |
| 6,139,487 A | 10/2000 | Siess |
| 6,142,752 A | 11/2000 | Akamatsu et al. |
| 6,143,025 A | 11/2000 | Stobie et al. |
| 6,146,325 A | 11/2000 | Lewis et al. |
| 6,149,683 A | 11/2000 | Lancisi et al. |
| 6,158,984 A | 12/2000 | Cao et al. |
| 6,176,822 B1 | 1/2001 | Nix et al. |
| 6,176,848 B1 | 1/2001 | Rau et al. |
| 6,190,304 B1 | 2/2001 | Downey et al. |
| 6,200,260 B1 | 3/2001 | Bolling |
| 6,206,659 B1 | 3/2001 | Izraelev |
| 6,234,772 B1 | 5/2001 | Wampler et al. |
| 6,234,998 B1 | 5/2001 | Wampler |
| 6,245,007 B1 | 6/2001 | Bedingham et al. |
| 6,247,892 B1 | 6/2001 | Kazatchkov et al. |
| 6,254,359 B1 | 7/2001 | Aber |
| 6,264,635 B1 | 7/2001 | Wampler et al. |
| 6,293,901 B1 * | 9/2001 | Prem ............................. 600/17 |
| 6,295,877 B1 | 10/2001 | Aboul-Hosn et al. |
| 6,319,231 B1 | 11/2001 | Andrulitis |
| 6,375,607 B1 | 4/2002 | Prem |
| 6,387,037 B1 | 5/2002 | Bolling et al. |
| 6,422,990 B1 | 7/2002 | Prem |
| 6,425,007 B1 | 7/2002 | Messinger |
| 6,428,464 B1 | 8/2002 | Bolling |
| 6,439,845 B1 | 8/2002 | Veres |
| 6,447,266 B2 | 9/2002 | Antaki et al. |
| 6,447,441 B1 | 9/2002 | Yu et al. |
| 6,458,163 B1 | 10/2002 | Slemker et al. |
| 6,508,777 B1 | 1/2003 | Macoviak et al. |
| 6,508,787 B2 | 1/2003 | Erbel et al. |
| 6,517,315 B2 | 2/2003 | Belady |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | deBlanc et al. |
| 6,610,004 B2 | 8/2003 | Viole et al. |
| 6,641,558 B1 | 11/2003 | Aboul-Hosn et al. |
| 6,688,861 B2 | 2/2004 | Wampler |
| 6,692,318 B2 | 2/2004 | McBride |
| 6,709,418 B1 | 3/2004 | Aboul-Hosn et al. |
| 6,716,189 B1 | 4/2004 | Jarvik et al. |
| 6,732,501 B2 | 5/2004 | Yu et al. |
| 6,749,598 B1 | 6/2004 | Keren et al. |
| 6,776,578 B2 | 8/2004 | Belady |
| 6,790,171 B1 | 9/2004 | Griindeman et al. |
| 6,794,789 B2 | 9/2004 | Siess et al. |
| 6,808,371 B2 | 10/2004 | Niwatsukino et al. |
| 6,817,836 B2 | 11/2004 | Nose et al. |
| 6,860,713 B2 | 3/2005 | Hoover |

(56) References Cited

U.S. PATENT DOCUMENTS

| | | |
|---|---|---|
| 6,926,662 B1 | 8/2005 | Aboul-Hosn et al. |
| 6,935,344 B1 | 8/2005 | Aboul-Hosn et al. |
| 6,942,672 B2 | 9/2005 | Heilman et al. |
| 6,949,066 B2 | 9/2005 | Beamson et al. |
| 6,966,748 B2 | 11/2005 | Woodard et al. |
| 6,974,436 B1 | 12/2005 | Aboul-Hosn et al. |
| 7,010,954 B2 | 3/2006 | Siess et al. |
| 7,011,620 B1 | 3/2006 | Siess |
| 7,022,100 B1 | 4/2006 | Aboul-Hosn et al. |
| 7,027,875 B2 | 4/2006 | Siess et al. |
| 7,048,681 B2 | 5/2006 | Tsubouchi et al. |
| 7,122,019 B1 | 10/2006 | Kesten et al. |
| 7,156,802 B2 | 1/2007 | Woodard et al. |
| 7,172,551 B2 | 2/2007 | Leasure |
| 7,175,588 B2 | 2/2007 | Morello |
| 7,241,257 B1 | 7/2007 | Ainsworth et al. |
| 7,329,236 B2 | 2/2008 | Kesten et al. |
| 7,331,921 B2 | 2/2008 | Viole et al. |
| 7,335,192 B2 | 2/2008 | Keren et al. |
| 7,393,181 B2 | 7/2008 | McBride et al. |
| 7,476,077 B2 | 1/2009 | Woodard et al. |
| 7,491,163 B2 | 2/2009 | Viole et al. |
| 7,731,675 B2 | 6/2010 | Aboul-Hosn et al. |
| 7,841,976 B2 | 11/2010 | McBride et al. |
| 7,888,242 B2 | 2/2011 | Tanaka et al. |
| 8,283,829 B2 * | 10/2012 | Yamamoto et al. ...... 310/156.32 |
| 8,366,381 B2 | 2/2013 | Woodard et al. |
| 8,403,823 B2 | 3/2013 | Yu et al. |
| 8,512,012 B2 | 8/2013 | Akdis et al. |
| 2002/0058994 A1 | 5/2002 | Hill et al. |
| 2002/0095210 A1 | 7/2002 | Finnegan et al. |
| 2003/0023302 A1 | 1/2003 | Moe et al. |
| 2004/0007515 A1 | 1/2004 | Geyer |
| 2004/0015232 A1 | 1/2004 | Shu et al. |
| 2004/0024285 A1 | 2/2004 | Muckter |
| 2004/0030381 A1 | 2/2004 | Shu |
| 2004/0171905 A1 | 9/2004 | Yu et al. |
| 2004/0210305 A1 | 10/2004 | Shu et al. |
| 2005/0287022 A1 * | 12/2005 | Yaegashi et al. ............... 417/420 |
| 2006/0024182 A1 | 2/2006 | Akdis et al. |
| 2006/0055274 A1 | 3/2006 | Kim |
| 2007/0095648 A1 | 5/2007 | May et al. |
| 2007/0134993 A1 | 6/2007 | Tamez et al. |
| 2007/0213690 A1 | 9/2007 | Phillips et al. |
| 2007/0297923 A1 | 12/2007 | Tada |
| 2008/0124231 A1 | 5/2008 | Yaegashi |
| 2009/0171136 A1 | 7/2009 | Shambaugh, Jr. |
| 2011/0118766 A1 | 5/2011 | Reichenbach et al. |
| 2011/0118829 A1 | 5/2011 | Hoarau et al. |
| 2011/0118833 A1 | 5/2011 | Reichenbach et al. |
| 2011/0243759 A1 | 10/2011 | Ozaki et al. |
| 2011/0318203 A1 | 12/2011 | Ozaki et al. |
| 2012/0130152 A1 | 5/2012 | Ozaki et al. |
| 2013/0178694 A1 | 7/2013 | Jeffery et al. |

FOREIGN PATENT DOCUMENTS

| | | |
|---|---|---|
| EP | 1113117 A2 | 7/2001 |
| EP | 1495773 A2 | 1/2005 |
| EP | 1495773 A3 | 11/2006 |
| EP | 1495773 B1 | 2/2009 |
| EP | 2372160 A1 | 10/2011 |
| EP | 2405140 A1 | 1/2012 |
| EP | 2461465 A1 | 6/2012 |
| JP | 04-091396 | 3/1992 |
| JP | 4-091396 | 3/1992 |
| JP | 05-021197 U | 3/1993 |
| JP | 6-53790 | 7/1994 |
| JP | 06-053790 U | 7/1994 |
| JP | 2001-309628 | 11/2001 |
| JP | 2004-209240 | 7/2004 |
| JP | 2006-167173 | 6/2006 |
| JP | 2007-043821 | 2/2007 |
| JP | 2007-089972 A | 4/2007 |
| JP | 2007-089974 | 4/2007 |
| JP | 2007-215292 | 8/2007 |
| JP | 2007-247489 | 9/2007 |
| JP | 2008-104278 | 5/2008 |
| JP | 2008-132131 | 6/2008 |
| WO | 97-42413 A1 | 11/1997 |
| WO | 2005-034312 A2 | 4/2005 |
| WO | 2011-013483 A1 | 2/2011 |

OTHER PUBLICATIONS

Supplemental European Search Report issued in European Patent Application No. 10/748,702.7 dated Apr. 2, 2013, 7 pages.

Asama, et al., "Suspension Performance of a Two-Axis Actively Regulated Consequent-Pole Bearingless Motor," IEEE Transactions on Energy Conversion, vol. 28, No. 4, Dec. 2013, 8 pages.

Terumo Heart, Inc., "Handled With Care—Significantly Reduce the Risk of Cell Damage," Terumo brochure, Apr. 2010, 2 pages.

Yamazaki, et al., "Development of a Miniature Intraventricular Axial Flow Blood Pump," ASAIO Journal, 1993, 7 pages.

* cited by examiner

FIG.13
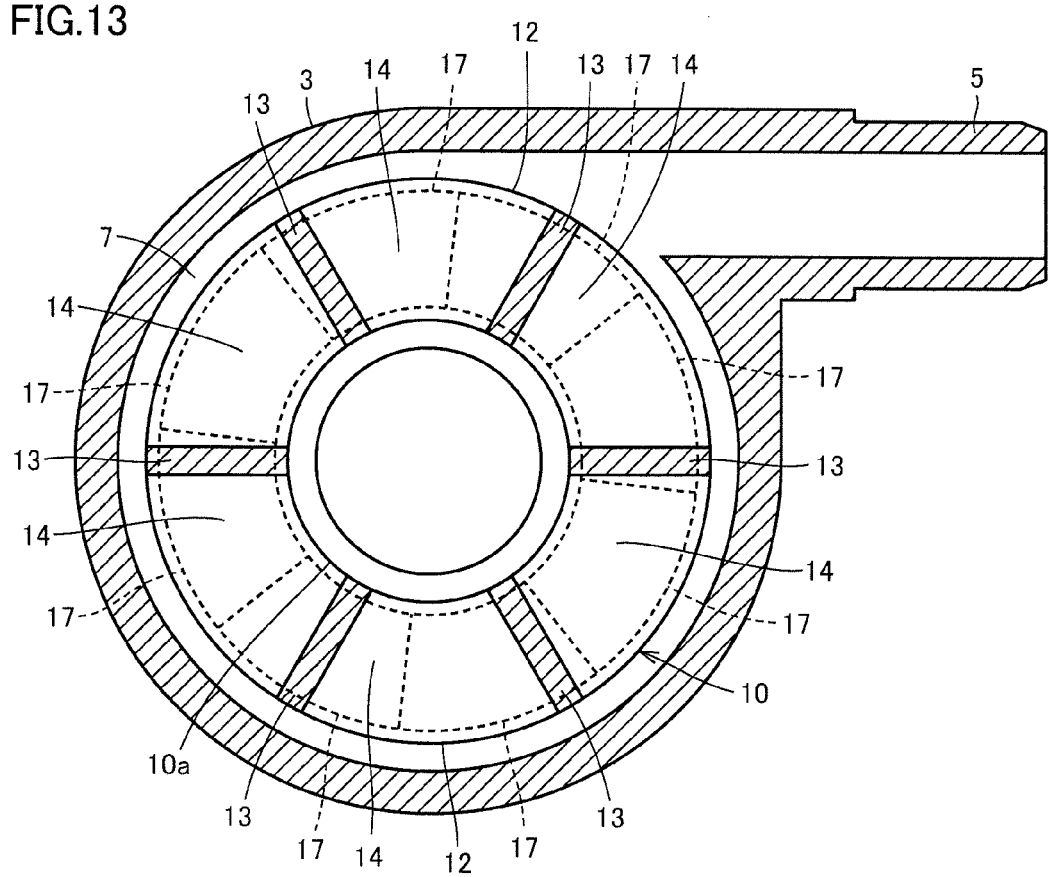
FIG.14
(a) PRESENT INVENTION
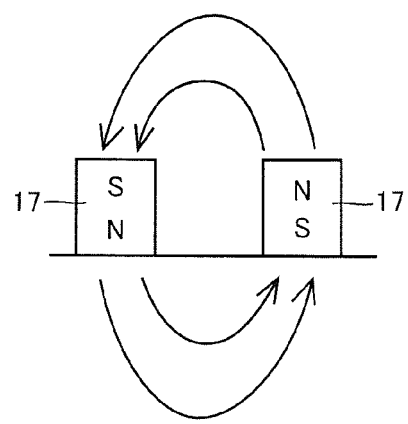
(b) COMPARATIVE EXAMPLE
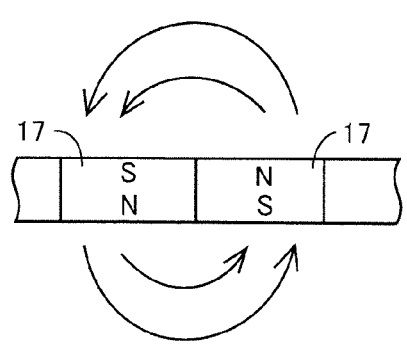

AREA RATIO OF GAP TO PERMANENT MAGNET 17

AREA RATIO OF PERMANENT MAGNET 31
TO PERMANENT MAGNET 17

FIG.39
(a)
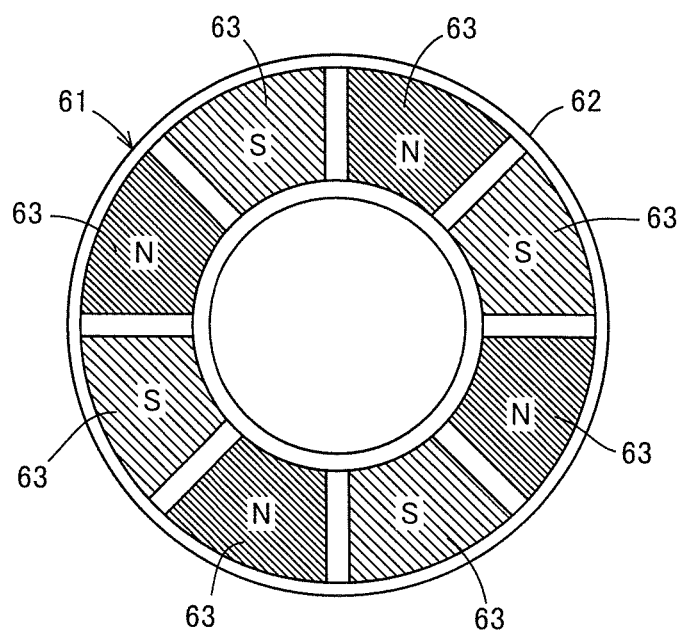
(b)
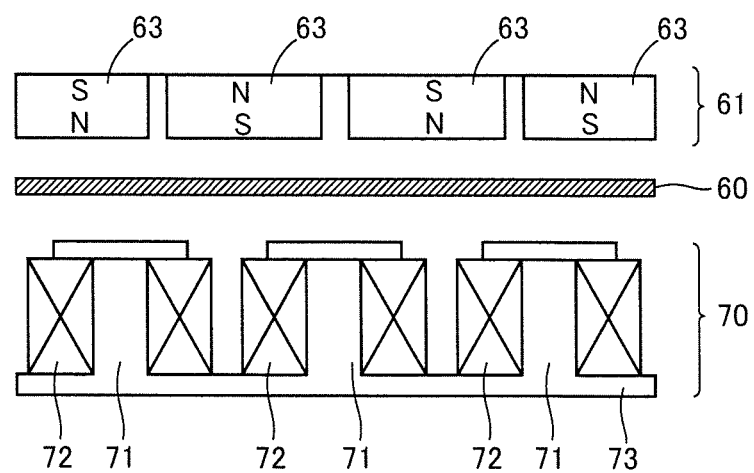

FIG.40
(a)
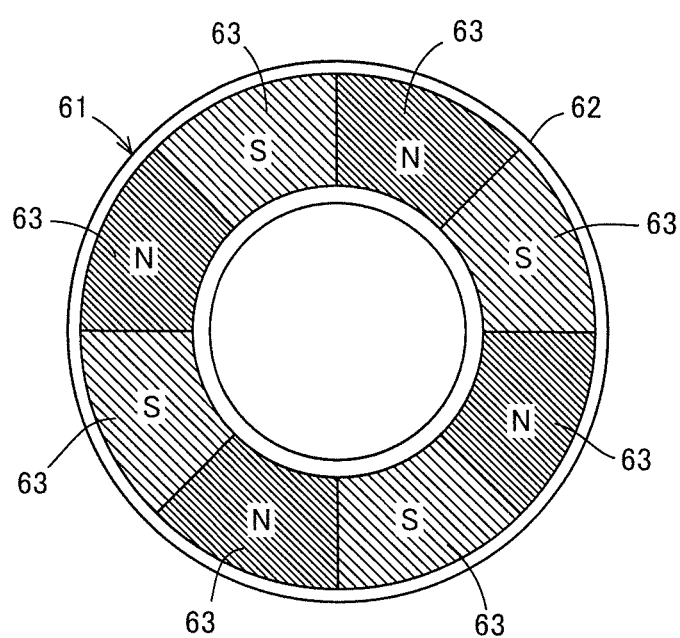
(b)
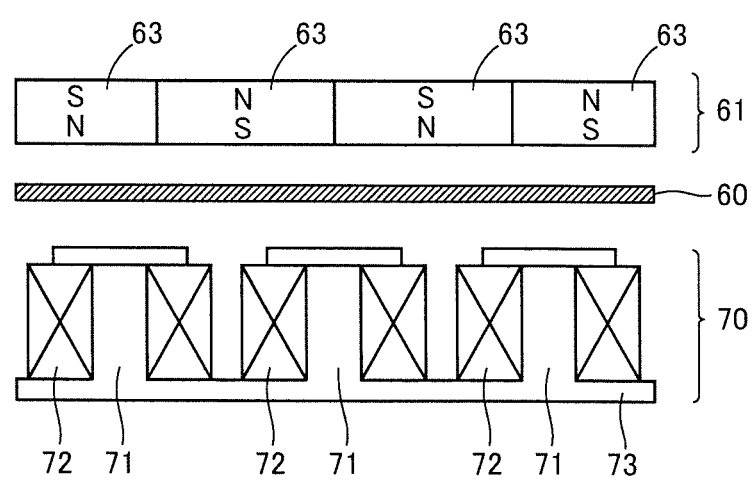

FIG.43
(a)
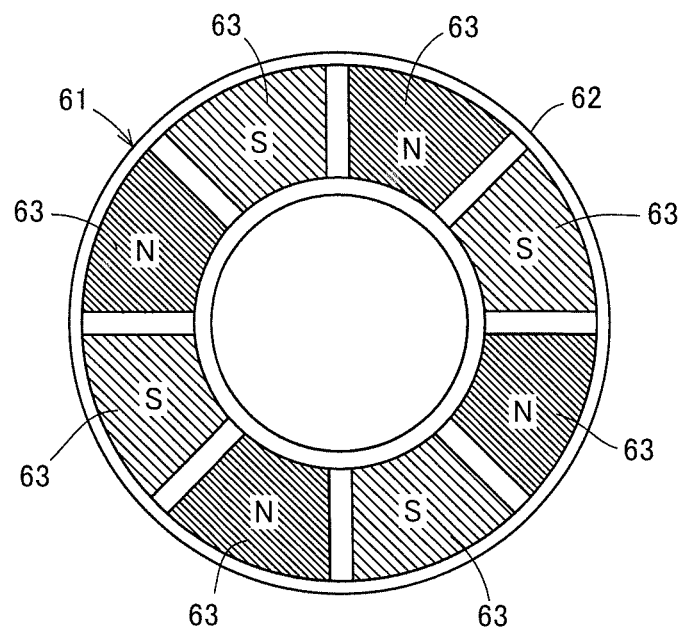
(b)
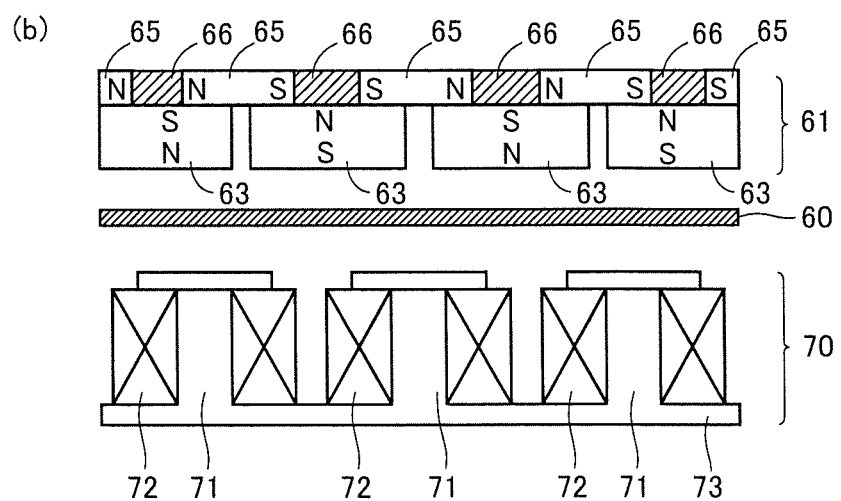

FIG.44
(a)
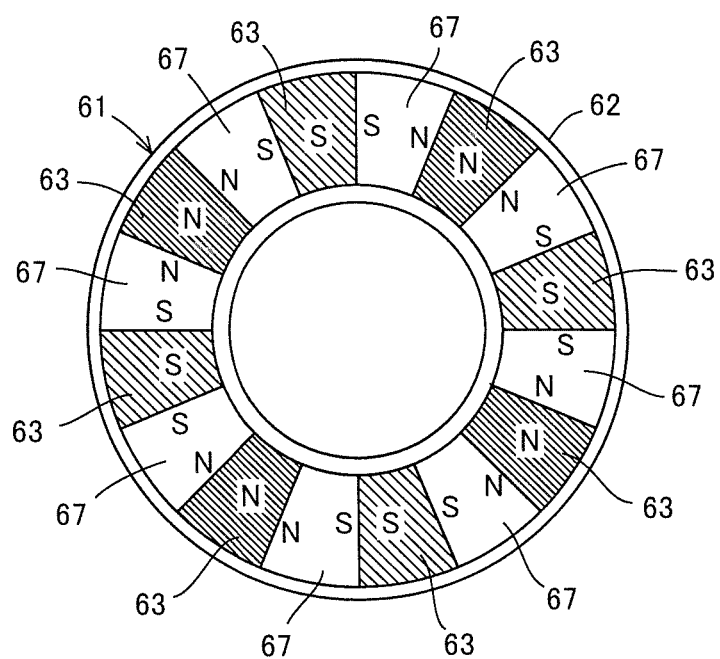
(b)
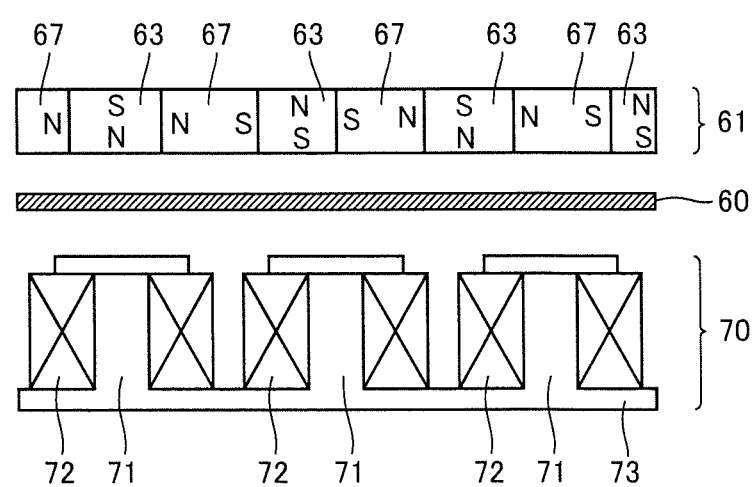

ROTATION DRIVE DEVICE AND CENTRIFUGAL PUMP APPARATUS USING THE SAME

RELATED APPLICATIONS

This application is the U.S. National Phase under 35 U.S.C. §371 of International Application No. PCT/JP2010/061439, filed on Jul. 6, 2010, which in turn claims the benefit of Japanese Application No. 2009-176498, filed on Jul. 29, 2009, the disclosures of which Applications are incorporated by reference herein.

TECHNICAL FIELD

The present invention relates to a rotation drive device and a centrifugal pump apparatus using the same, and more particularly to a rotation drive device for transmitting a driving force with a diaphragm interposed therebetween and a centrifugal pump apparatus using the same.

BACKGROUND ART

In recent years, canned motors having a structure including a motor drive chamber and a rotor chamber separated from each other by a diaphragm have been widely used. Such motor is used for a pump for transporting pure water in a semiconductor manufacturing line used in an environment that avoids dust, and a pump for transporting a biological solution, for example. Pumps for transporting a biological solution include a centrifugal blood pump apparatus using a direct drive motor for directly transmitting torque to an impeller in a blood chamber. This centrifugal blood pump apparatus can eliminate physical contact between the blood chamber and the outside to prevent invasion of bacteria and the like into blood, and is thus used as an artificial heart. Since an artificial heart is driven by electric power from a battery, enhancement of motor efficiency is critical.

A centrifugal blood pump in Japanese Patent Laying-Open No. 2004-209240 (PTL 1) includes a housing having first to third chambers partitioned from one another by first and second diaphragms, an impeller rotatably provided in the second chamber (blood chamber), a magnetic material provided in one surface of the impeller, an electromagnet provided in the first chamber to face the one surface of the impeller, a permanent magnet provided in the other surface of the impeller, a rotor and a motor provided in the third chamber, and a permanent magnet provided in the rotor to face the other surface of the impeller. Grooves for hydrodynamic bearing are formed in a surface of the second diaphragm facing the other surface of the impeller. Due to an attractive force acting on the one surface of the impeller from the electromagnet, an attractive force acting on the other surface of the impeller from the permanent magnet in the rotor, and a hydrodynamic bearing effect of the grooves for hydrodynamic bearing, the impeller moves away from an inner surface of the second chamber, and rotates without contacting.

A centrifugal blood pump in Japanese Patent Laying-Open No. 2006-167173 (PTL 2) includes a housing having first to third chambers partitioned from one another by first and second diaphragms, an impeller rotatably provided in the second chamber (blood chamber), a magnetic material provided in one surface of the impeller, a first permanent magnet provided in the first chamber to face the one surface of the impeller, a second permanent magnet provided in the other surface of the impeller, a rotor and a motor provided in the third chamber, and a third permanent magnet provided in the rotor to face the other surface of the impeller. First grooves for hydrodynamic bearing are formed in a surface of the first diaphragm facing the one surface of the impeller, and second grooves for hydrodynamic bearing are formed in a surface of the second diaphragm facing the other surface of the impeller. Due to an attractive force acting on the one surface of the impeller from the first permanent magnet, an attractive force acting on the other surface of the impeller from the third permanent magnet in the rotor, and a hydrodynamic bearing effect of the first and second grooves for hydrodynamic bearing, the impeller moves away from an inner surface of the second chamber, and rotates without contacting.

A turbo-type pump in FIGS. 8 and 9 of Japanese Patent Laying-Open No. 4-91396 (PTL 3) includes a housing, an impeller rotatably provided in the housing, a first permanent magnet provided in one surface of the impeller, a rotor provided outside of the housing, a second permanent magnet provided in the rotor to face the one surface of the impeller, a third permanent magnet provided in the other surface of the impeller, and a magnetic material provided in the housing to face the other surface of the impeller. First grooves for hydrodynamic bearing are formed in the one surface of the impeller, and second grooves for hydrodynamic bearing are formed in the other surface of the impeller. Due to an attractive force acting on the one surface of the impeller from the second permanent magnet in the rotor, an attractive force acting on the other surface of the impeller from the magnetic material in the housing, and a hydrodynamic bearing effect of the first and second grooves for hydrodynamic bearing, the impeller moves away from an inner surface of the housing, and rotates without contacting.

A clean pump in Japanese Utility Model Laying-Open No. 6-53790 (PTL 4) includes a casing, an impeller rotatably provided in the casing, a first permanent magnet provided in one surface of the impeller, a rotor provided outside of the casing, a second permanent magnet provided in the rotor to face the one surface of the impeller, a magnetic material provided in the other surface of the impeller, and an electromagnet provided outside of the housing to face the other surface of the impeller. Grooves for hydrodynamic bearing are formed in the one surface of the impeller. The electromagnet is operated when a rotation speed of the impeller is lower than a predetermined rotation speed, and power supply to the electromagnet is stopped when the rotation speed of the impeller becomes higher than the predetermined rotation speed. Due to an attractive force acting on the one surface of the impeller from the second permanent magnet in the rotor, and a hydrodynamic bearing effect of the grooves for hydrodynamic bearing, the impeller moves away from an inner surface of the housing, and rotates without contacting.

CITATION LIST

Patent Literature

PTL 1: Japanese Patent Laying-Open No. 2004-209240
PTL 2: Japanese Patent Laying-Open No. 2006-167173
PTL 3: Japanese Patent Laying-Open No. 4-91396
PTL 4: Japanese Utility Model Laying-Open No. 6-53790

SUMMARY OF INVENTION

Technical Problem

Unfortunately, in a canned motor having a diaphragm provided between a stator and a rotor, there is a large gap between the stator and the rotor, resulting in difficulty in increasing torque and enhancing efficiency. Particularly, it is difficult to enhance efficiency of a small motor due to its low degree of design flexibility by dimensional restrictions and the like, and its susceptibility to local magnetic saturation. Nevertheless, even with a wide gap, if a field magnetic flux of a permanent magnet in the rotor can be efficiently passed through the stator, torque can be increased by suppressing increase in attractive force between the stator and the rotor and magnetic flux saturation of a motor yoke.

The pumps in PTLs 1 to 4 described above share the feature of axially supporting the impeller by the grooves for hydrodynamic bearing formed in a portion where the impeller and the housing face each other, and radially supporting the impeller by the attractive force between the permanent magnet provided in the impeller and the permanent magnet provided outside of the housing.

Supporting rigidity of grooves for hydrodynamic bearing is proportionate to a rotation speed of an impeller. Thus, in order for an impeller to stably rotate without contacting a housing even when disturbance is applied to a pump, axial rigidity for the impeller needs to be enhanced by increasing a normal rotation speed range of the pump. In the pumps of PTLs 1 to 4 described above, however, the impeller is radially supported by utilizing the attractive force of the permanent magnets, and so the supporting rigidity is low, resulting in inability to rotate the impeller at high speed.

One way to increase the radial rigidity is to increase the attractive force between the permanent magnet in the impeller and the permanent magnet or a stator provided outside of the housing. As the attractive force is increased, however, a negative axial rigidity value of the impeller increases (namely, as the impeller moves axially, the attractive force increases correspondingly). Thus, supporting function on the impeller by hydrodynamic pressure and the attractive force acting between the impeller and the housing increase, resulting in difficulty in smoothly driving the impeller to rotate. Furthermore, if the negative axial rigidity value of the impeller is higher than positive rigidity resulting from hydrodynamic pressure, stable rotation cannot be obtained. If radial support is provided by a passive magnetic bearing with a permanent magnet, radial rigidity is determined by a negative axial rigidity value. It is thus difficult to improve the radial rigidity under conditions for realizing stable rotation, and the mass of the impeller must not be increased in order for the impeller to rotate without contacting the housing.

In particular, when an impeller is rotated by magnetic interaction between an outside motor coil and a permanent magnet provided in the impeller as shown in FIG. 39 of PTL 2, starting torque is small as compared to an example where an impeller is driven to rotate by magnetic coupling between permanent magnets as shown in FIG. 3 of PTL 2, resulting in difficulty in smoothly driving the impeller to rotate. This is because this centrifugal blood pump has a canned motor structure in which the impeller rotatably provided in the second chamber (blood chamber) is rotated by the motor with respect to the housing including the first to third chambers partitioned from one another by the first and second diaphragms, and thus has a wide motor gap. In order to increase motor torque without increasing the mass of the impeller and without increasing a negative axial rigidity value with respect to this wide gap, a field magnetic flux of the motor needs to reach further away.

To address the small starting torque, PTL 2 proposes a method of providing an electromagnet for biasing the impeller toward a predetermined direction, and a magnetic force adjustment coil for varying a magnetic force of the permanent magnets, and operating them when activating the impeller to rotate, to smoothly activate the impeller. However, this approach requires new dedicated members such as the electromagnet and the coil, which increases a pump size, and the increased number of components results in lower reliability. These are serious problems for a blood pump for use in an artificial heart or the like.

Therefore, a main object of the present invention is to provide a small rotation drive device capable of generating large torque and achieving high energy efficiency, and a centrifugal pump apparatus using the same.

Solution to Problem

A rotation drive device according to the present invention includes a housing having first and second chambers partitioned from each other by a diaphragm, a rotor rotatably provided in the first chamber along the diaphragm, and drive means provided in the second chamber for driving the rotor to rotate with the diaphragm interposed therebetween. This rotation drive device includes a plurality of first permanent magnets provided in the rotor and aligned with a gap therebetween in a rotation direction of the rotor. Each of the first permanent magnets is magnetized in a direction orthogonal to the rotation direction of the rotor. Every two adjacent ones of the first permanent magnets have magnetic polarities different from each other. The drive means includes a plurality of first magnetic materials arranged to face the plurality of first permanent magnets, and a plurality of coils wound around the plurality of first magnetic materials, respectively, for generating a rotating magnetic field. Accordingly, by providing the gaps between the first permanent magnets while maintaining the weight of the first permanent magnets at a constant value, magnetic flux density between the first permanent magnets can be increased to increase a magnetic coupling force between the rotor and the drive means. As a result, large torque can be obtained while maintaining small device dimensions.

Preferably, the rotation drive device further includes a second magnetic material provided in the rotor, arranged on a side of the plurality of first permanent magnets opposite to a side closer to the diaphragm, and magnetically coupled to the plurality of first permanent magnets. In this case, the magnetic coupling force between the rotor and the drive means can be increased to obtain larger torque. Further, copper loss that occurs in the coils can be reduced, thereby enhancing energy efficiency in driving the rotor to rotate.

Preferably, the rotation drive device further includes a plurality of second permanent magnets provided in the rotor and magnetically coupled to the plurality of first permanent magnets, in which each of the second permanent magnets is provided correspondingly to a gap between every two adjacent ones of the first permanent magnets, and is magnetized in the rotation direction of the rotor. In this case, the magnetic coupling force between the rotor and the drive means can be increased to obtain larger torque. Further, copper loss that occurs in the coils can be reduced, thereby enhancing energy efficiency in driving the rotor to rotate.

Preferably, each of the second permanent magnets is arranged to cover a corresponding gap from a side opposite to the diaphragm, and each magnetic polarity of each of the second permanent magnets is identical to an adjacent magnetic polarity of the second permanent magnet, and is different from a corresponding magnetic polarity of the first permanent magnet.

Preferably, the rotation drive device further includes a plurality of second magnetic materials provided in the rotor and inserted in the plurality of gaps between the plurality of second permanent magnets, respectively. In this case, the magnetic coupling force between the rotor and the drive means can be increased to obtain larger torque. Further, copper loss that occurs in the coils can be reduced, thereby enhancing energy efficiency in driving the rotor to rotate.

Preferably, each of the second permanent magnets is inserted in a corresponding gap. Each of the second permanent magnets has a first magnetic polarity oriented to one of the two adjacent first permanent magnets having the first magnetic polarity oriented to the diaphragm. Each of the second permanent magnets has a second magnetic polarity oriented to the other of the two adjacent first permanent magnets having the second magnetic polarity oriented to the diaphragm. In this case, the magnetic coupling force between the rotor and the drive means for generating torque can be increased while reducing an attractive force between the rotor and the drive means, to obtain larger torque. Further, copper loss that occurs in the coils can be reduced, thereby enhancing energy efficiency in driving the rotor to rotate. Furthermore, the dimensions of the magnets can be minimized to reduce the dimensions of the device.

Preferably, a ratio of a surface area of each of the second permanent magnets facing the diaphragm to a surface area of each of the first permanent magnets facing the diaphragm is set to be ½ or more and 2 or less. In this case, the magnetic coupling force between the rotor and the drive means for generating torque can be maximized while reducing an attractive force between the rotor and the drive means.

Preferably, the diaphragm is formed in a cylindrical shape, and the rotor and the drive means are arranged with a gap therebetween in a radial direction of the rotor. In this case, the rotation drive device is a radial gap type motor.

Preferably, the diaphragm is formed in a plane shape, and the rotor and the drive means are arranged with a gap therebetween in a direction in which a rotation central axis of the rotor extends. In this case, the rotation drive device is an axial gap type motor.

A centrifugal pump apparatus according to the present invention includes the rotation drive device described above. The rotor is an impeller for delivering liquid by a centrifugal force during rotation.

Another centrifugal pump apparatus according to the present invention includes a housing having first and second chambers partitioned from each other by a diaphragm, an impeller rotatably provided in the first chamber along the diaphragm for delivering liquid by a centrifugal force during rotation, and drive means provided in the second chamber for driving the impeller to rotate with the diaphragm interposed therebetween. This centrifugal pump apparatus includes a first magnetic material provided in one surface of the impeller, a second magnetic material provided in an inner wall of the first chamber facing the one surface of the impeller, for attracting the first magnetic material, and a plurality of first permanent magnets provided in the other surface of the impeller and aligned with a gap therebetween in a rotation direction of the impeller. Each of the first permanent magnets is magnetized in a direction in which a rotation central axis of the impeller extends. Every two adjacent ones of the first permanent magnets have magnetic polarities different from each other. The drive means includes a plurality of third magnetic materials arranged to face the plurality of first permanent magnets, and a plurality of coils provided correspondingly to the plurality of third magnetic materials and wound around corresponding ones of the third magnetic materials, respectively, for generating a rotating magnetic field. During rotation of the impeller, a first attractive force between the first and second magnetic materials and a second attractive force between the plurality of first permanent magnets and the plurality of third magnetic materials are balanced with each other substantially in a center of a movable range of the impeller in the first chamber. First grooves for hydrodynamic bearing are formed in the one surface of the impeller or in the inner wall of the first chamber facing the one surface, and second grooves for hydrodynamic bearing are formed in the other surface of the impeller or in the diaphragm facing the other surface.

Preferably, the liquid is blood, and the centrifugal pump apparatus is used for circulating the blood. In this case, the impeller is smoothly activated to rotate to secure a distance between the impeller and the housing, thereby preventing occurrence of hemolysis.

Advantageous Effects of Invention

As described above, according to the present invention, large torque for driving a rotor or an impeller to rotate can be generated while maintaining small device dimensions. In addition, energy efficiency in driving the rotor or the impeller to rotate can be enhanced. Furthermore, hemolysis can be avoided when circulating blood.

BRIEF DESCRIPTION OF DRAWINGS

FIG. 13 is a cross-sectional view showing a comparative example of the first embodiment.

FIG. 14 explains the effect of the first embodiment.

FIG. 39 shows a structure of an axial gap type motor according to a third embodiment of the present invention.

FIG. 40 shows a comparative example of the third embodiment.

FIG. 43 shows yet another modification of the third embodiment.

FIG. 44 shows yet another modification of the third embodiment.

DESCRIPTION OF EMBODIMENTS

[First Embodiment]

Figure 1:
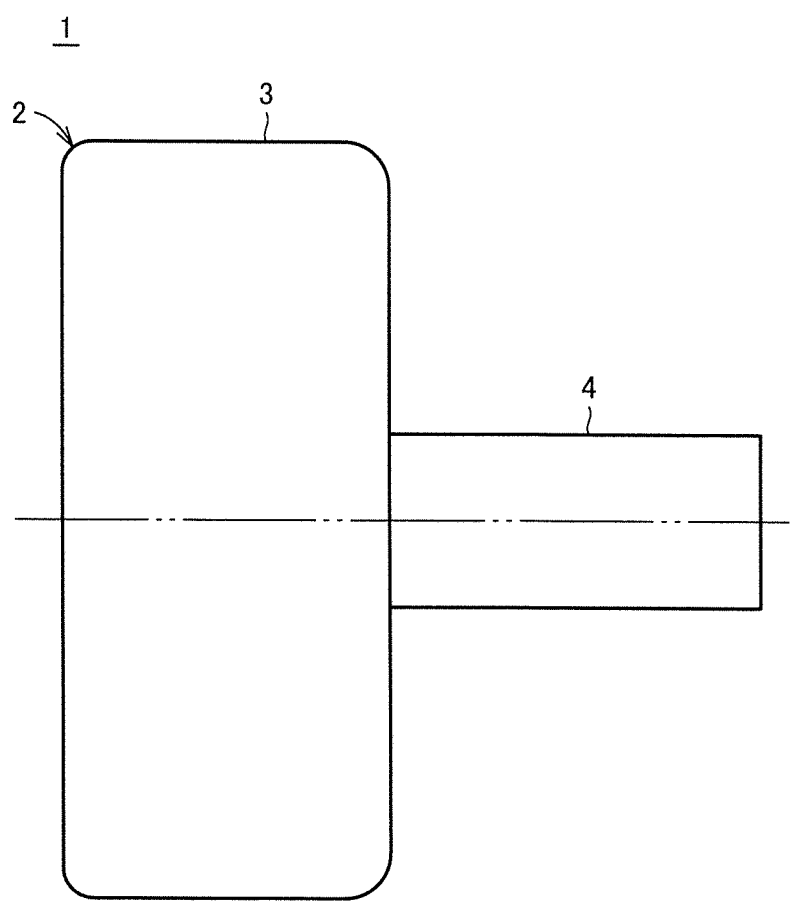
FIG. 1 is a front view showing the appearance of a pump unit of a centrifugal blood pump apparatus according to a first embodiment of the present invention.
Figure 2:
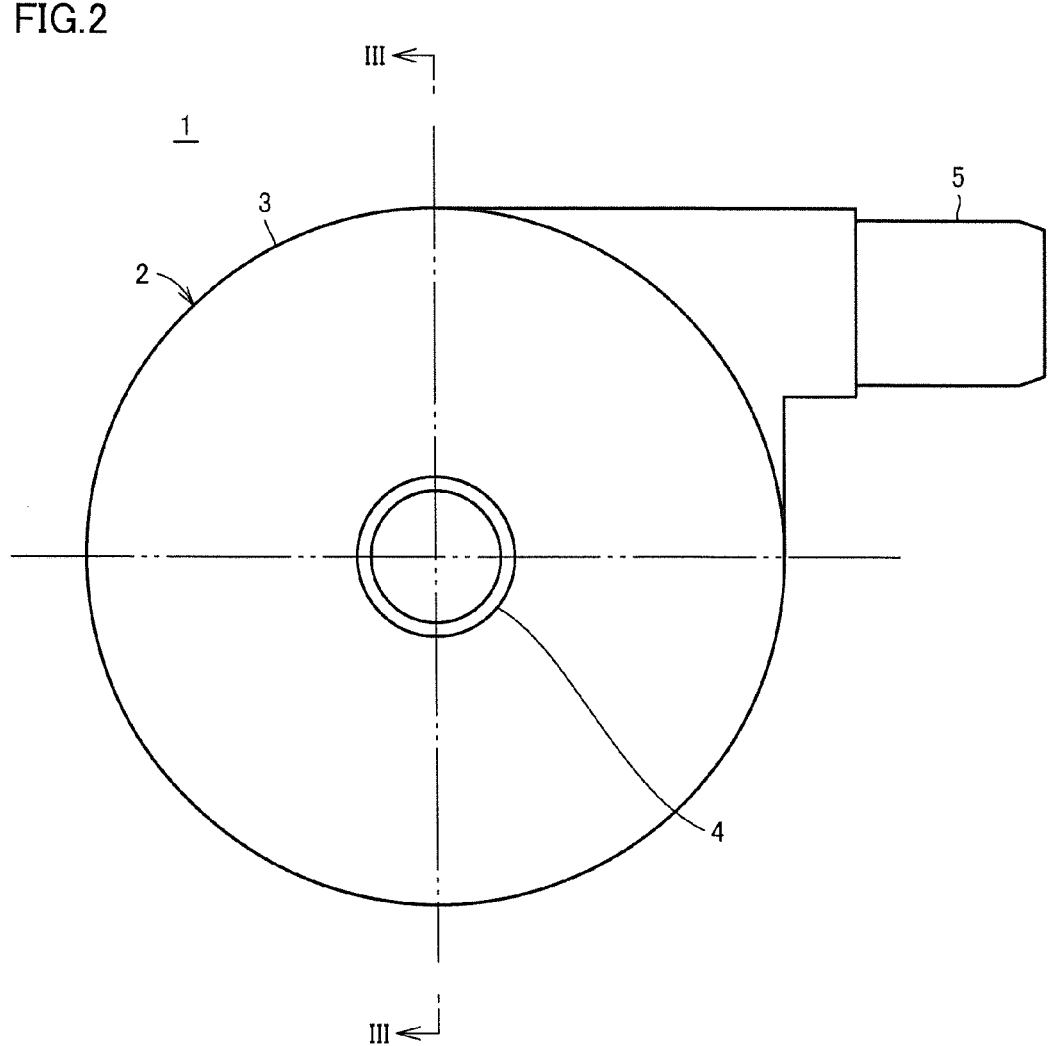
FIG. 2 is a side view of the pump unit shown in FIG. 1.

In FIGS. 1 to 7, a pump unit 1 of this centrifugal blood pump apparatus includes a housing 2 made of a nonmagnetic material. Housing 2 includes a cylindrical body portion 3, a cylindrical blood inlet port 4 provided to stand at a center of one end surface of body portion 3, and a cylindrical blood outlet port 5 provided on an outer circumferential surface of body portion 3. Blood outlet port 5 extends in a tangential direction of the outer circumferential surface of body portion 3.

Figure 3:
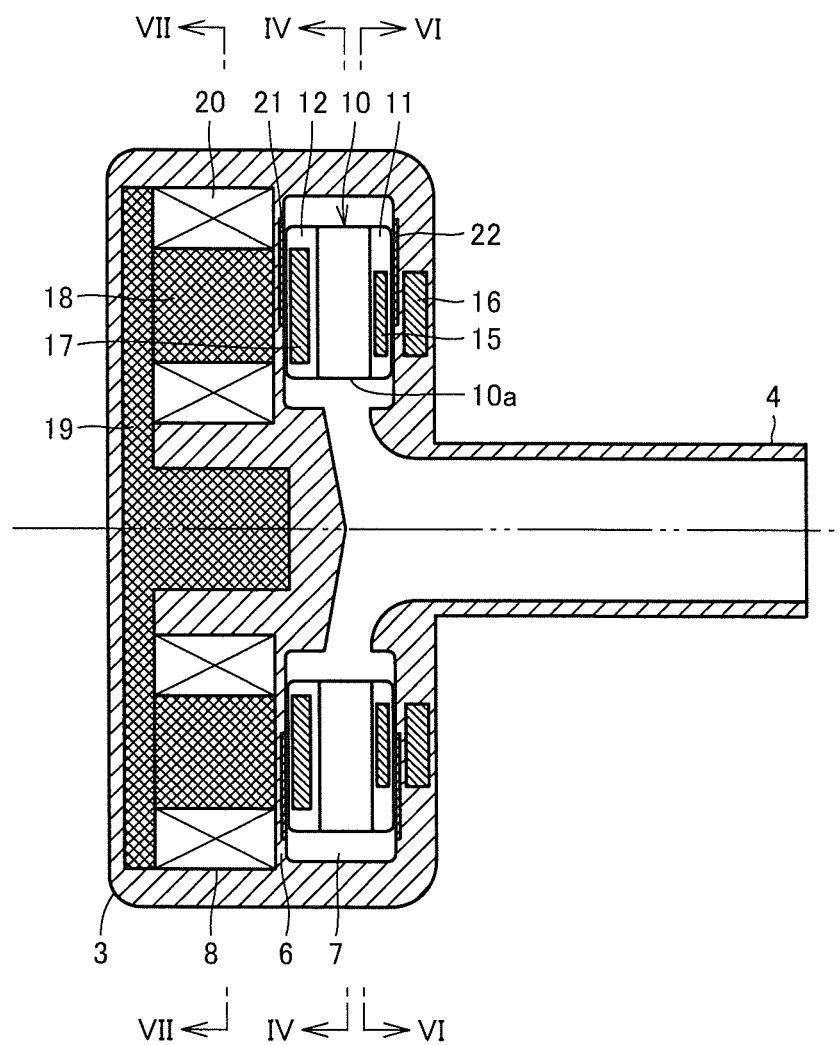
FIG. 3 is a cross-sectional view along the line in III-III FIG. 2.
Figure 4:
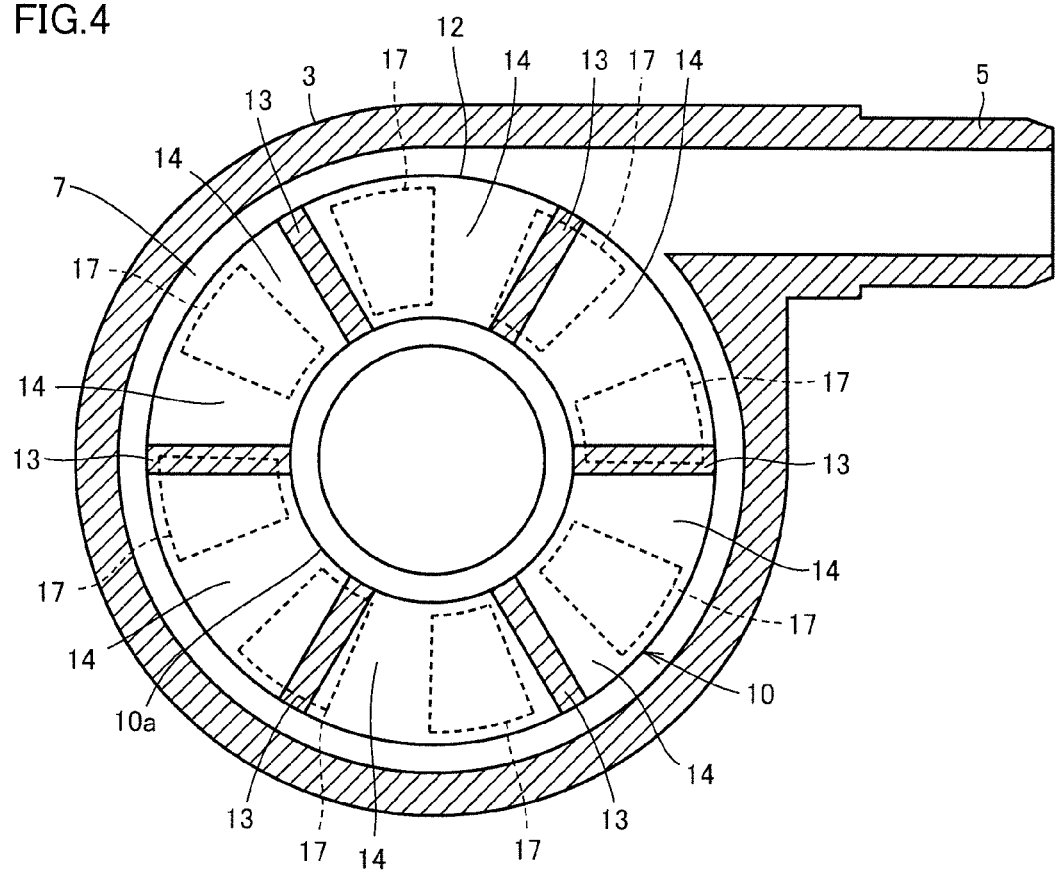
FIG. 4 is a cross-sectional view along the line IV-IV in FIG. 3.

In housing 2, as shown in FIG. 3, a blood chamber 7 and a motor chamber 8 partitioned from each other by a diaphragm 6 are provided. In blood chamber 7, as shown in FIGS. 3 and 4, a disc-shaped impeller 10 having a through hole 10a in a center thereof is rotatably provided. Impeller 10 includes two shrouds 11, 12 in a doughnut plate shape, and a plurality of (e.g., six) vanes 13 formed between two shrouds 11 and 12. Shroud 11 is arranged closer to blood inlet port 4, and shroud 12 is arranged closer to diaphragm 6. Shrouds 11, 12 and vanes 13 are made of a nonmagnetic material.

A plurality of (six in this case) blood passages 14 partitioned from one another by the plurality of vanes 13 are formed between two shrouds 11 and 12. As shown in FIG. 4, blood passage 14 is in communication with through hole 10a in the center of impeller 10, and extends with through hole 10a of impeller 10 as a starting point to an outer circumference such that blood passage 14 gradually increases in width. In other words, vane 13 is formed between two adjacent blood passages 14. In the first embodiment, the plurality of vanes 13 are provided at equiangular intervals, and have the same shape. Thus, the plurality of blood passages 14 are provided at equiangular intervals, and have the same shape.

When impeller 10 is driven to rotate, blood that has flowed in through blood inlet port 4 is delivered by a centrifugal force from through hole 10a to an outer circumferential portion of impeller 10 via blood passages 14, and flows out through blood outlet port 5.

A permanent magnet 15 is embedded in shroud 11, and a permanent magnet 16 for attracting permanent magnet 15 is embedded in an inner wall of blood chamber 7 facing shroud 11. Permanent magnets 15 and 16 are provided to attract (in other words, bias) impeller 10 to the side opposite to motor chamber 8, namely, toward blood inlet port 4.

Instead of providing permanent magnets 15 and 16 in shroud 11 and in the inner wall of blood chamber 7, respectively, a permanent magnet may be provided in one of shroud 11 and the inner wall of blood chamber 7, and a magnetic material may be provided in the other. Alternatively, shroud 11 itself may be formed of permanent magnet 15 or a magnetic material. Either a soft magnetic material or a hard magnetic material may be used as the magnetic material.

Permanent magnet 16 may be a single magnet, or a plurality of magnets. If it is a single magnet, permanent magnet 16 is formed in a ring shape. If it is a plurality of magnets, permanent magnets 16 are arranged at equiangular intervals along a single circle. As with permanent magnet 16, permanent magnet 15 may also be a single magnet, or a plurality of magnets.

As shown in FIGS. 3 and 4, a plurality of (e.g., eight) permanent magnets 17 are embedded in shroud 12. The plurality of permanent magnets 17 are arranged with a gap therebetween at equiangular intervals along a single circle such that adjacent magnetic polarities are different from each other. In other words, permanent magnet 17 having the N-pole oriented to motor chamber 8 and permanent magnet 17 having the S-pole oriented to motor chamber 8 are alternately arranged with a gap therebetween at equiangular intervals along a single circle.

Figure 7:
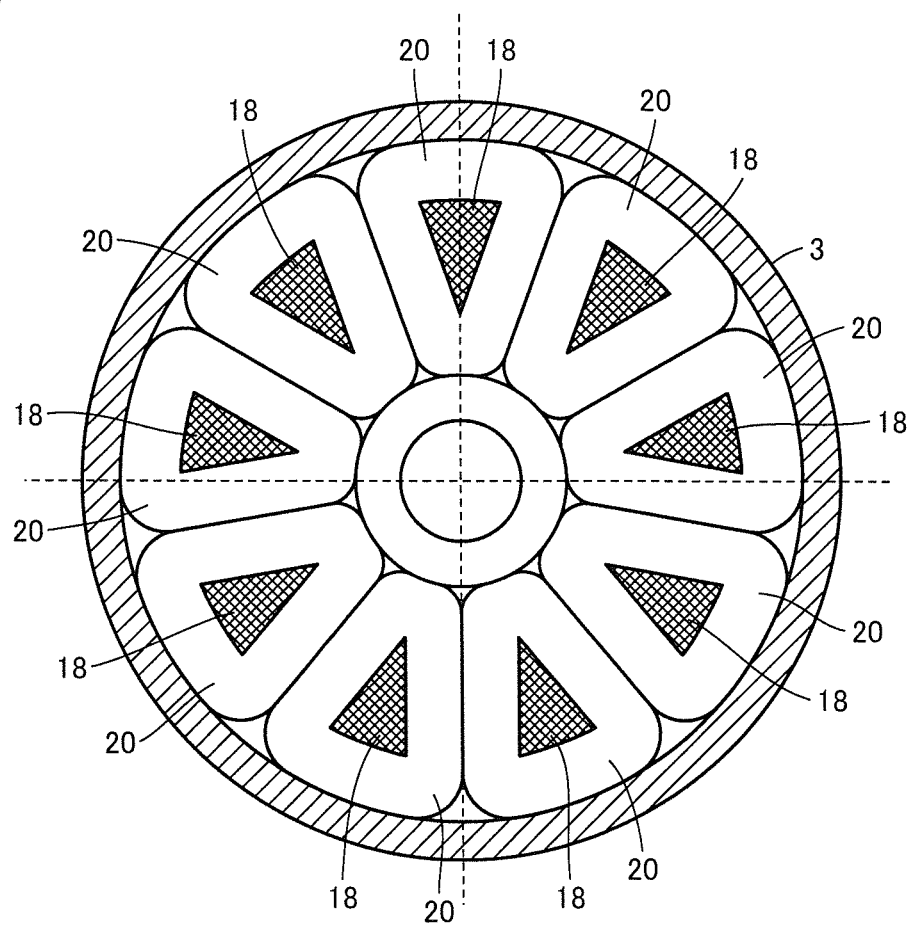
FIG. 7 is a cross-sectional view along the line VII-VII in FIG. 3.

As shown in FIG. 7, a plurality of (e.g., nine) magnetic materials 18 are provided in motor chamber 8. The plurality of magnetic materials 18 are arranged at equiangular intervals along a single circle to face the plurality of permanent magnets 17 in impeller 10. A base end of each of the plurality of magnetic materials 18 is joined to one disc-shaped yoke 19. A coil 20 is wound around each magnetic material 18.

Each of the plurality of magnetic materials 18 is formed in a shape of a triangular prism of the same dimensions. In addition, space for winding coil 20 is equally secured around the plurality of magnetic materials 18, and opposite surfaces of every two adjacent magnetic materials 18 are provided substantially parallel to each other. Thus, large space for coils 20 can be secured, to increase turns of coils 20. As a result, large torque for driving impeller 10 to rotate can be generated. Further, copper loss that occurs in coils 20 can be reduced, thereby enhancing energy efficiency in driving impeller 10 to rotate.

An outline surface surrounding the plurality of magnetic materials 18 (a circle surrounding the peripheries of the plurality of magnetic materials 18 in FIG. 7) may correspond to an outline surface surrounding the plurality of permanent magnets 17 (a circle surrounding the peripheries of the plurality of magnetic materials 17 in FIG. 4), or the outline surface surrounding the plurality of magnetic materials 18 may be larger than the outline surface surrounding the plurality of permanent magnets 17. Further, it is preferable that magnetic material 18 be designed not to be magnetically saturated at maximum rating of pump 1 (a condition where torque for driving impeller 10 to rotate becomes maximum).

Each magnetic material 18 may be formed in a cylindrical shape. In this case, a circumferential length of coils 20 can be minimized to reduce copper loss that occurs in coils 20, thereby enhancing energy efficiency in driving impeller 10 to rotate.

Figure 8:
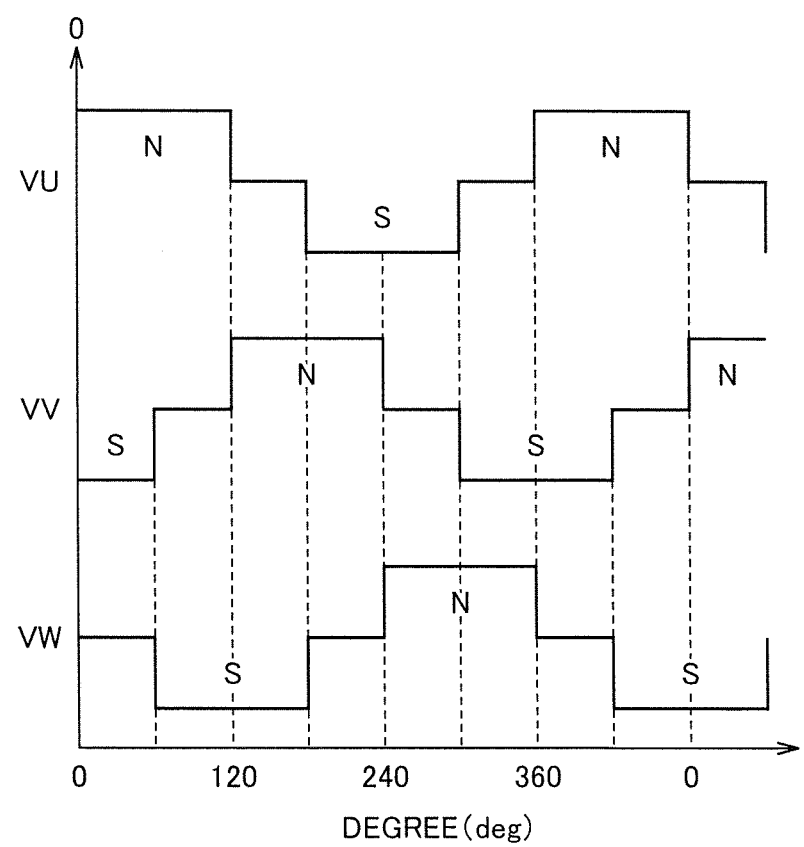
FIG. 8 is a time chart illustrating voltages applied to a plurality of coils shown in FIG. 7.

Voltages are applied to nine coils 20 in a power distribution system shifted by 120 degrees, for example. That is, nine coils 20 are divided into groups each including three coils. Voltages VU, VV and VW as shown in FIG. 8 are applied to first to third coils 20 of each group, respectively. To first coil 20, a positive voltage is applied during a period of 0 to 120 degrees, 0 V is applied during a period of 120 to 180 degrees, a negative voltage is applied during a period of 180 to 300 degrees, and 0 V is applied during a period of 300 to 360 degrees. Accordingly, a tip surface of magnetic material 18 having first coil 20 wound therearound (end surface closer to impeller 10) becomes the N-pole during the period of 0 to 120 degrees, and becomes the S-pole during the period of 180 to 300 degrees. Voltage VV is delayed in phase from voltage VU by 120 degrees, and voltage VW is delayed in phase from voltage VV by 120 degrees. Thus, a rotating magnetic field can be generated by applying voltages VU, VV and VW to first to third coils 20, respectively, and impeller 10 can be rotated by an attractive force and a repulsion force between the plurality of magnetic materials 18 and the plurality of permanent magnets 17 in impeller 10.

When impeller 10 is rotating with a rated rotation speed, the attractive force between permanent magnets 15 and 16, and the attractive force between the plurality of permanent magnets 17 and the plurality of magnetic materials 18 are set to be balanced with each other substantially in a center of a movable range of impeller 10 in blood chamber 7. Thus, an acting force due to the attractive force on impeller 10 is very small throughout the movable range of impeller 10. Consequently, frictional resistance during relative slide between impeller 10 and housing 2 which occurs when impeller 10 is activated to rotate can be reduced. In addition, a surface of impeller 10 and a surface of an inner wall of housing 2 are not damaged (no projections and depressions in the surfaces) during the relative slide, and moreover, impeller 10 is readily levitated from housing 2 without contacting even when hydrodynamic pressure is small during low-speed rotation. Accordingly, occurrence of hemolysis/thrombus due to the relative slide between impeller 10 and housing 2, or occurrence of thrombus due to small damage (projections and depressions) to the surfaces which occurs during the relative slide can be avoided.

A plurality of grooves for hydrodynamic bearing 21 are formed in a surface of diaphragm 6 facing shroud 12 of impeller 10, and a plurality of grooves for hydrodynamic bearing 22 are formed in the inner wall of blood chamber 7 facing shroud 11. When a rotation speed of impeller 10 becomes higher than a predetermined rotation speed, a hydrodynamic bearing effect is produced between grooves for hydrodynamic bearing 21, 22 and impeller 10, respectively. As a result, drag is generated on impeller 10 from grooves for hydrodynamic bearing 21 and 22, causing impeller 10 to rotate without contacting in blood chamber 7.

Figure 5:
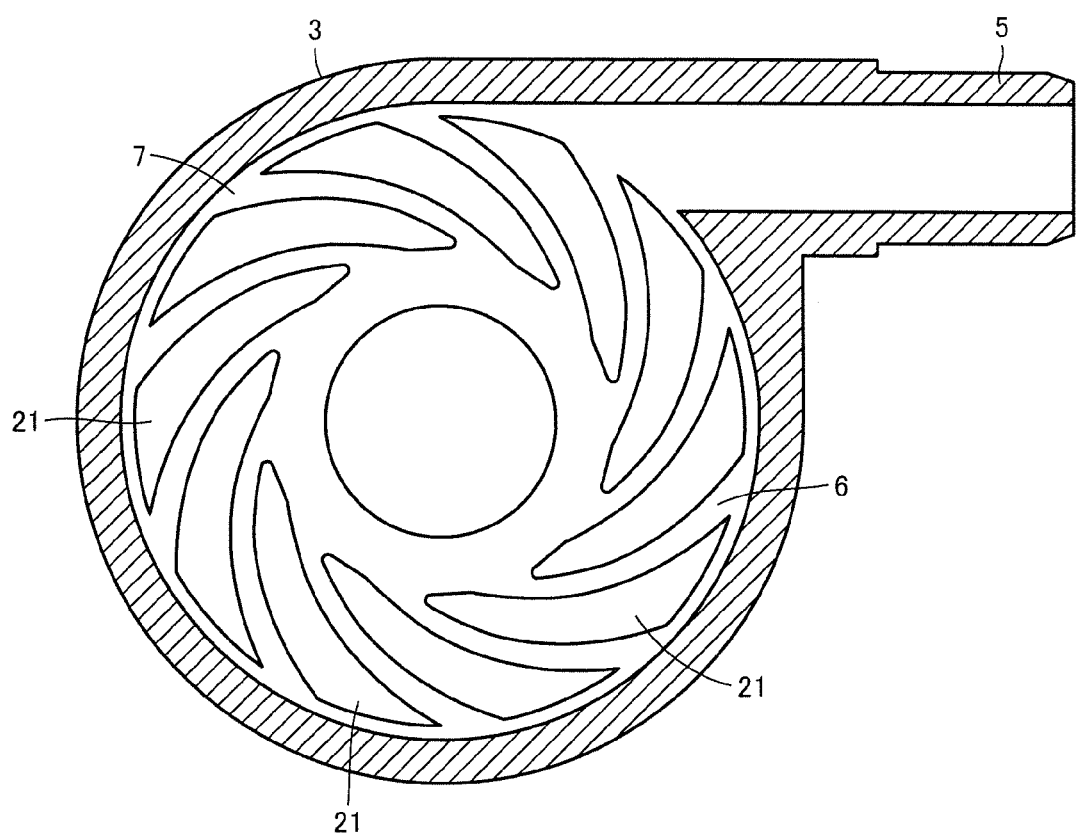
FIG. 5 is a cross-sectional view showing a state where an impeller has been removed from the cross-sectional view along the line IV-IV in FIG. 3.

Specifically, as shown in FIG. 5, the plurality of grooves for hydrodynamic bearing 21 are formed with a size corresponding to shroud 12 of impeller 10. Each of grooves for hydrodynamic bearing 21 has one end on an edge (circumference) of a circular portion slightly distant from a center of diaphragm 6, and extends spirally (in other words, in a curved manner) to a portion near an outer edge of diaphragm 6 such that grooves for hydrodynamic bearing 21 gradually increase in width. The plurality of grooves for hydrodynamic bearing 21 have substantially the same shape, and are arranged at substantially the same intervals. Grooves for hydrodynamic bearing 21 are concave portions, and preferably have a depth of about 0.005 to 0.4 mm. It is preferable that about 6 to 36 grooves for hydrodynamic bearing 21 be provided.

In FIG. 5, ten grooves for hydrodynamic bearing 21 are equiangularly arranged with respect to a central axis of impeller 10. Since grooves for hydrodynamic bearing 21 have a so-called inward spiral groove shape, clockwise rotation of impeller 10 causes increase in liquid pressure from an outer diameter portion toward an inner diameter portion of grooves for hydrodynamic bearing 21. As a result, a repulsion force is generated between impeller 10 and diaphragm 6, and this acts as hydrodynamic pressure.

Instead of providing grooves for hydrodynamic bearing 21 in diaphragm 6, grooves for hydrodynamic bearing 21 may be provided in a surface of shroud 12 of impeller 10.

In this manner, owing to the hydrodynamic bearing effect produced between impeller 10 and the plurality of grooves for hydrodynamic bearing 21, impeller 10 moves away from diaphragm 6, and rotates without contacting. Accordingly, a blood flow path is secured between impeller 10 and diaphragm 6, thus preventing occurrence of blood accumulation therebetween and the resultant thrombus. Further, in a normal state, grooves for hydrodynamic bearing 21 exercise a stirring effect between impeller 10 and diaphragm 6, thus preventing occurrence of partial blood accumulation therebetween.

It is preferable that a corner portion of each of grooves for hydrodynamic bearing 21 be rounded to have R of at least equal to higher than 0.05 mm. As a result, occurrence of hemolysis can be further reduced.

Figure 6:
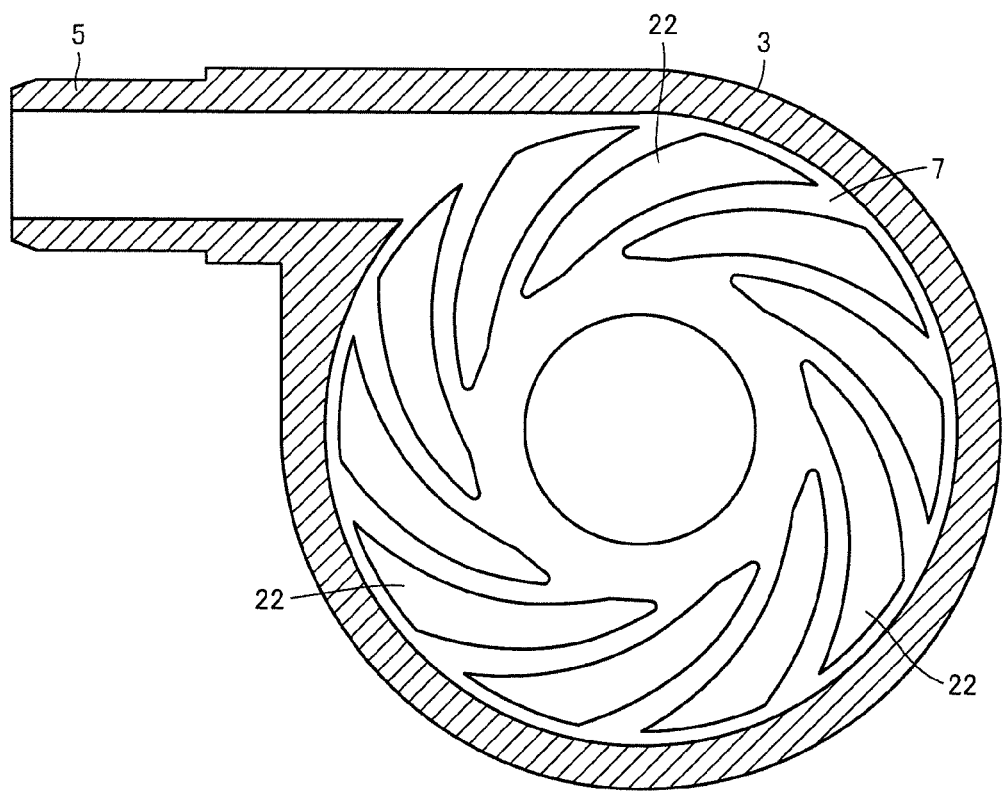
FIG. 6 is a cross-sectional view showing the state where the impeller has been removed from a cross-sectional view along the line VI-VI in FIG. 3.

As with the plurality of grooves for hydrodynamic bearing 21, as shown in FIG. 6, the plurality of grooves for hydrodynamic bearing 22 are formed with a size corresponding to shroud 11 of impeller 10. Each of grooves for hydrodynamic bearing 22 has one end on an edge (circumference) of a circular portion slightly distant from a center of the inner wall of blood chamber 7, and extends spirally (in other words, in a curved manner) to a portion near an outer edge of the inner wall of blood chamber 7 such that grooves for hydrodynamic bearing 22 gradually increase in width. The plurality of grooves for hydrodynamic bearing 22 have substantially the same shape, and are arranged at substantially the same intervals. Grooves for hydrodynamic bearing 22 are concave portions, and preferably have a depth of about 0.005 to 0.4 mm. It is preferable that about 6 to 36 grooves for hydrodynamic bearing 22 be provided. In FIG. 6, ten grooves for hydrodynamic bearing 22 are equiangularly arranged with respect to the central axis of impeller 10.

Instead of providing grooves for hydrodynamic bearing 22 in the inner wall of blood chamber 7, grooves for hydrodynamic bearing 22 may be provided in a surface of shroud 11 of impeller 10. It is preferable that a corner portion of each of grooves for hydrodynamic bearing 22 be rounded to have R of at least equal to or higher than 0.05 mm. As a result, occurrence of hemolysis can be further reduced.

In this manner, owing to the hydrodynamic bearing effect produced between impeller 10 and the plurality of grooves for hydrodynamic bearing 22, impeller 10 moves away from the inner wall of blood chamber 7, and rotates without contacting. In addition, when pump unit 1 is subject to external impact, or when the hydrodynamic pressure by grooves for hydrodynamic bearing 21 becomes excessive, impeller 10 can be prevented from being in close contact with the inner wall of blood chamber 7. The hydrodynamic pressure generated by grooves for hydrodynamic bearing 21 may be different from the hydrodynamic pressure generated by grooves for hydrodynamic bearing 22.

It is preferable that impeller 10 rotate in a state where a gap between shroud 12 of impeller 10 and diaphragm 6 is substantially equal to a gap between shroud 11 of impeller 10 and the inner wall of blood chamber 7. If one of the gaps becomes narrower due to serious disturbance such as a hydrodynamic force acting on impeller 10, it is preferable that grooves for hydrodynamic bearing 21 and 22 have different shapes, so that the hydrodynamic pressure by the grooves for hydrodynamic bearing on the narrower side becomes higher than the hydrodynamic pressure by the other grooves for hydrodynamic bearing to make the gaps substantially equal to each other.

While both of grooves for hydrodynamic bearing 21 and 22 have the inward spiral groove shape in FIGS. 5 and 6, grooves for hydrodynamic bearing 21 and 22 having another shape may be used. Nevertheless, for blood circulation, it is preferable to employ grooves for hydrodynamic bearing 21 and 22 having the inward spiral groove shape that allows a smooth flow of blood.

Figure 9:
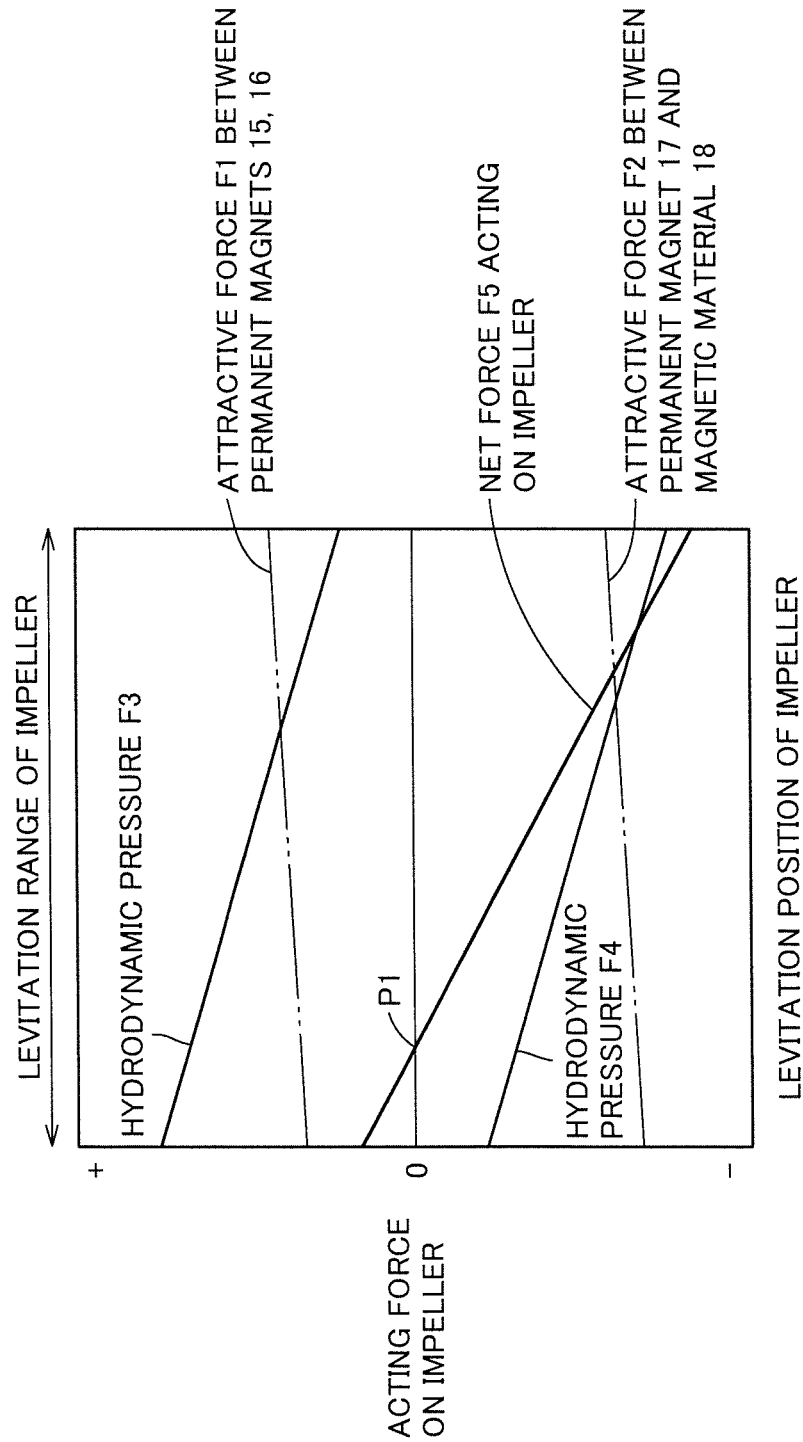
FIG. 9 explains a levitation position of the impeller shown in FIG. 3.

FIG. 9 illustrates forces acting on impeller 10 when magnitude of a resultant force of an attractive force F1 between permanent magnets 15 and 16 and an attractive force F2 between permanent magnet 17 and magnetic material 18 is adjusted to be zero in a position P1 other than a central position of the movable range of impeller 10 in blood chamber 7. The rotation speed of impeller 10 is kept at a rated value.

That is, a levitation position of impeller 10 when attractive force F1 between permanent magnets 15 and 16 is set to be smaller than attractive force F2 between permanent magnet 17 and magnetic material 18 and their resultant force becomes zero is closer to diaphragm 6 relative to the center of the movable range of the impeller. Grooves for hydrodynamic bearing 21 and 22 have the same shape.

A horizontal axis of FIG. 9 represents a position of impeller 10 (the left side in the figure being closer to the diaphragm 6), and a vertical axis represents acting forces on impeller 10. An acting force on impeller 10 toward diaphragm 6 is expressed as a negative acting force. As the acting forces on impeller 10, attractive force F1 between permanent magnets 15 and 16, attractive force F2 between permanent magnet 17 and magnetic material 18, a hydrodynamic pressure F3 by grooves for hydrodynamic bearing 21, a hydrodynamic pressure F4 by grooves for hydrodynamic bearing 22, and a "net force F5 acting on impeller" which is their resultant force are illustrated.

As can be seen from FIG. 9, in a position where net force F5 acting on impeller 10 becomes zero, the levitation position of impeller 10 is significantly deviated from the central position of the movable range of impeller 10. As a result, a distance between rotating impeller 10 and diaphragm 6 becomes narrower, and impeller 10 is brought into contact with diaphragm 6 even by the action of a small disturbance force on impeller 10.

Figure 10:
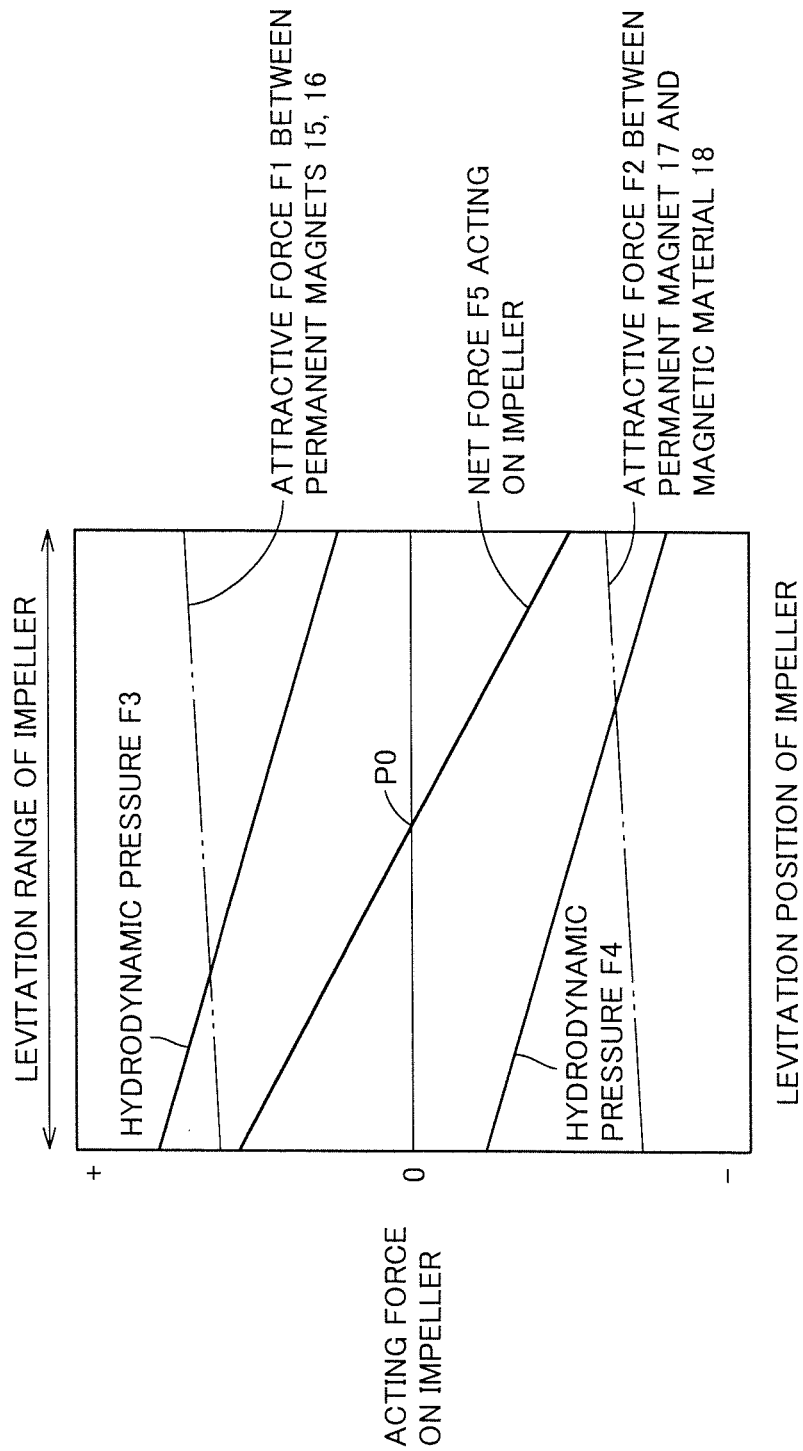
FIG. 10 explains a levitation position of the impeller shown in FIG. 3.

In contrast, FIG. 10 illustrates forces acting on impeller 10 when the magnitude of the resultant force of attractive force F1 between permanent magnets 15 and 16 and attractive force F2 between permanent magnet 17 and magnetic material 18 is adjusted to be zero in a central position P0 of the movable range of impeller 10 in blood chamber 7. The rotation speed of impeller 10 is kept at the rated value in this case as well.

That is, attractive force F1 between permanent magnets 15 and 16 and attractive force F2 between permanent magnet 17 and magnetic material 18 are set to be substantially equal to each other. In addition, grooves for hydrodynamic bearing 21 and 22 have the same shape. In this case, supporting rigidity for the levitation position of impeller 10 is high as compared to the example shown in FIG. 9. Further, since net force F5 acting on impeller 10 is zero in the center of the movable range, impeller 10 is levitated in the central position when a disturbance force is not acting on impeller 10.

As such, a levitation position of impeller 10 is determined by a balance among attractive force F1 between permanent magnets 15 and 16, attractive force F2 between permanent magnet 17 and magnetic material 18, and hydrodynamic pressures F3, F4 generated by grooves for hydrodynamic bearing 21 and 22 during rotation of impeller 10. By making F1 and F2 substantially equal to each other, and by forming grooves for hydrodynamic bearing 21 and 22 in the same shape, impeller 10 can be levitated substantially in a central portion of blood chamber 7 during rotation of impeller 10. Since impeller 10 has a shape in which the vanes are formed between the two discs, as shown in FIGS. 3 and 4, two surfaces facing the inner wall of housing 2 can be formed in the same shape and of the same dimensions. Therefore, it is possible to provide grooves for hydrodynamic bearing 21 and 22 having substantially the same hydrodynamic pressure generating function on both sides of impeller 10.

In this case, impeller 10 is levitated in the central position of blood chamber 7, and thus held in a position farthest from the inner wall of housing 2. As a result, even if the levitation position of impeller 10 is changed due to application of a disturbance force to levitated impeller 10, the possibility that impeller 10 is brought into contact with the inner wall of housing 2 is reduced, thus reducing the possibility of occurrence of thrombus and hemolysis resulting from such contact.

While two grooves for hydrodynamic bearing 21 and 22 have the same shape in the examples shown in FIGS. 9 and 10, grooves for hydrodynamic bearing 21 and 22 may have different shapes and different hydrodynamic pressure generating functions. For example, when disturbance acts on impeller 10 always in one direction due to a hydrodynamic force or the like during pumping, the function of grooves for hydrodynamic bearing in the disturbance direction may be made greater than the function of the other grooves for hydrodynamic bearing, thereby levitating and rotating impeller 10 in the central position of housing 2. As a result, the possibility of contact between impeller 10 and housing 2 can be reduced, thereby attaining stable levitation function of impeller 10.

Furthermore, when an absolute value of a negative axial supporting rigidity value of impeller 10 which is constituted of attractive force F1 between permanent magnets 15 and 16 and attractive force F2 between permanent magnet 17 and magnetic material 18 is expressed as Ka, an absolute value of a positive radial rigidity value is expressed as Kr, and an absolute value of a positive rigidity value obtained by two grooves for hydrodynamic bearing 21 and 22 in a normal rotation speed range where impeller 10 rotates is expressed as Kg, it is preferable that a relation of Kg>Ka+Kr be satisfied.

Specifically, when absolute value Ka of the negative axial rigidity value is 20000 N/m, and absolute value Kr of the positive radial rigidity value is 10000 N/m, absolute value Kg of the positive rigidity value obtained by two grooves for hydrodynamic bearing 21 and 22 in the rotation speed range where impeller 10 normally rotates is set to a value higher than 30000 N/m.

The axial supporting rigidity for impeller 10 is a value obtained by subtracting negative rigidity due to the attractive force between the magnetic materials and the like from rigidity resulting from the hydrodynamic pressures generated by grooves for hydrodynamic bearing 21 and 22. Thus, by satisfying the relation of Kg>Ka+Kr, the axial supporting rigidity for impeller 10 can be made higher than the radial supporting rigidity. With such setting, movement of impeller 10 can be suppressed more in the axial direction than in the radial direction when a disturbance force acts on impeller 10, thereby avoiding mechanical contact between impeller 10 and housing 2 in a portion where grooves for hydrodynamic bearing 21 are formed.

In particular, since grooves for hydrodynamic bearing 21 and 22 are provided as concave portions in the planes as shown in FIGS. 5 and 6, mechanical contact between housing 2 and impeller 10 in these sites during rotation of impeller 10 may result in damage to one or both of a surface of impeller 10 and a surface of the inner wall of housing 2 (projections and depressions in the surfaces), and blood passage through this portion may cause occurrence of thrombus and hemolysis. In order to prevent mechanical contact at grooves for hydrodynamic bearing 21 and 22 to suppress thrombus and hemolysis, it is effective to make the axial rigidity higher than the radial rigidity.

Whirl occurs in unbalanced impeller 10 during rotation, and this whirl is greatest when a natural frequency determined by the mass of impeller 10 and the supporting rigidity value of impeller 10 matches the rotation speed of impeller 10.

Since the radial supporting rigidity for impeller 10 is smaller than the axial supporting rigidity in pump unit 1, it is preferable to set a maximum rotation speed of impeller 10 to be equal to or lower than the radial natural frequency. Accordingly, in order to prevent mechanical contact between impeller 10 and housing 2, when a radial rigidity value of impeller 10 which is constituted of attractive force F1 between permanent magnets 15 and 16 and attractive force F2 between permanent magnet 17 and magnetic material 18 is expressed as Kr (N/m), the mass of impeller 10 is expressed as m (kg), and the rotation speed of the impeller is expressed as $\omega$ (rad/s), it is preferable that a relation of $\omega < (Kr/m)^{0.5}$ be satisfied.

Specifically, when the mass of impeller 10 is 0.03 kg and the radial rigidity value is 2000 N/m, the maximum rotation speed of impeller 10 is set to be equal to or lower than 258 rad/s (2465 rpm). Conversely, when the maximum rotation speed of impeller 10 is set to 366 rad/s (3500 rpm), the radial rigidity is set to be equal to or higher than 4018 N/m.

It is further preferable to set the maximum rotation speed of impeller 10 to be equal to or lower than 80% of this $\omega$. Specifically, when the mass of impeller 10 is 0.03 kg and the radial rigidity value is 2000 N/m, the maximum rotation speed is set to be equal to or lower than 206.4 rad/s (1971 rpm). Conversely, when it is desired to set the maximum rotation speed of impeller 10 to 366 rad/s (3500 rpm), the radial rigidity value is set to be equal to or higher than 6279 N/m. By setting the maximum rotation speed of impeller 10 in this manner, contact between rotating impeller 10 and housing 2 can be suppressed.

When the rigidity due to the hydrodynamic pressures by grooves for hydrodynamic bearing 21 and 22 becomes higher than the negative axial rigidity value of impeller 10 which is constituted of attractive force F1 between permanent magnets 15 and 16 and attractive force F2 between permanent magnet 17 and magnetic material 18, impeller 10 and housing 2 are not in contact with each other. It is thus preferable to minimize this negative rigidity value. In order to keep this negative rigidity value low, it is preferable that the opposite surfaces of permanent magnets 15 and 16 have different sizes. For example, by making the size of permanent magnet 16 smaller than that of permanent magnet 15, a rate of change in attractive force that varies with a distance between the magnets, namely, the negative rigidity can be suppressed to low level, thereby preventing reduction in supporting rigidity for the impeller.

It is also preferable to check to see that impeller 10 is in contact with diaphragm 6 before activating impeller 10 to rotate.

Namely, when impeller 10 is not rotating, impeller 10 is not supported without contacting by grooves for hydrodynamic bearing 21 and 22, but is in contact with housing 2 with a high surface pressure due to attractive force F1 between permanent magnets 15 and 16 and attractive force F2 between permanent magnet 17 and magnetic material 18. Further, when impeller 10 is rotated by magnetic interaction between coil 20 and magnetic material 18 in motor chamber 8 and permanent magnet 7 in impeller 10 as in pump unit 1, starting torque is small as compared to an example where an impeller is driven to rotate by magnetic coupling between permanent magnets as shown in FIG. 3 of PTL 2. It is thus difficult to smoothly activate impeller 10 to rotate.

When shroud 12 of impeller 10 is in contact with diaphragm 6, however, permanent magnet 17 in impeller 10 and magnetic material 18 in motor chamber 8 are closer to each other than when shroud 11 of impeller 10 is in contact with the inner wall of blood chamber 7, which allows increase in rotational torque during activation of impeller 10, thereby smoothly activating impeller 10 to rotate.

As described above, however, when impeller 10 is rotating, attractive force F1 between permanent magnets 15 and 16 and attractive force F2 between permanent magnet 17 and magnetic material 18 are set to be balanced with each other when the position of impeller 10 is near the center of the movable range of impeller 10. Thus, impeller 10 is not necessarily in contact with diaphragm 6 when impeller 10 is not rotating.

For this reason, this centrifugal blood pump apparatus is provided with means for moving impeller 10 toward diaphragm 6 before activating impeller 10 to rotate. Specifically, a current is fed through the plurality of coils 20 such that attractive force F2 between permanent magnet 17 and magnetic material 18 becomes higher, to move impeller 10 toward diaphragm 6.

Figure 11:
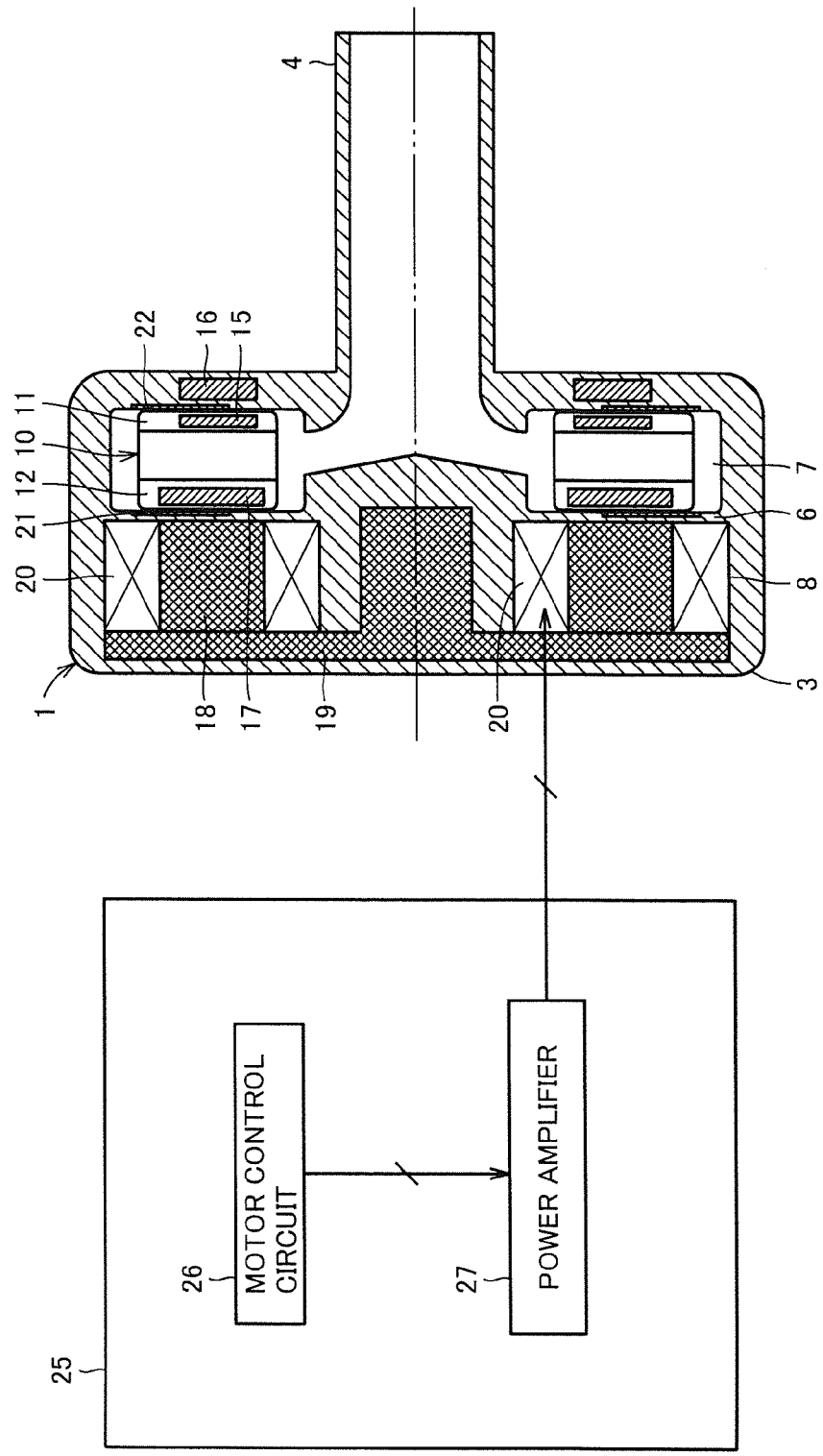
FIG. 11 is a block diagram showing a structure of a controller for controlling the pump unit shown in FIGS. 1 to 7.

FIG. 11 is a block diagram showing a structure of a controller 25 for controlling pump unit 1. In FIG. 11, controller 25 includes a motor control circuit 26 and a power amplifier 27. Motor control circuit 26 outputs three-phase control signals in the power distribution system shifted by 120 degrees, for example. Power amplifier 27 amplifies the three-phase control signals from motor control circuit 26, and generates three-phase voltages VU, VV and VW shown in FIG. 8. Three-phase voltages VU, VV and VW are applied to first to third coils 20 described with reference to FIGS. 7 and 8, respectively. As a result, during normal operation, impeller 10 rotates with a predetermined rotation speed in the central position of the movable range.

Figure 12:
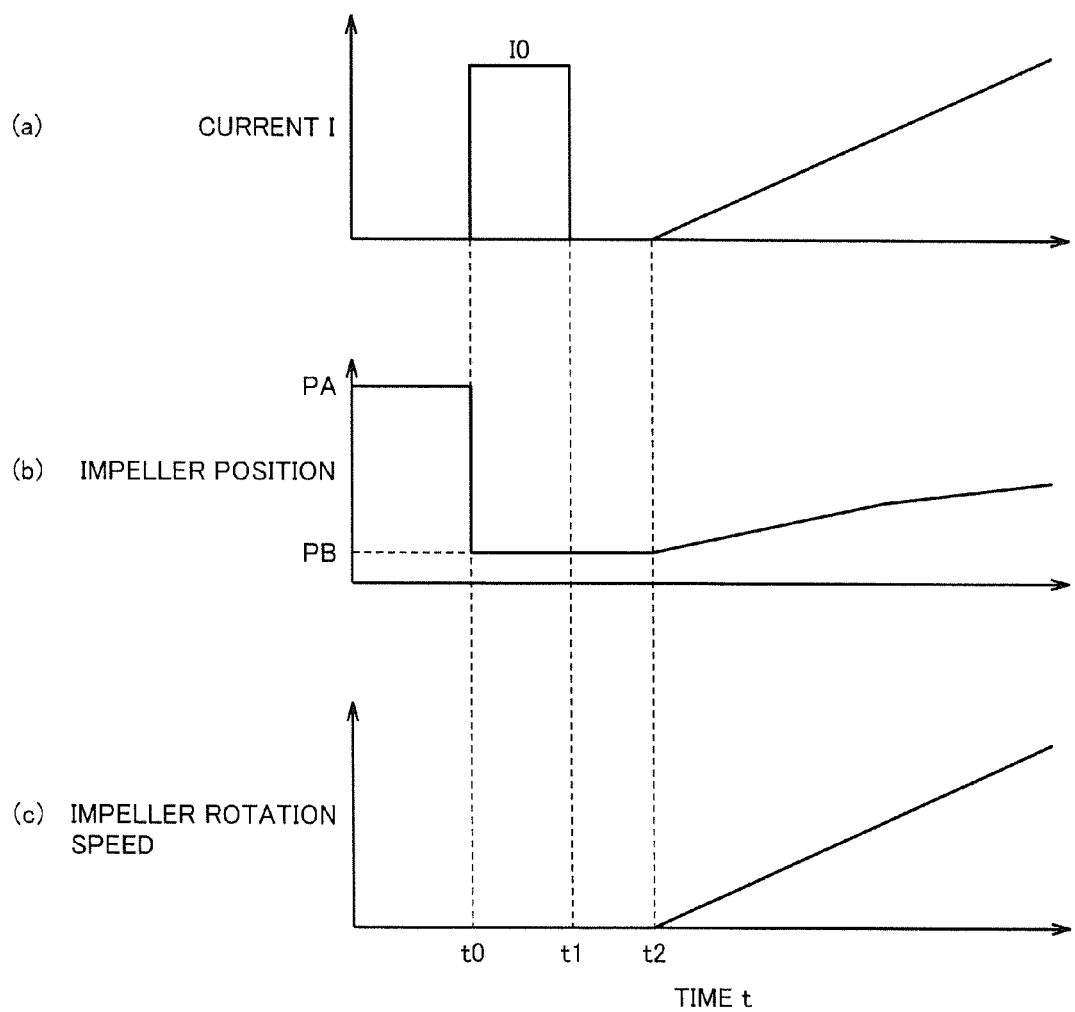
FIG. 12 is a time chart illustrating operation of the controller shown in FIG. 11.

FIG. 12 (a) to (c) are time charts illustrating temporal variations of a coil current I when activating impeller 10 to rotate, the position of impeller 10, and the rotation speed of impeller 10. Referring to FIG. 12 (a) to (c), in an initial state, shroud 11 of impeller 10 is in contact with the inner wall of blood chamber 7, and impeller 10 is in a position PA. At time t0, a predetermined current I0 is fed through coils 20. As a result, attractive force F2 between permanent magnet 17 and magnetic material 18 becomes higher than attractive force F1 between permanent magnets 15 and 16, so that impeller 10 moves to a position PB closer to diaphragm 6, causing shroud 12 of impeller 10 to be in contact with diaphragm 6. When impeller 10 moves to position PB, current I0 is cut off (time t1). It is preferable to provide a sensor for detecting a position of impeller 10 in blood chamber 7, and check to see that impeller 10 is in contact with diaphragm 6 before cutting off current I0.

Then, coil current I is gradually increased to a predetermined rated value. Here, impeller 10 is in contact with diaphragm 6, and thus smoothly rotates. With the increase in coil current I, impeller 10 moves from position PB closer to diaphragm 6 to the central position of the movable range.

The effect of the first embodiment is now described. FIG. 13 shows a comparative example of the first embodiment, which is compared to FIG. 4. In FIG. 13, this comparative example is different from the first embodiment in that there is no gap between the plurality of permanent magnets 17.

FIG. 14 (a) shows a magnetic field between permanent magnets 17 and 17 in the first embodiment, and FIG. 14 (b) shows a magnetic field between permanent magnets 17 and 17 in the comparative example. As can be seen from FIG. 14 (a) and (b), when permanent magnet 17 in the first embodiment and permanent magnet 17 in the comparative example have the same weight, magnetic flux density between permanent magnets 17 and 17 is higher in the first embodiment, and a magnetic field around permanent magnets 17 is stronger in the first embodiment. In the first embodiment, therefore, a magnetic coupling force between permanent magnets 17 in impeller 10 and magnetic materials 18 and coils 20 in motor chamber 8 can be increased. Accordingly, the rotational torque of impeller 10 can be increased while maintaining small device dimensions.

Figure 15:
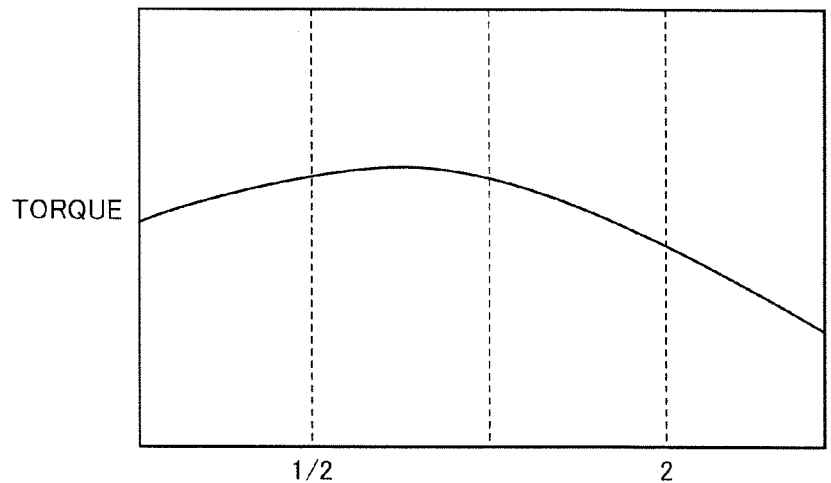
FIG. 15 illustrates relation between an area ratio of a gap portion to a permanent magnet shown in FIG. 14 and rotational torque.

FIG. 15 illustrates relation between a ratio Sd/Sm of an area Sd of the gap portion between permanent magnets 17 and 17 to an area Sm of permanent magnet 17 and the rotational torque of impeller 10. It is noted that the weight of permanent magnet 17 is maintained constant. In FIG. 15, the rotational torque gradually increases as Sd/Sm gradually increases from 0, and the rotational torque becomes maximum when Sd/Sm is about ¾. The rotational torque gradually decreases as Sd/Sm gradually increases from ¾, and the rotational torque becomes lower than when Sd/Sm=0 when Sd/Sm becomes higher than about 1.75. Accordingly, a preferable value of Sd/Sm is about ¾, and a preferable range of Sd/Sm is in a rage from 0.5 to 1.

Figure 16:
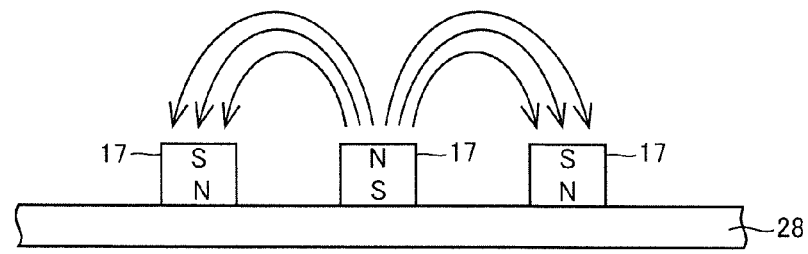
FIG. 16 shows a modification of the first embodiment.

Various modifications of the first embodiment will now be described. In a modification of FIG. 16, the plurality of permanent magnets 17 and an annular magnetic material 28 are embedded in shroud 12. The plurality of permanent magnets 17 are arranged with a gap therebetween at equiangular intervals along a single circle such that adjacent magnetic polarities are different from each other. Magnetic material 28 serves as a back yoke of the plurality of permanent magnets 17. In other words, permanent magnet 17 having the N-pole oriented to diaphragm 6 and permanent magnet 17 having the S-pole oriented to diaphragm 6 are alternately arranged with a gap therebetween at equiangular intervals along a single circle. A surface of permanent magnet 17 opposite to a surface closer to diaphragm 6 is attracted to a surface of annular magnetic material 28 by a magnetic force, so that the plurality of permanent magnets 17 are magnetically coupled to magnetic material 28. Thus, a magnetic field around the surfaces of permanent magnets 17 closer to diaphragm 6 is stronger than in the first embodiment. Accordingly, the rotational torque of impeller 10 can be increased while maintaining small device dimensions. Further, copper loss that occurs in coils 20 can be reduced, thereby enhancing energy efficiency in driving impeller 10 to rotate.

Figure 17:
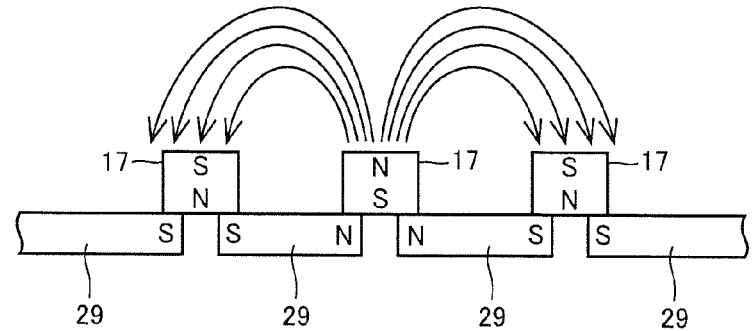
FIG. 17 shows another modification of the first embodiment.

In a modification of FIG. 17, the plurality of permanent magnets 17 and a plurality of permanent magnets 29 are embedded in shroud 12. The number of permanent magnets 29 is equal to the number of permanent magnets 17. The plurality of permanent magnets 29 are provided on the side of the plurality of permanent magnets 17 opposite to the side closer to diaphragm 6, and are aligned in a rotation direction of impeller 10 along the plurality of permanent magnets 17. Each permanent magnet 29 is provided correspondingly to a gap between every two adjacent permanent magnets 17 to cover the corresponding gap from the side opposite to diaphragm 6, and is magnetized in the rotation direction of impeller 10. Each magnetic polarity of each permanent magnet 29 is identical to an adjacent magnetic polarity of permanent magnet 29, and is different from a corresponding magnetic polarity of permanent magnet 17. Each permanent magnet 29 is attracted to two corresponding permanent magnets 17 by a magnetic force, so that the plurality of permanent magnets 17 are magnetically coupled to the plurality of permanent magnets 29. Thus, a magnetic field around the surfaces of permanent magnets 17 closer to diaphragm 6 is stronger than in the modification of FIG. 16. Again, in this modification, the rotational torque of impeller 10 can be increased while maintaining small device dimensions, thereby enhancing energy efficiency in driving impeller 10 to rotate.

Figure 18:
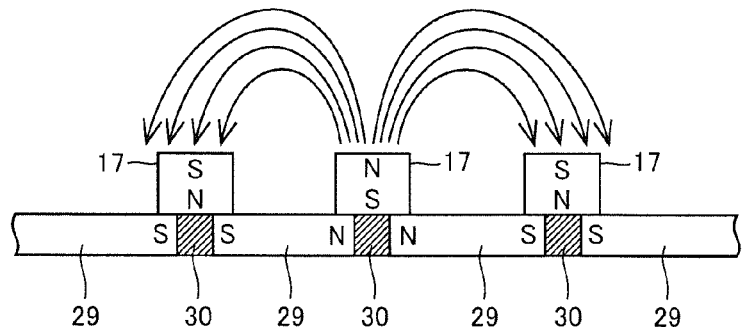
FIG. 18 shows yet another modification of the first embodiment.

As shown in FIG. 18, a magnetic material 30 may be inserted in a gap between every two adjacent permanent magnets 29 and each permanent magnet 17.

Figure 19:
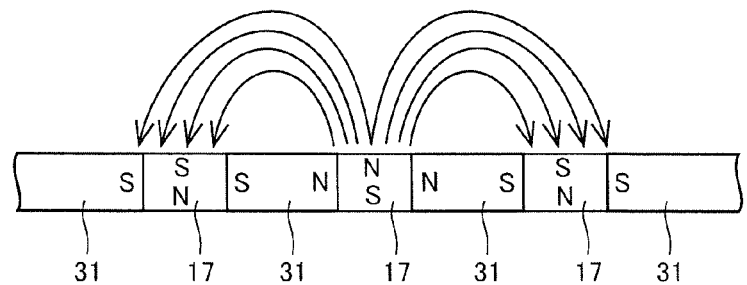
FIG. 19 shows yet another modification of the first embodiment.

In a modification of FIG. 19, the plurality of permanent magnets 17 and a plurality of permanent magnets 31 are embedded in shroud 12. The number of permanent magnets 31 is equal to the number of permanent magnets 17. Permanent magnets 31 are magnetized in a circumferential direction (the rotation direction of impeller 10). Each of the plurality of permanent magnets 17 and each of the plurality of permanent magnets 31 are alternately arranged in the Halbach array at equiangular intervals along a single circle. In other words, permanent magnet 17 having the N-pole oriented to diaphragm 6 and permanent magnet 17 having the S-pole oriented to diaphragm 6 are alternately arranged with a gap therebetween at equiangular intervals along a single circle. The N-pole of each permanent magnet 31 is arranged toward permanent magnet 17 having the N-pole oriented to diaphragm 6, and the S-pole of each permanent magnet 31 is arranged toward permanent magnet 17 having the S-pole oriented to diaphragm 6. The plurality of permanent magnets 17 have the same shape, and the plurality of permanent magnets 31 have the same shape. Permanent magnets 17 and permanent magnets 31 may have the same shape or different shapes. In this modification, an attractive force between permanent magnets 17 and magnetic materials 18 can be suppressed and a magnetic flux that causes torque can be increased, thereby minimizing the permanent magnets. Namely, the weight of impeller 10 can be minimized, and energy efficiency can be enhanced even with a wide motor gap.

Figure 20:
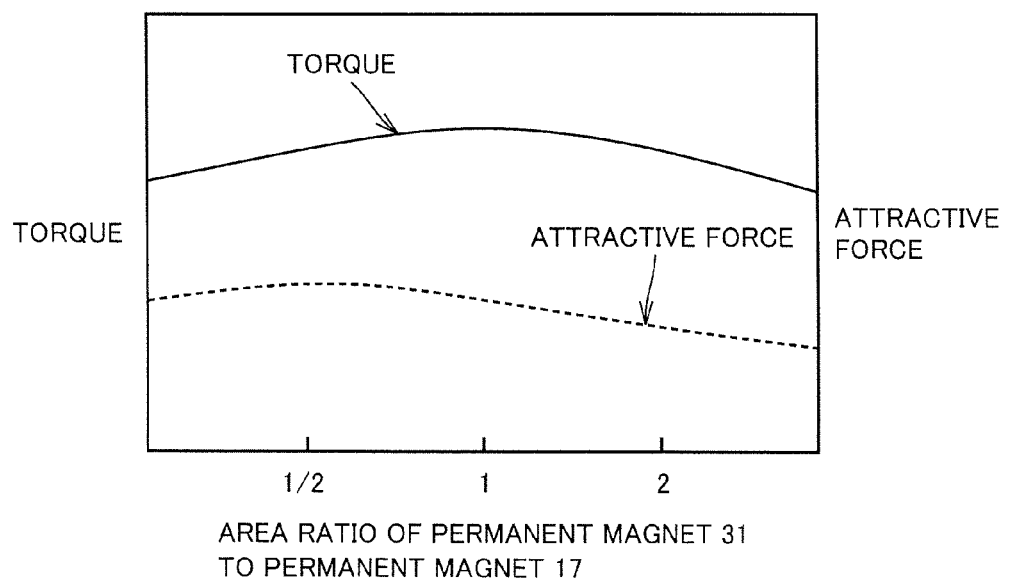
FIG. 20 shows an optimal range of an area ratio of a permanent magnet 31 to a permanent magnet 17 shown in FIG. 19.

Furthermore, with a ratio between a surface area of permanent magnet 17 facing diaphragm 6 and a surface area of permanent magnet 31 facing diaphragm 6, the attractive force between permanent magnets 17 and magnetic materials 18 and the magnetic flux that causes torque can be adjusted. FIG. 20 illustrates relation between the attractive force and generated torque, when permanent magnets 17 and permanent magnets 31 have the same total weight, and an area ratio of permanent magnet 31 to permanent magnet 17 is changed. As shown in FIG. 20, when the area ratio of permanent magnet 31 to permanent magnet 17 is set in a range from ½ or more and 2 or less, the rotational torque of impeller 10 can be increased while suppressing the attractive force between permanent magnets 17 and magnetic materials 18 to low level. Therefore, an optimal range of the area ratio of permanent magnet 31 to permanent magnet 17 is between ½ or more and 2 or less.

In general, when the Halbach array is used for the purpose of reducing a torque ripple of a motor, an area ratio between permanent magnet 17 and permanent magnet 31 is set to about 5:1 to 3:1. In the present invention, when the motor gap is wide, the area ratio between permanent magnet 17 and permanent magnet 31 can be optimized by being set in a range from 2:1 to 1:2 depending on motor dimensions and the motor gap, in order to strengthen the magnetic field.

Figure 21:
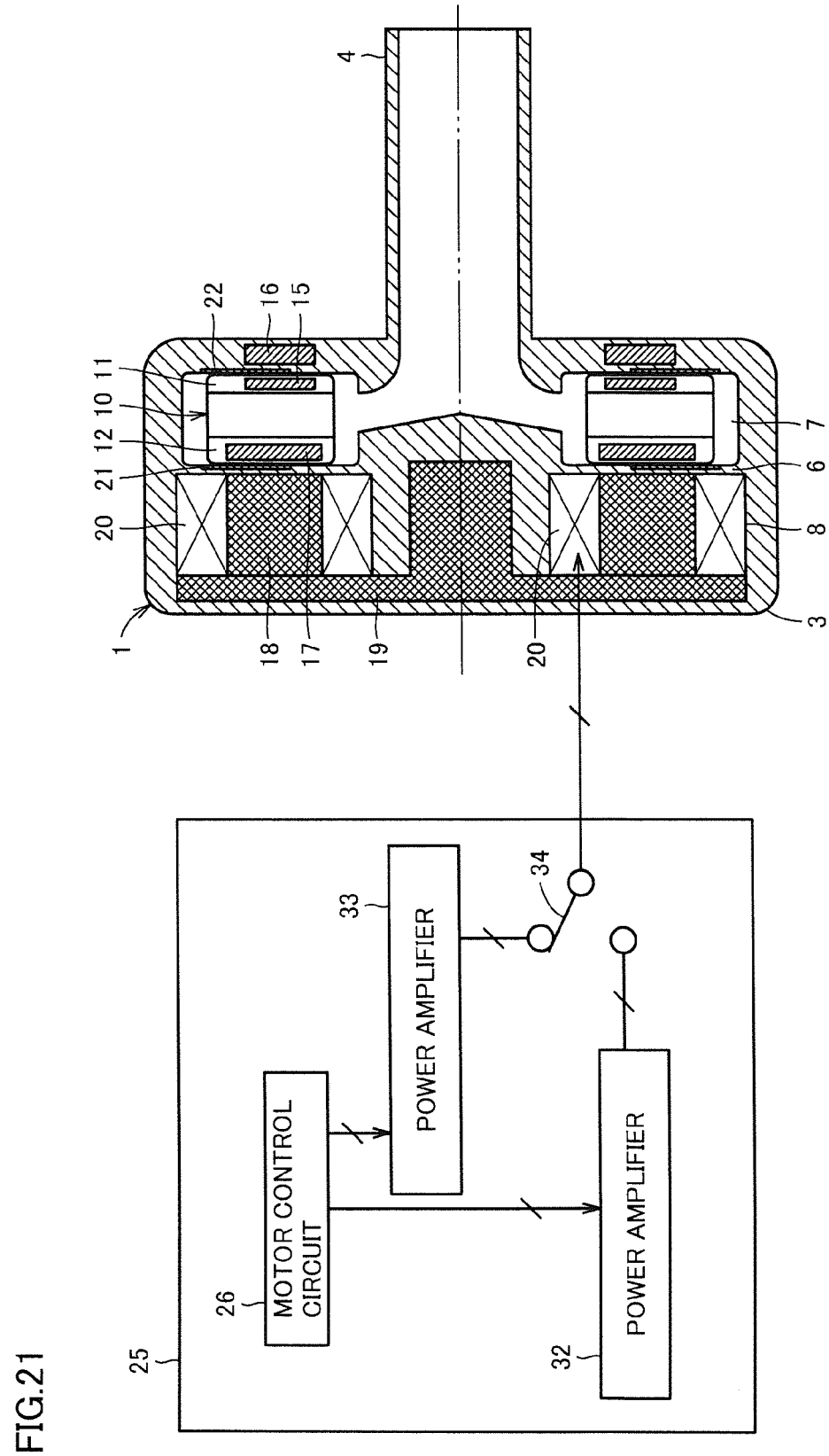
FIG. 21 is a block diagram showing yet another modification of the first embodiment.

FIG. 21 is a block diagram showing yet another modification of the first embodiment. This figure shows an example of a structure where power source supply is switched between during activation of the impeller for rotation and the remaining period. Referring to FIG. 21, in this modification, power amplifier 27 in FIG. 11 is replaced with power amplifiers 32, 33 and a switch 34. Between time t0 and t1 in FIG. 12, an output signal from motor control circuit 26 is provided to power amplifier 32, and an output voltage from power amplifier 32 is applied to coils 20 via switch 34, causing current I0 to flow through coils 20. After time t2, an output signal from motor control circuit 26 is provided to power amplifier 33, and an output voltage from power amplifier 33 is applied to coils 20 via switch 34, causing a current to flow through coils 20.

Figure 22:
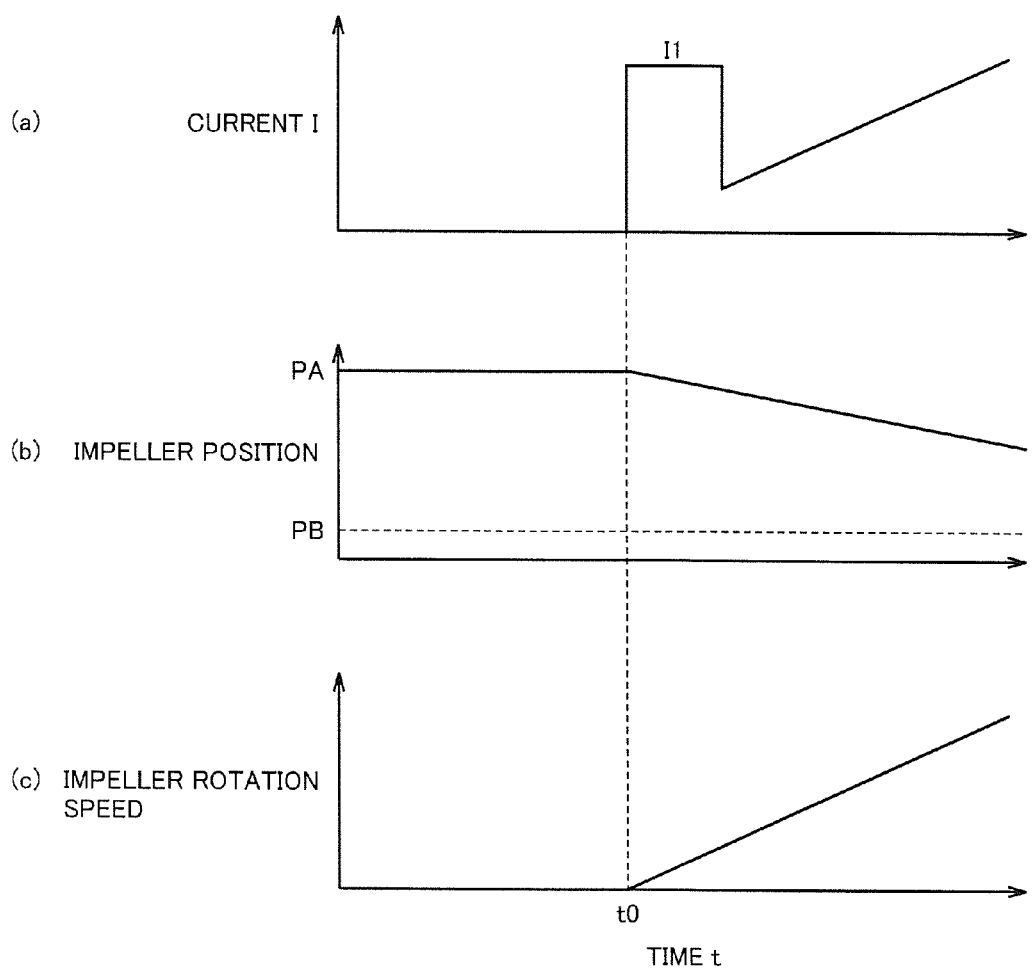
FIG. 22 is a time chart illustrating yet another modification of the first embodiment.

FIG. 22 (a) to (c) are time charts illustrating another modification of the first embodiment. Referring to FIG. 22 (a) to (c), in an initial state, shroud 11 of impeller 10 is in contact with the inner wall of blood chamber 7, and impeller 10 is in position PA. At time t0, a predetermined current I1 is fed through coils 20. Motor control circuit 26 outputs three-phase control signals in the power distribution system shifted by 120 degrees, for example. Power amplifier 27 amplifies the three-phase control signals from motor control circuit 26, and generates three-phase voltages VU, VV and VW shown in FIG. 8. Three-phase voltages VU, VV and VW are applied to first to third coils 20 described with reference to FIG. 7, respectively. Accordingly, a rotating magnetic field is applied to impeller 10 by current I1. Current I1 is larger than current I0 in FIG. 12, and can activate impeller 10 to rotate even when shroud 11 of impeller 10 is in contact with the inner wall of blood chamber 7. After activation for rotation is confirmed, coil current I is reduced, and gradually increased to the predetermined rated value. In this manner, even when impeller 10 is closer to position PA, an overcurrent may be fed through coils 20 only when activating impeller 10 to rotate.

In addition, a diamond-like carbon (DLC) coating may be formed on at least one of the surface of the inner wall of blood chamber 7 and the surface of diaphragm 6, and the surface of impeller 10. As a result, a frictional force between impeller 10, and the inner wall of blood chamber 7 and diaphragm 6 can be reduced to smoothly activate the impeller to rotate. A fluorine-based resin coating, a paraxylylene-based resin coating or the like may be formed instead of the diamond-like carbon coating.

Figure 23:
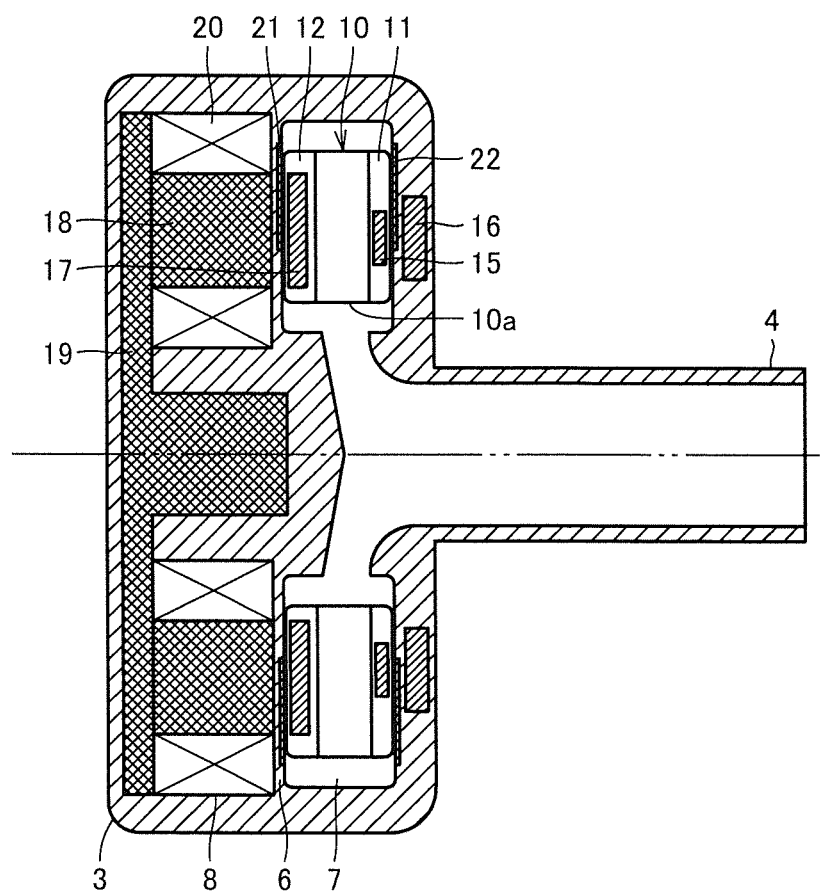
FIG. 23 is a cross-sectional view showing yet another modification of the first embodiment.

FIG. 23 is a cross-sectional view showing yet another modification of the first embodiment, which is compared to FIG. 3. Referring to FIG. 23, in this modification, the opposite surfaces of permanent magnets 15 and 16 have different sizes. While the opposite surfaces of permanent magnets 15 and 16 have the same size in FIG. 3, by making the opposite surfaces of permanent magnets 15 and 16 have different sizes, the amount of change in attractive force which varies with a distance between the magnets, namely, the negative rigidity can be suppressed to low level, thereby preventing reduction in supporting rigidity for impeller 10.

Figure 24:
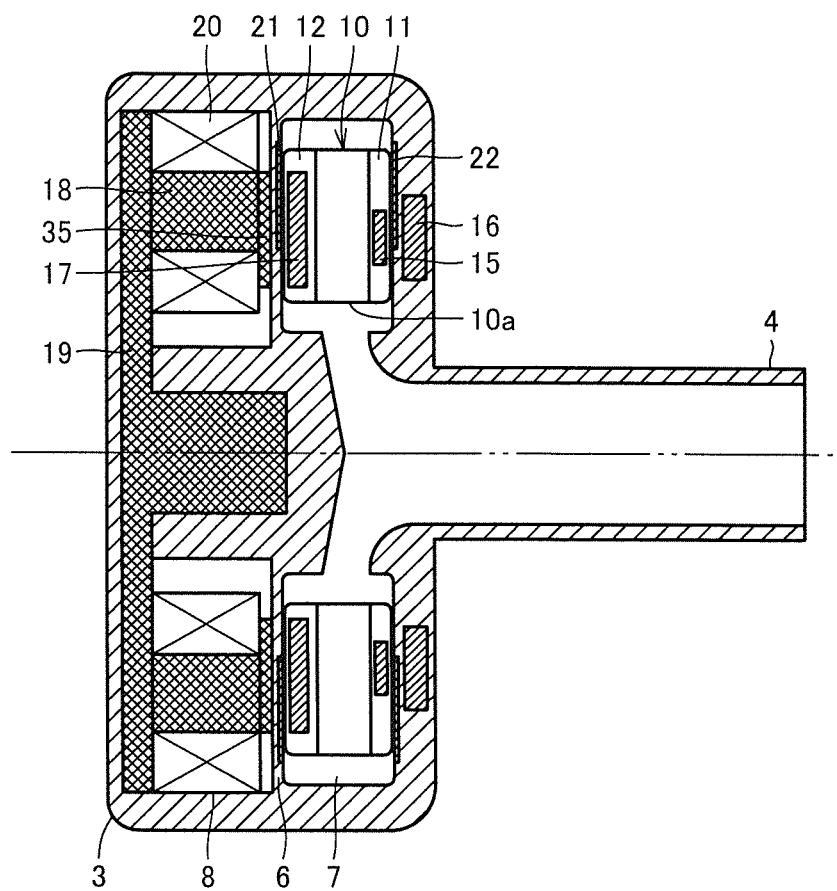
FIG. 24 is a cross-sectional view showing yet another modification of the first embodiment.

FIG. 24 is a cross-sectional view showing yet another modification of the first embodiment, which is compared to FIG. 23. Referring to FIG. 24, in this modification, a magnetic material 35 is provided on a tip surface of each magnetic material 18 facing permanent magnet 17. A surface of magnetic material 35 facing permanent magnet 17 has an area larger than an area of the tip surface of magnetic material 18. In this modification, an attractive force of magnetic materials 18 and 35 on permanent magnet 17 can be increased, thereby enhancing energy efficiency in driving impeller 10 to rotate.

Figure 25:
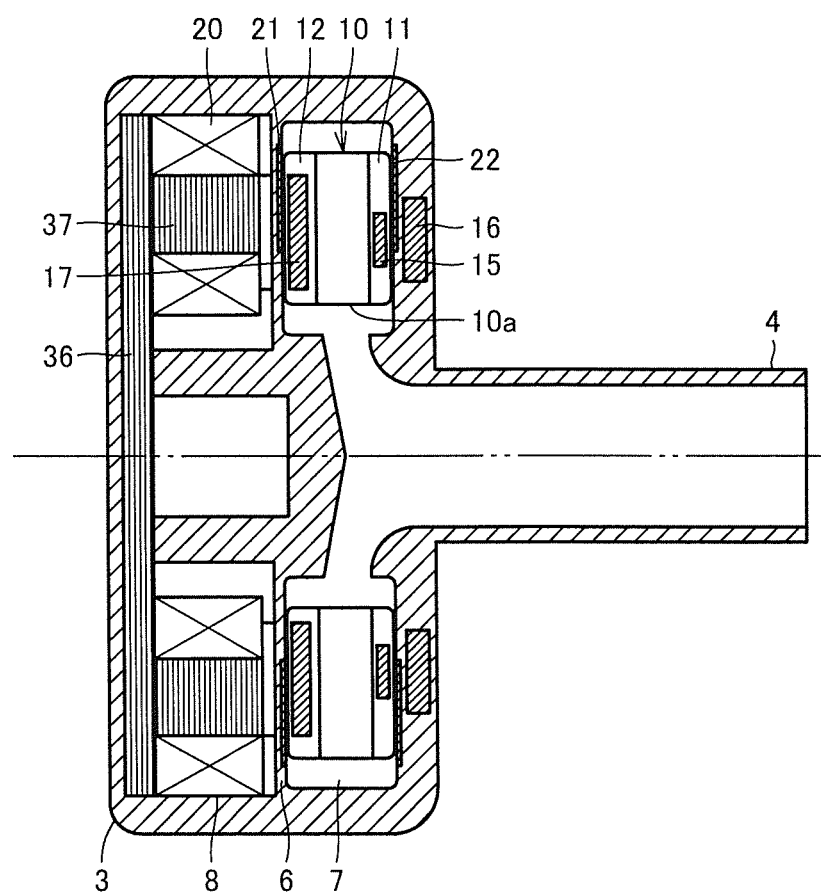
FIG. 25 is a cross-sectional view showing yet another modification of the first embodiment.

FIG. 25 is a cross-sectional view showing yet another modification of the first embodiment, which is compared to FIG. 23. Referring to FIG. 25, in this modification, yoke 19 is replaced with a yoke 36, and magnetic material 18 is replaced with a magnetic material 37. Yoke 36 and magnetic material 37 each include a plurality of steel plates stacked in a length direction of a rotation axis of impeller 10. In this modification, eddy current loss that occurs in yoke 36 and magnetic material 37 can be reduced, thereby enhancing energy efficiency in driving impeller 10 to rotate.

Figure 26:
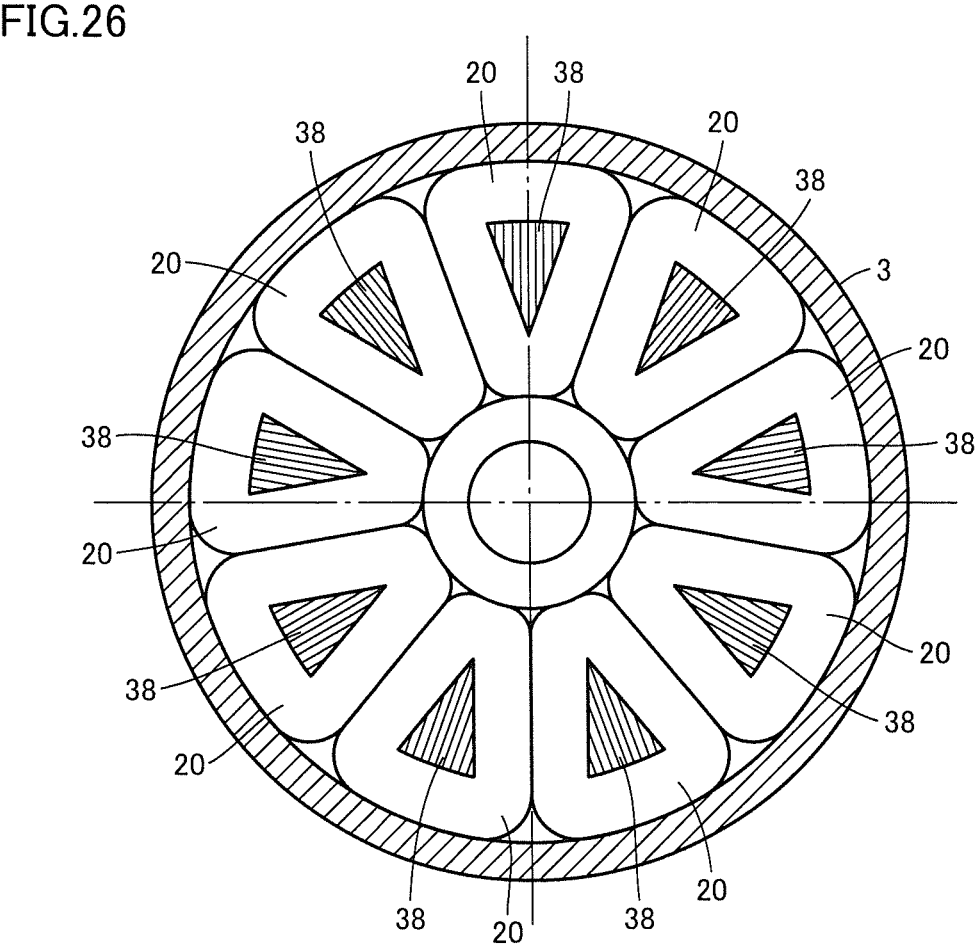
FIG. 26 is a cross-sectional view showing yet another modification of the first embodiment.
Figure 27:
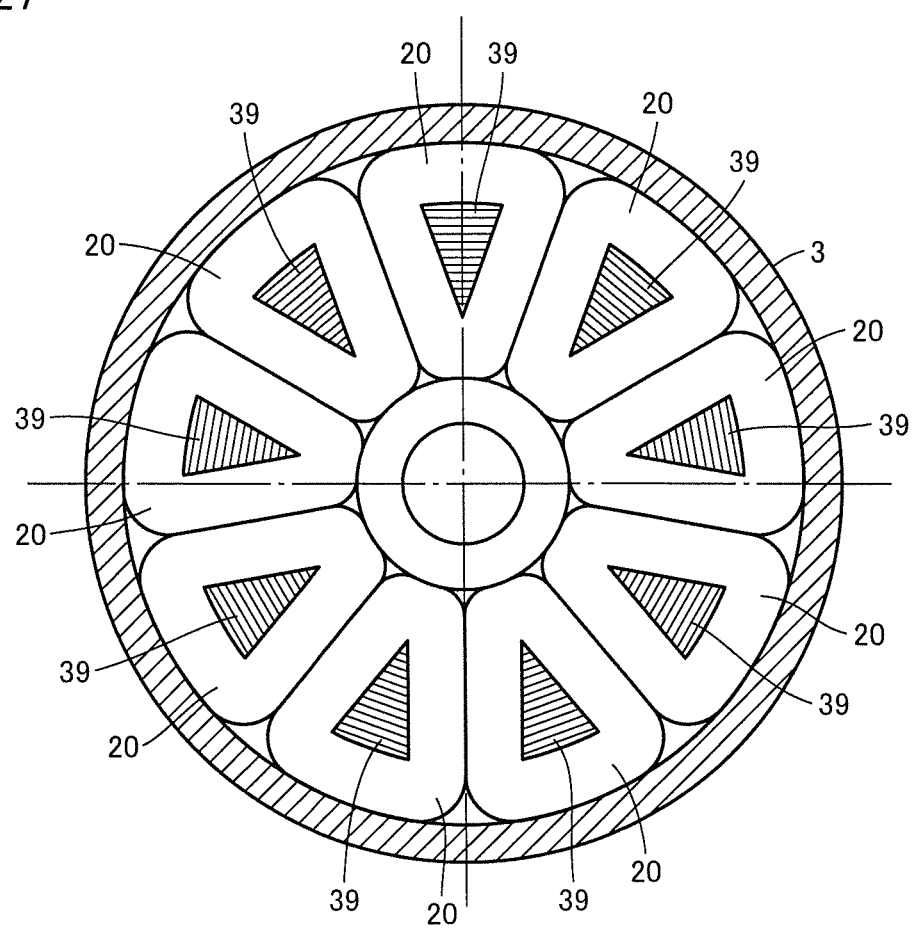
FIG. 27 is a cross-sectional view showing yet another modification of the first embodiment.

Alternatively, as shown in FIG. 26, magnetic material 37 may be replaced with a magnetic material 38 including a plurality of steel plates stacked in the rotation direction of impeller 10. Alternatively, as shown in FIG. 27, magnetic material 37 may be replaced with a magnetic material 39 including a plurality of steel plates stacked in the radial direction of impeller 10. The same effect as in the modification in FIG. 25 can be obtained in these cases as well.

Alternatively, each of yoke 19 and magnetic material 18 in FIG. 3 may be made of powders of pure iron, soft iron, or ferrosilicon. In this case, iron loss in yoke 19 and magnetic material 18 can be reduced, thereby enhancing energy efficiency in driving impeller 10 to rotate.

Figure 28:
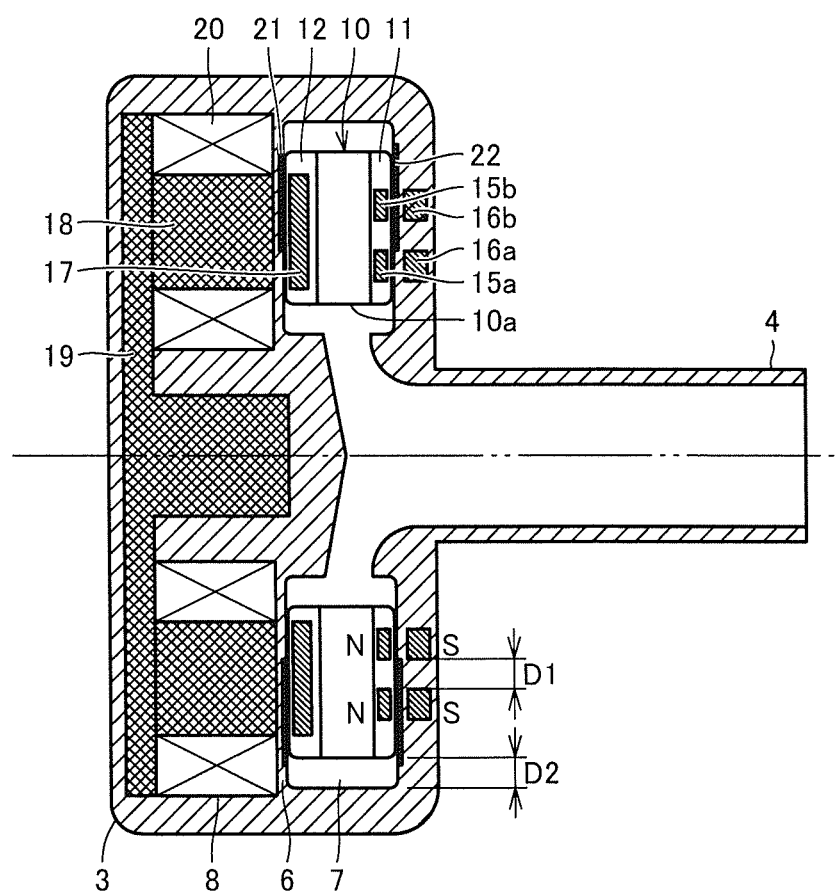
FIG. 28 is a cross-sectional view showing yet another modification of the first embodiment.

FIG. 28 is a cross-sectional view showing yet another modification of the first embodiment, which is compared to FIG. 3. Referring to FIG. 28, in this modification, permanent magnet 15 is radially divided into two permanent magnets 15a and 15b, and permanent magnet 16 is radially divided into two permanent magnets 16a and 16b. That is, permanent magnets 15a and 15b are embedded in shroud 11, and permanent magnets 16a and 16b for attracting permanent magnets 15a and 15b, respectively, are embedded in the inner wall of blood chamber 7 facing shroud 11. Permanent magnets 15a, 15b, 16a and 16b are provided to attract (in other words, bias) impeller 10 to the side opposite to motor chamber 8, namely, toward blood inlet port 4.

Figure 29:
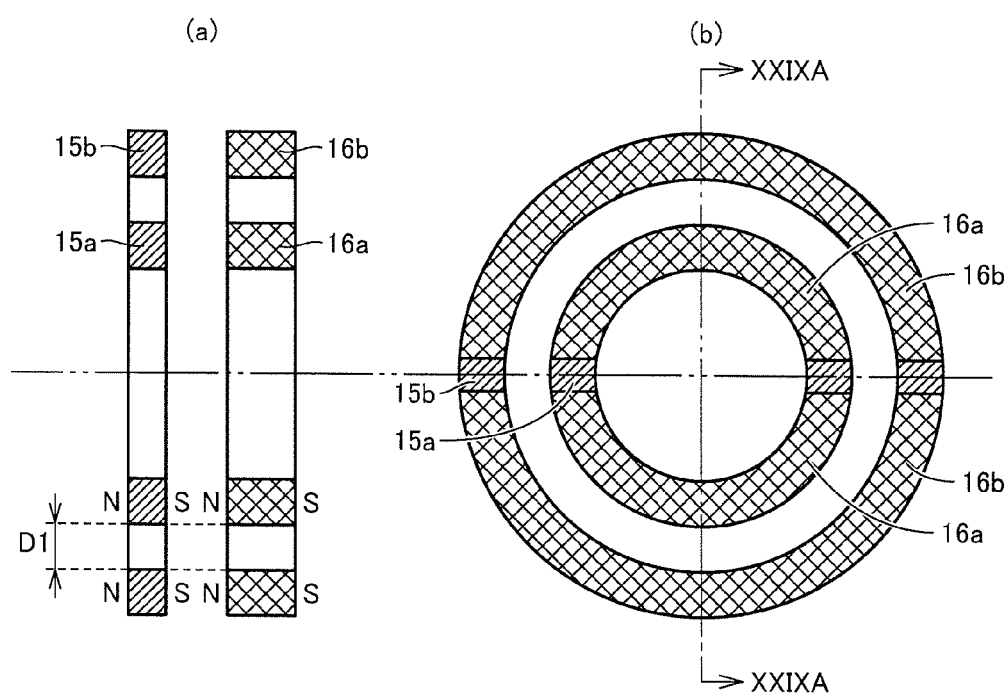
FIG. 29 shows a permanent magnet shown in FIG. 28.

FIG. 29 (a) and (b) show structures of permanent magnets 15a, 15b, 16a and 16b, and FIG. 29 (a) is a cross-sectional view along the line XXIXA-XXIXA in FIG. 29 (b). As shown in FIG. 29 (a) and (b), each of permanent magnets 15a and 15b is formed in an annular shape, and an outer diameter of permanent magnet 15a is smaller than an inner diameter of permanent magnet 15b. Permanent magnets 15a and 15b are coaxially provided, with center points of both permanent magnets 15a and 15b being arranged on a rotation center line of impeller 10. Permanent magnets 15a and 15b have the N-poles oriented in the same direction.

On the other hand, each of permanent magnets 16a and 16b is formed in an arc shape, and two permanent magnets 16a and two permanent magnets 16b are aligned in the rotation direction of impeller 10. An outer diameter and an inner diameter of two permanent magnets 16a arranged in an annular shape are equal to the outer diameter and the inner diameter of permanent magnet 15a. An outer diameter and an inner diameter of two permanent magnets 16b arranged in an annular shape are equal to the outer diameter and the inner diameter of permanent magnet 15b. Permanent magnets 16a and 16b have the N-poles oriented in the same direction. The S-poles of permanent magnets 15a and 15b face the N-poles of permanent magnets 16a and 16b, respectively.

As shown in FIG. 28, a gap D1 between permanent magnets 15a and 15b (i.e., a gap between permanent magnets 16a and 16b) is set to be larger than a distance D2 which is half the radially movable distance of impeller 10 (i.e., a distance which is the difference between an inner diameter of blood chamber 7 and an outer diameter of impeller 10) (D1>D2). This is because, if D1<D2 is satisfied and when impeller 10 moves to a radial maximum position, permanent magnets 15a and 16b, and permanent magnets 15b and 16a interfere with each other, respectively, causing a restoring force for restoring impeller 10 to the central position of the pump to be unstable.

Since the two pairs of permanent magnets 15a, 16a and permanent magnets 15b, 16b are provided in the radial direction of impeller 10 in this manner, the radial supporting rigidity for impeller 10 can be increased as compared to an example where only one pair of permanent magnets is provided in the radial direction of impeller 10.

Instead of providing permanent magnets 15a, 15b and permanent magnets 16a, 16b in shroud 11 and in the inner wall of blood chamber 7, respectively, a permanent magnet may be provided in one of shroud 11 and the inner wall of blood chamber 7, and a magnetic material may be provided in the other. Either a soft magnetic material or a hard magnetic material may be used as the magnetic material.

While the opposite surfaces of permanent magnets 15a and 16a have the same size and the opposite surfaces of permanent magnets 15b and 16b have the same size in FIG. 28, it is preferable that the opposite surfaces of permanent magnets 15a and 16a have different sizes and the opposite surfaces of permanent magnets 15b and 16b have different sizes in order to prevent reduction in rigidity for impeller 10 resulting from the attractive force between permanent magnets 15a, 15b and permanent magnets 16a, 16b. By making the opposite surfaces of permanent magnets 15a, 15b and 16a, 16b have different sizes, the amount of change in attractive force which varies with a distance between the magnets, namely, the negative rigidity can be suppressed to low level, thereby preventing reduction in supporting rigidity for impeller 10.

Moreover, while each of permanent magnets 15a and 15b is formed in an annular shape and each of permanent magnets 16a and 16b is formed in an arc shape, with two permanent magnets 16a and two permanent magnets 16b being aligned at equiangular intervals in the rotation direction of impeller 10 in FIG. 29 (a) and (b), conversely, each of permanent magnets 16a and 16b may be formed in an annular shape and each of permanent magnets 15a and 15b may be formed in an arc shape, with two permanent magnets 15a and two permanent magnets 15b being aligned at equiangular intervals in the rotation direction of impeller 10. Alternatively, each of permanent magnets 15a and 15b or each of permanent magnets 16a and 16b may be formed in a shorter arc shape, and a plurality of them may be aligned at equiangular intervals in the rotation direction of impeller 10.

[Second Embodiment]

Figure 30:
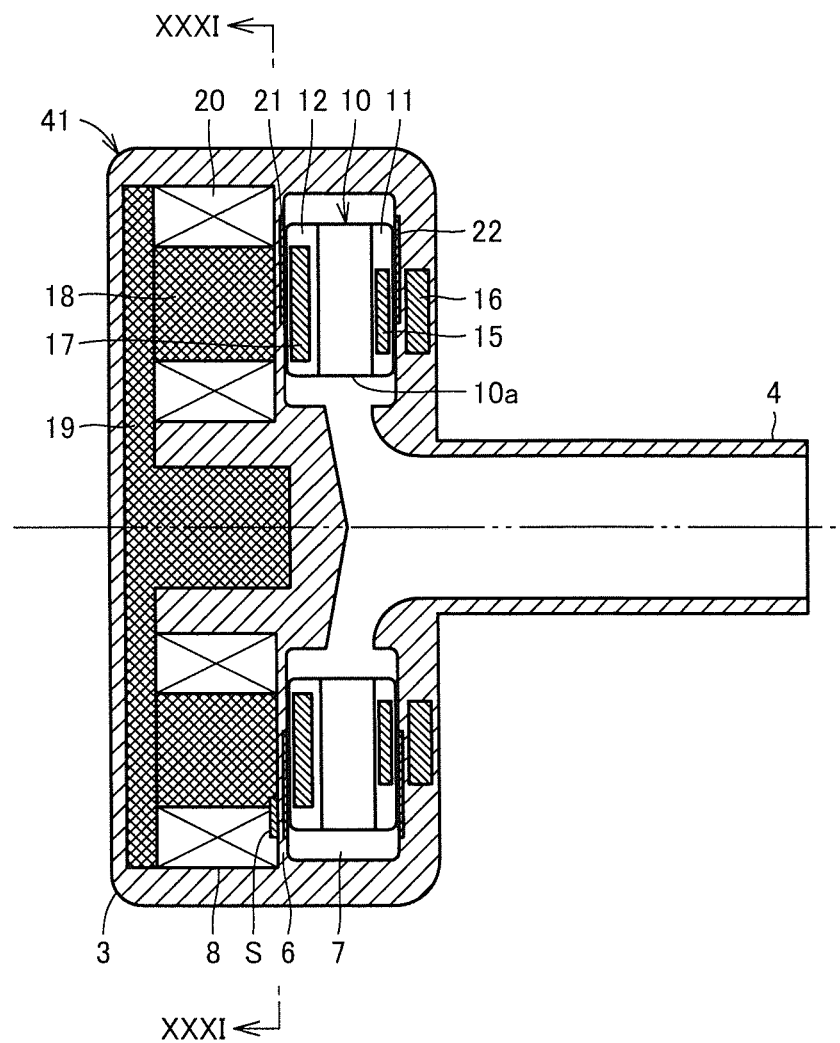
FIG. 30 is a cross-sectional view showing a structure of a pump unit of a centrifugal blood pump apparatus according to a second embodiment of the present invention.
Figure 31:
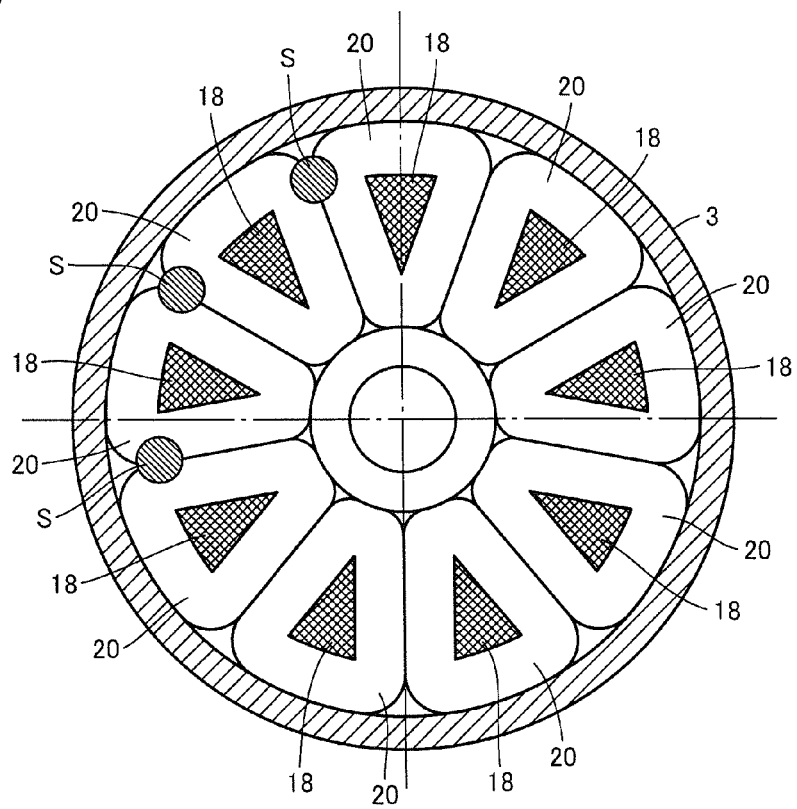
FIG. 31 is a cross-sectional view along the line XXXI-XXXI in FIG. 30.

FIG. 30 is a cross-sectional view showing a structure of a pump unit 41 of a centrifugal blood pump apparatus according to a second embodiment of the present invention, which is compared to FIG. 3. FIG. 31 is a cross-sectional view along the line XXXI-XXXI in FIG. 30, which is compared to FIG. 7.

Figure 32:
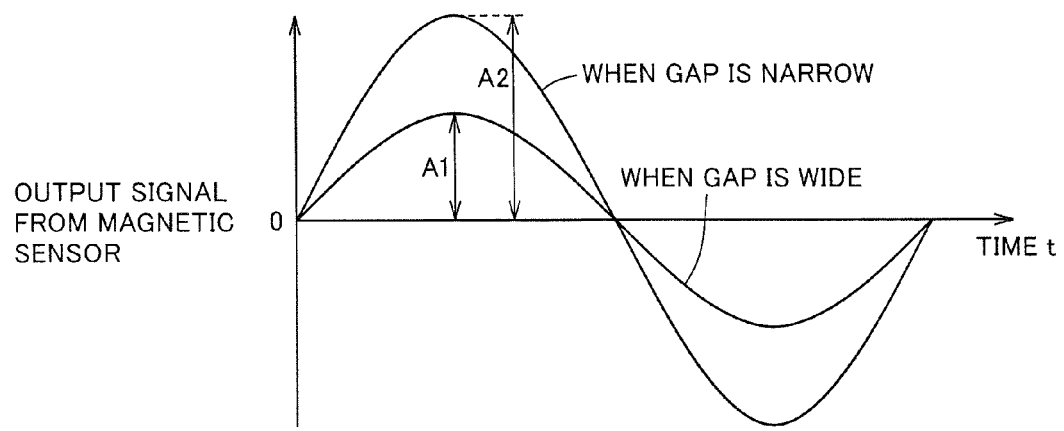
FIG. 32 is a time chart illustrating an output signal from a magnetic sensor shown in FIG. 31.

Referring to FIGS. 30 and 31, pump unit 41 is different from pump unit 1 in the first embodiment in that three magnetic sensors S are provided in three portions among four adjacent magnetic materials 18 out of nine magnetic materials 18. Three magnetic sensors S are arranged to face a path through which the plurality of permanent magnets 17 in impeller 10 pass. When impeller 10 rotates and the S-pole and the N-pole of the plurality of permanent magnets 17 alternately pass near magnetic sensor S, level of an output signal from magnetic sensor S sinusoidally varies as shown in FIG. 32. Accordingly, by detecting temporal variation in output signal from magnetic sensor S, positional relation between the plurality of permanent magnets 17 and the plurality of magnetic materials 18 can be detected, to determine timing for feeding a current through the plurality of coils 20, and a rotation speed of impeller 10.

When a gap between impeller 10 and diaphragm 6 is wide, a magnetic field near magnetic sensor S becomes weaker, and an amplitude A1 of an output signal from magnetic sensor S becomes small. When the gap between impeller 10 and diaphragm 6 is narrow, the magnetic field near magnetic sensor S becomes stronger, and an amplitude A2 of the output signal from magnetic sensor S becomes large. As such, by detecting the amplitude of the output signal from magnetic sensor S, a position of impeller 10 in the movable range of impeller 10 can be detected.

Figure 33:
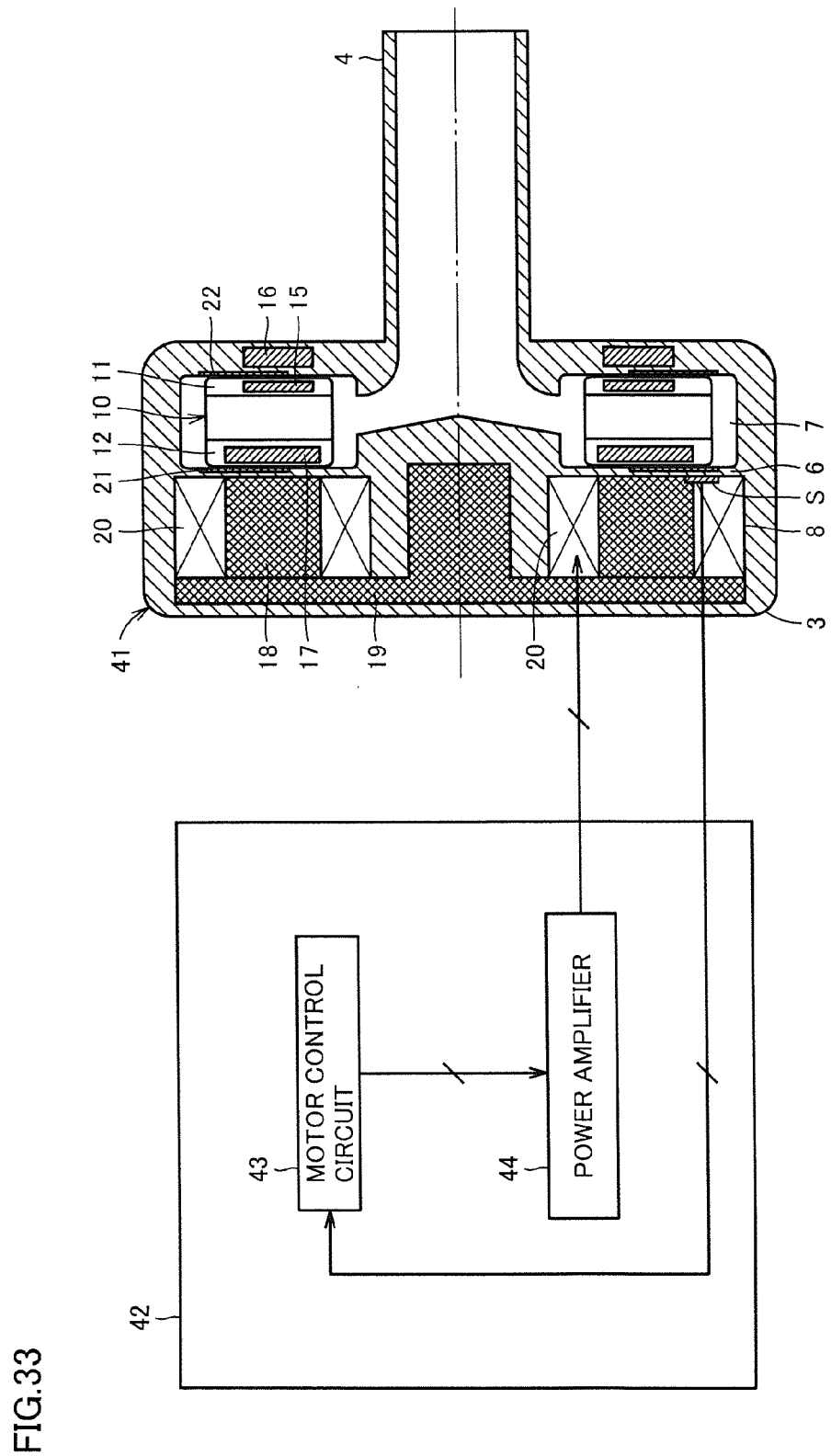
FIG. 33 is a block diagram showing a structure of a controller for controlling the pump unit shown in FIGS. 30 to 32.

FIG. 33 is a block diagram showing a structure of a controller 42 for controlling pump unit 41. In FIG. 33, controller 42 includes a motor control circuit 43 and a power amplifier 44. Motor control circuit 43 outputs three-phase control signals in the power distribution system shifted by 120 degrees, for example, based on output signals from three magnetic sensors S. Power amplifier 44 amplifies the three-phase control signals from motor control circuit 43, and generates three-phase voltages VU, VV and VW shown in FIG. 8. Three-phase voltages VU, VV and VW are applied to first to third coils 20 described with reference to FIGS. 7 and 8, respectively. As a result, during normal operation, impeller 10 rotates with a predetermined rotation speed in the central position of the movable range.

The same effect as in the first embodiment can be obtained in the second embodiment as well.

Figure 34:
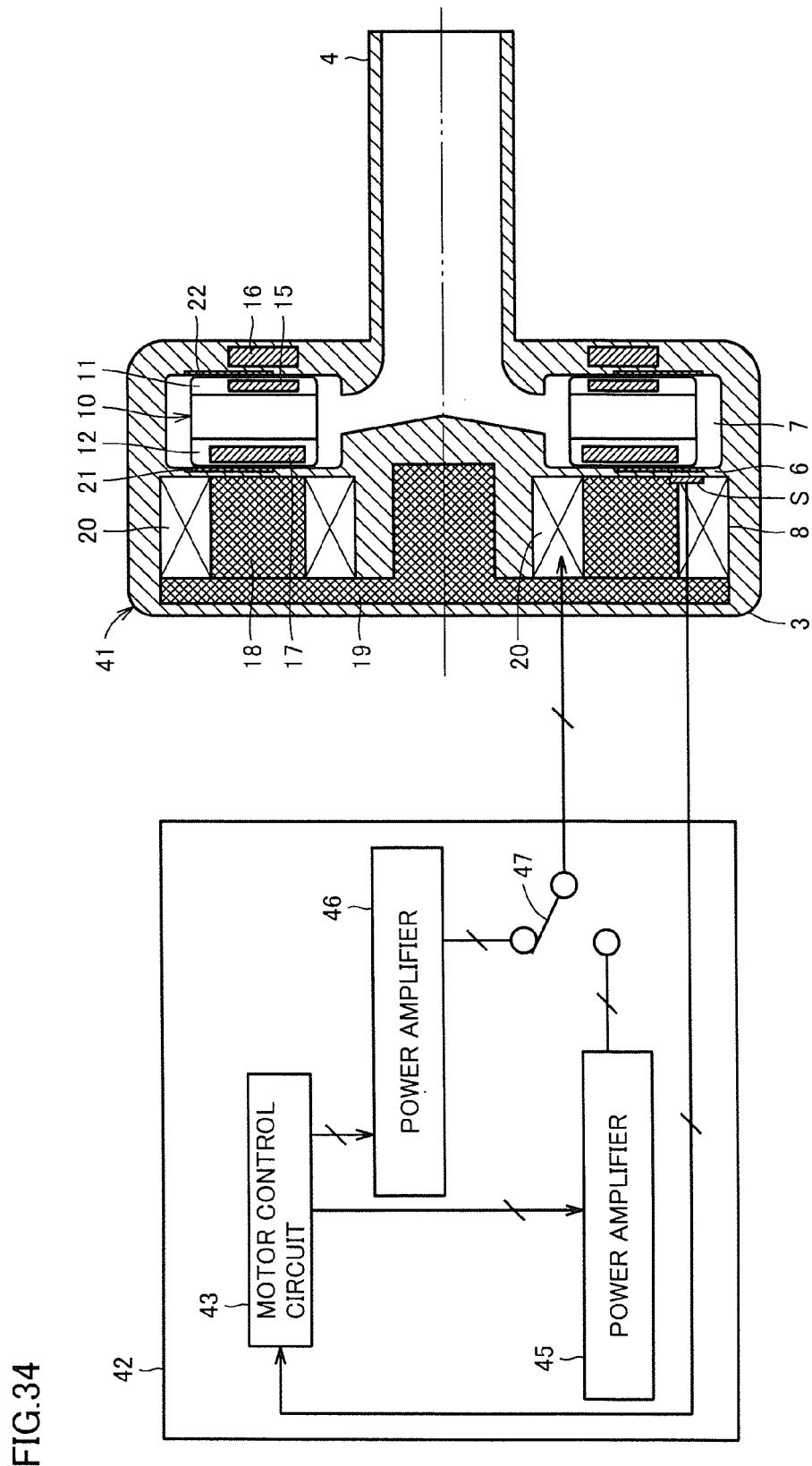
FIG. 34 is a block diagram showing a modification of the second embodiment.

FIG. 34 is a block diagram showing a modification of the second embodiment. This figure shows an example of a structure where power source supply is switched between during activation of the impeller for rotation and the remaining period. Referring to FIG. 34, in this modification, power amplifier 44 in FIG. 33 is replaced with power amplifiers 45, 46 and switch 47. Between time t0 and t1 in FIG. 12, an output signal from motor control circuit 43 is provided to power amplifier 45, and an output voltage from power amplifier 45 is applied to coils 20 via switch 47, causing current I0 to flow through coils 20. After time t2, an output signal from motor control circuit 43 is provided to power amplifier 46, and an output voltage from power amplifier 46 is applied to coils 20 via switch 47, causing a current to flow through coils 20.

Figure 35:
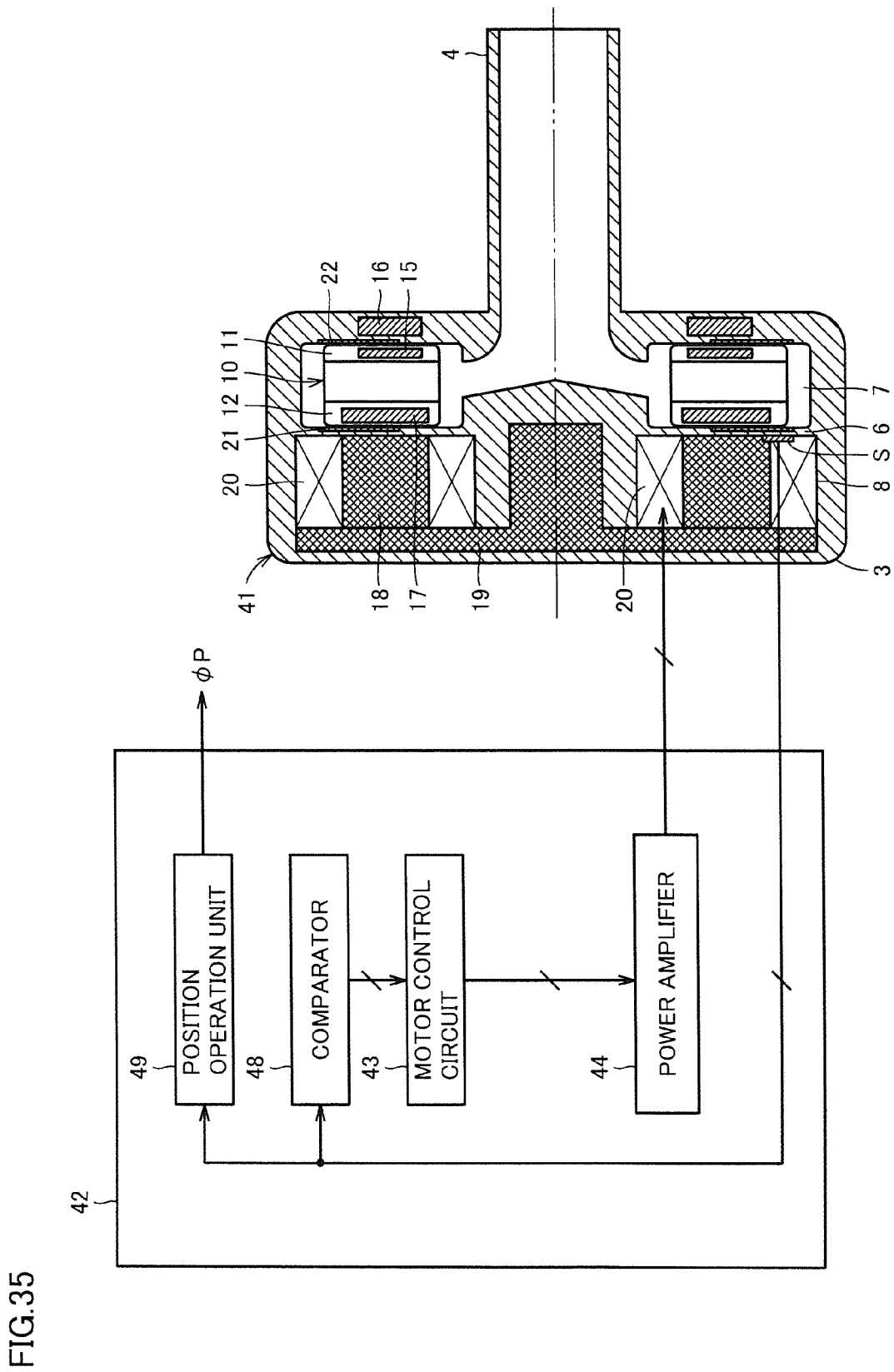
FIG. 35 is a block diagram showing another modification of the second embodiment.

FIG. 35 is a block diagram showing another modification of the second embodiment, which is compared to FIG. 33. In this modification, a comparator 48 and a position operation unit 49 are added into controller 42 in FIG. 33. Comparator 48 generates, based on output signals from three magnetic sensors S, three pulse signal strings which indicate timing when the plurality of permanent magnets 17 in impeller 10 pass near three magnetic sensors S. Motor control circuit 43 generates three-phase control signals in accordance with the three pulse signal strings generated by comparator 48. Power amplifier 44 amplifies the three-phase control signals generated by motor control circuit 43, and generates voltages VU, VV and VW in FIG. 8. Position operation unit 49 determines an axial position of impeller 10 in the movable range of impeller 10 based on the amplitudes of the output signals from three magnetic sensors S, as has been described with reference to FIG. 32, and outputs a signal φP which indicates the determined position. With signal φP, whether or not the position of impeller 10 is within a normal range can be determined.

Figure 36:
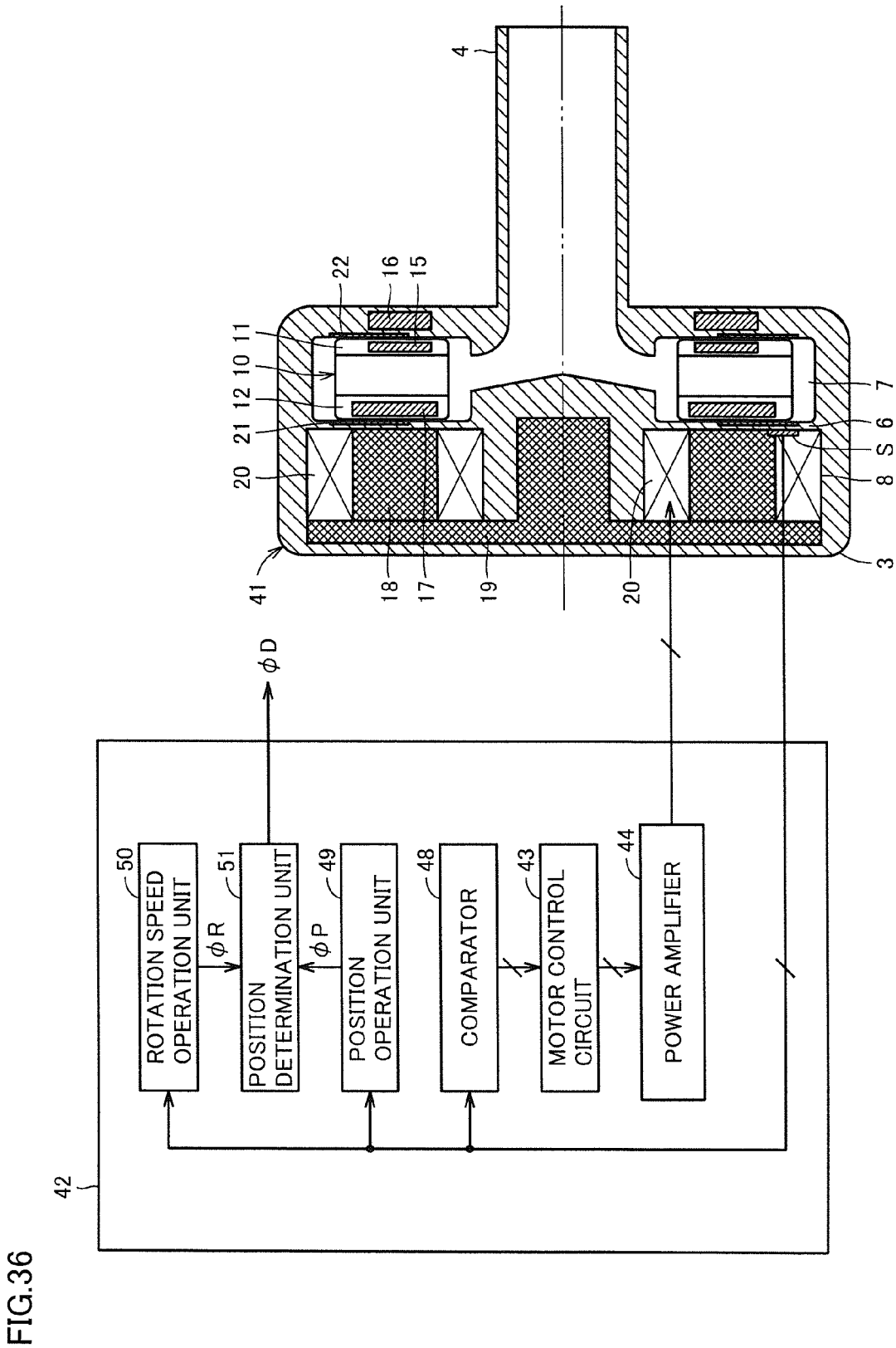
FIG. 36 is a block diagram showing yet another modification of the second embodiment.

FIG. 36 is a block diagram showing yet another modification of the second embodiment, which is compared to FIG. 35. In this modification, a rotation speed operation unit 50 and a position determination unit 51 are added into controller 42 in FIG. 35. Rotation speed operation unit 50 determines a rotation speed of impeller 10 based on output signals from three magnetic sensors S, and outputs a signal φR which indicates the rotation speed. Position determination unit 51 determines whether or not the position of impeller 10 is within the normal range based on signal φP which indicates the position of impeller 10 generated by position operation unit 49 and signal φR which indicates the rotation speed of impeller 10 generated by rotation speed operation unit 50, and outputs a signal φD which indicates a determination result. The reason for referring to the rotation speed of impeller 10 during determination is that the hydrodynamic bearing effect of grooves for hydrodynamic bearing 21 and 22 varies with the rotation speed of impeller 10, causing a change in position of impeller 10. If the rotation speed is fixed, rotation speed operation unit 50 may be removed.

When determining whether or not the position of impeller 10 is within the normal range, viscosity information on liquid (blood in this case) may be referred to instead of or in addition to the rotation speed of impeller 10. This is because the hydrodynamic bearing effect of grooves for hydrodynamic bearing 21 and 22 varies with the viscosity of the liquid, causing a change in position of impeller 10.

When impeller 10 is not rotating in this centrifugal blood pump apparatus, the hydrodynamic bearing effect of grooves for hydrodynamic bearing 21 and 22 is not produced, so that impeller 10 is in contact with the inner wall of housing 2 due to attractive force F1 between permanent magnets 15 and 16 and attractive force F2 between permanent magnet 17 and magnetic material 18. Thus, at the beginning of rotation and during low-speed rotation, impeller 10 does not rotate in a normal axial position. For this reason, when signal φR which indicates the rotation speed is not used for position determination, signal φD output from position determination unit 51 may forcibly act as a signal which indicates that the position of impeller 10 is normal, for a predetermined time period between the beginning of rotation and a time when the rated rotation speed is reached.

Figure 37:
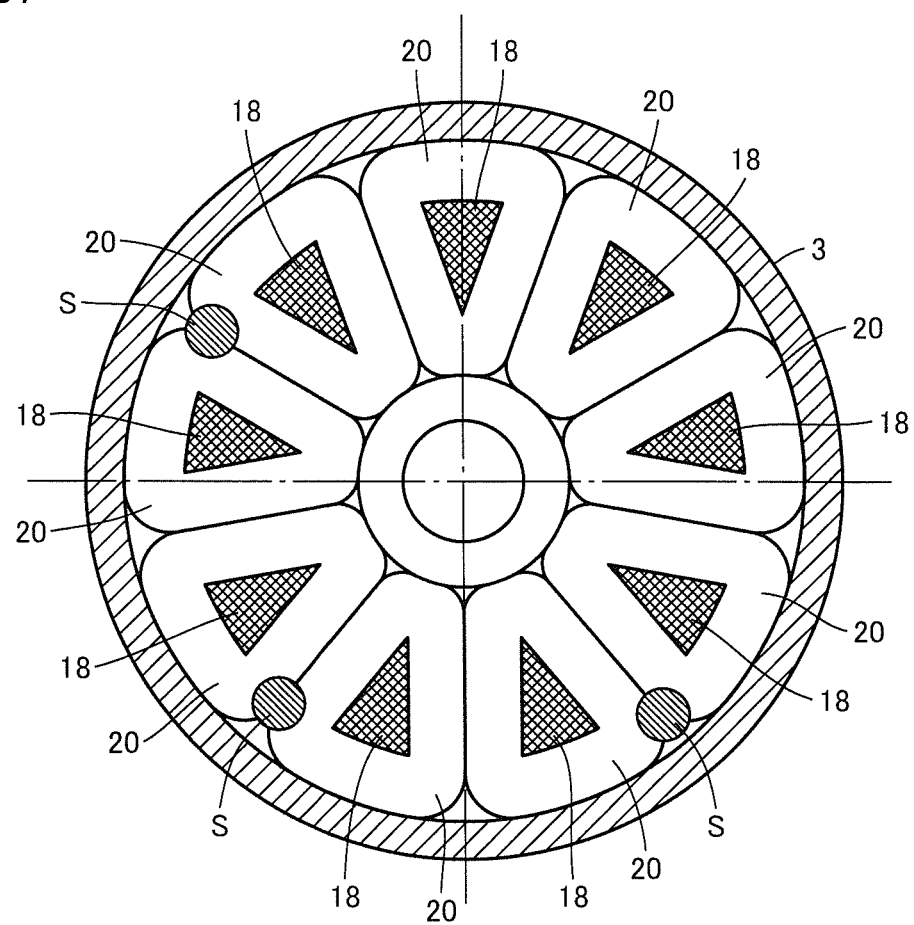
FIG. 37 is a cross-sectional view showing yet another modification of the second embodiment.

FIG. 37 is a cross-sectional view showing yet another modification of the second embodiment, which is compared to FIG. 31. In this modification, nine coils 20 are divided into three groups each including three coils, and voltages VU, VV and VW in FIG. 8 are applied to first to third coils 20 of each group, respectively. First magnetic sensor S is arranged between first and second coils 20 of the first group. Second magnetic sensor S is arranged between third coil 20 of the first group and first coil 20 of the second group. Third magnetic sensor S is arranged between second and third coils 20 of the second group. Accordingly, an electrical angle between two adjacent of first to third magnetic sensors S is kept at 120 degrees. Based on output signals from first to third magnetic sensors S, three-phase control signals can be generated, and an axial position of impeller 10 can be detected. Further, a mechanical angle between two adjacent of first to third magnetic sensors S is 90 degrees, and so a levitation posture of rotating impeller 10 can also be detected.

Figure 38:
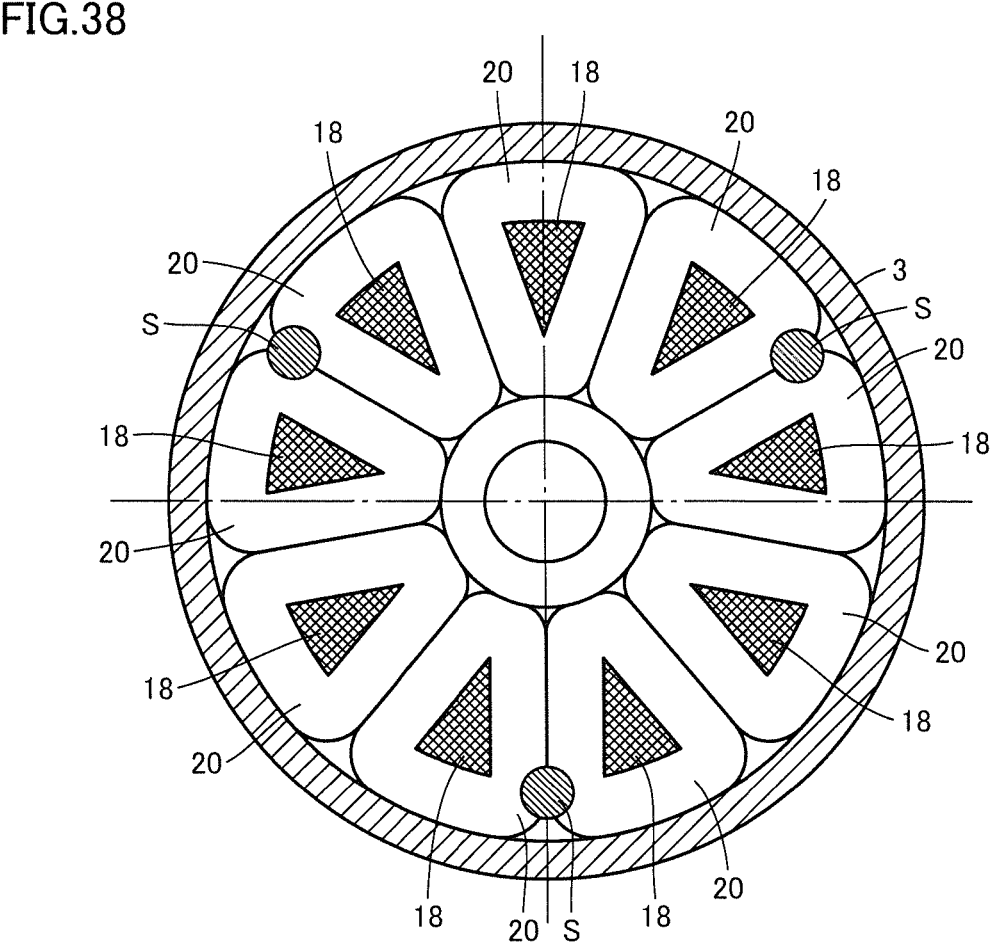
FIG. 38 is a cross-sectional view showing yet another modification of the second embodiment.

FIG. 38 is a cross-sectional view showing yet another modification of the second embodiment, which is compared to FIG. 31. In this modification, nine coils 20 are divided into three groups each including three coils, and three magnetic sensors S are arranged among the three groups, respectively. Accordingly, a mechanical angle between two adjacent of three magnetic sensors S is 120 degrees, allowing easy operation of a levitation posture of rotating impeller 10. Timing for feeding a current through nine coils 20 is operated based on an output signal from any one of three magnetic sensors S.

[Third Embodiment]

FIG. 39 (a) is a bottom view of a rotor 61 of an axial gap type motor according to a third embodiment of the present invention, seen from the side of a diaphragm 60, and FIG. 39 (b) is a front view showing a substantial part of the axial gap type motor.

In FIG. 39 (a) and (b), this axial gap type motor has a structure similar to that of pump unit 1 of the centrifugal blood pump apparatus in the first embodiment, and includes first and second chambers (not shown) partitioned from each other by circular diaphragm 60. The first chamber includes annular rotor 61 rotatably provided along diaphragm 60, and the second chamber includes a stator 70 for driving rotor 61 to rotate with diaphragm 60 interposed therebetween.

Rotor 61 includes an annular support member 62 made of a nonmagnetic material, and a plurality of (e.g., eight) permanent magnets 63 fixed to support member 62. The plurality of permanent magnets 63 are aligned with a gap therebetween in a rotation direction of rotor 61. Each permanent magnet 63 is magnetized in a direction in which a rotation central axis of rotor 61 extends. Two adjacent permanent magnets 63 have magnetic polarities different from each other. Stator 70 includes a plurality of (e.g., six) magnetic materials 71 arranged to face the plurality of permanent magnets 63, and a plurality of coils 72 wound around the plurality of magnetic materials 71, respectively, for generating a rotating magnetic field. The plurality of magnetic materials 71 are fixed to an annular yoke 73. Rotor 61 can be rotated by applying voltages to the plurality of coils 72 by the power distribution system shifted by 120 degrees.

The effect of the third embodiment will now be described. FIG. 40 (a) and (b) show a comparative example of the third embodiment, which are compared to FIG. 39 (a) and (b). Referring to FIG. 40 (a) and (b), this comparative example is different from the third embodiment in that there is no gap between the plurality of permanent magnets 63.

As shown in FIG. 14 (a) and (b), when permanent magnet 63 in the third embodiment and permanent magnet 63 in the comparative example have the same weight, magnetic flux density between permanent magnets 63 and 63 is higher in the third embodiment, and a magnetic field around permanent magnets 63 is stronger in the third embodiment. In the third embodiment, therefore, a magnetic coupling force between permanent magnets 63 in rotor 61 and magnetic materials 71 and coils 72 in stator 70 can be increased. Accordingly, the rotational torque of rotor 61 can be increased while maintaining small device dimensions.

Figure 41:
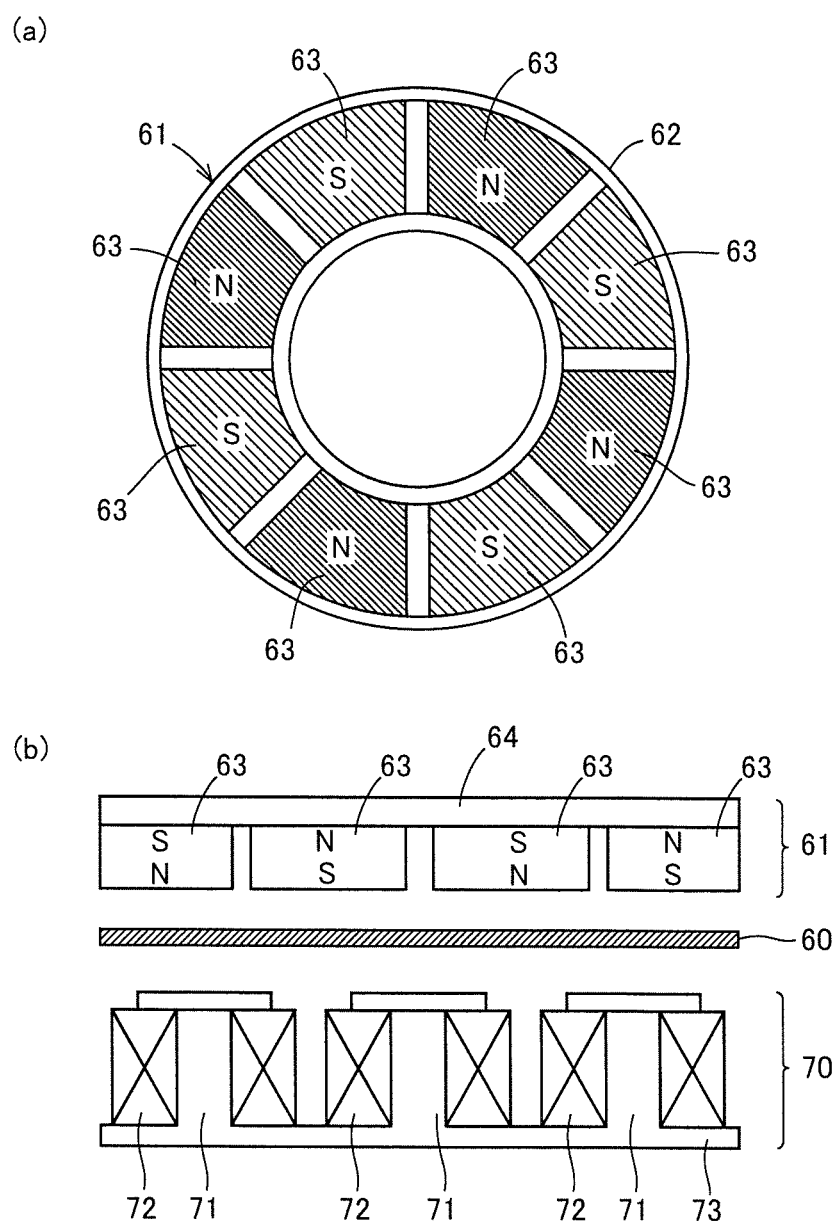
FIG. 41 shows a modification of the third embodiment.

Various modifications of the third embodiment will now be described. In a modification of FIG. 41 (a) and (b), the plurality of permanent magnets 63 and an annular magnetic material 64 are provided in rotor 61. The plurality of permanent magnets 63 are arranged with a gap therebetween at equiangular intervals along a single circle such that adjacent magnetic polarities are different from each other. Magnetic material 64 serves as a back yoke of the plurality of permanent magnets 63. In other words, permanent magnet 63 having the N-pole oriented to diaphragm 60 and permanent magnet 63 having the S-pole oriented to diaphragm 60 are alternately arranged with a gap therebetween at equiangular intervals along a single circle. A surface of permanent magnet 63 opposite to a surface closer to diaphragm 60 is attracted to a surface of annular magnetic material 64 by a magnetic force, so that the plurality of permanent magnets 63 are magnetically coupled to magnetic material 64. Thus, a magnetic field around the surfaces of permanent magnets 63 closer to diaphragm 60 is stronger than in the third embodiment (see FIG. 16). Accordingly, the rotational torque of rotor 61 can be increased while maintaining small device dimensions. Further, copper loss that occurs in coils 72 can be reduced, thereby enhancing energy efficiency in driving rotor 61 to rotate.

Figure 42:
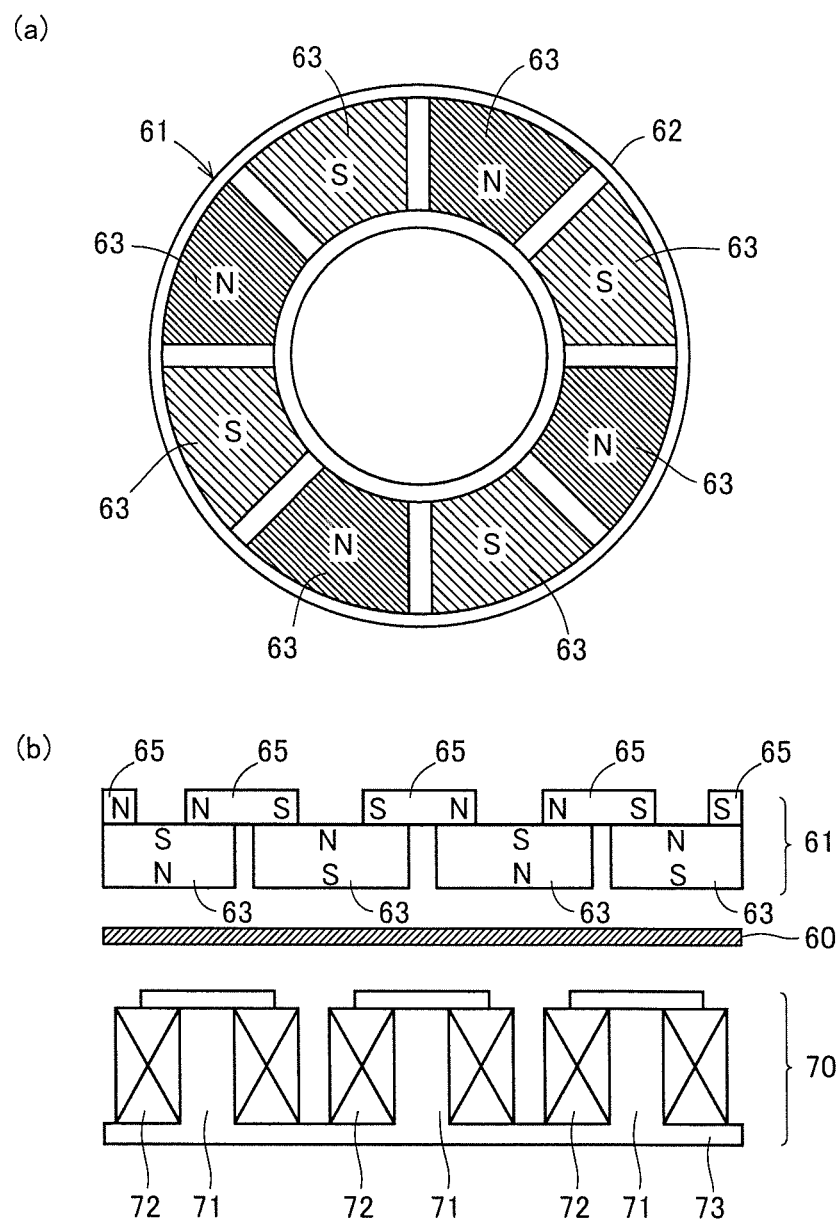
FIG. 42 shows another modification of the third embodiment.

In a modification of FIG. 42 (a) and (b), the plurality of permanent magnets 63 and a plurality of permanent magnets 65 are provided in rotor 61. The number of permanent magnets 65 is equal to the number of permanent magnets 63. The plurality of permanent magnets 65 are provided on the side of the plurality of permanent magnets 63 opposite to the side closer to diaphragm 60, and are aligned in the rotation direction of rotor 61 along the plurality of permanent magnets 63. Each permanent magnet 65 is provided correspondingly to a gap between every two adjacent permanent magnets 63 to cover the corresponding gap from the side opposite to diaphragm 60, and is magnetized in the rotation direction of rotor 61. Each magnetic polarity of each permanent magnet 65 is identical to an adjacent magnetic polarity of permanent magnet 65, and is different from a corresponding magnetic polarity of permanent magnet 63. Each permanent magnet 65 is attracted to two corresponding permanent magnets 63 by a magnetic force, so that the plurality of permanent magnets 63 are magnetically coupled to the plurality of permanent magnets 65. Thus, a magnetic field around the surfaces of permanent magnets 63 closer to diaphragm 60 is stronger than in the modification of FIG. 41 (a) and (b). Again, in this modification, the rotational torque of rotor 61 can be increased while maintaining small device dimensions, thereby enhancing energy efficiency in driving rotor 61 to rotate.

As shown in FIG. 43 (a) and (b), a magnetic material 66 may be inserted in a gap between every two adjacent permanent magnets 65 and each permanent magnet 63 (see FIG. 18).

In a modification of FIG. 44 (a) and (b), the plurality of permanent magnets 63 and a plurality of permanent magnets 67 are provided in rotor 61. The number of permanent magnets 67 is equal to the number of permanent magnets 63. Permanent magnets 67 are magnetized in a circumferential direction (the rotation direction of rotor 61). Each of the plurality of permanent magnets 63 and each of the plurality of permanent magnets 67 are alternately arranged in the Halbach array at equiangular intervals along a single circle. In other words, permanent magnet 63 having the N-pole oriented to diaphragm 60 and permanent magnet 63 having the S-pole oriented to diaphragm 60 are alternately arranged with a gap therebetween at equiangular intervals along a single circle. The N-pole of each permanent magnet 67 is arranged toward permanent magnet 63 having the N-pole oriented to diaphragm 60, and the S-pole of each permanent magnet 67 is arranged toward permanent magnet 63 having the S-pole oriented to diaphragm 60. The plurality of permanent magnets 63 have the same shape, and the plurality of permanent magnets 67 have the same shape. Permanent magnets 63 and permanent magnets 67 may have the same shape or different shapes. In this modification, an attractive force between permanent magnets 63 and magnetic materials 71 can be suppressed and a magnetic flux that causes torque can be increased, thereby minimizing the permanent magnets (see FIG. 19). Namely, the weight of rotor 61 can be minimized, and energy efficiency can be enhanced even with a wide motor gap.

Furthermore, with a ratio between a surface area of permanent magnet 63 facing diaphragm 60 and a surface area of permanent magnet 67 facing diaphragm 60, the attractive force between permanent magnets 63 and magnetic materials 71 and the magnetic flux that causes torque can be adjusted. As shown in FIG. 20, when the area ratio of permanent magnet 67 to permanent magnet 63 is set in a range from ½ or more and 2 or less, the rotational torque of rotor 61 can be increased while suppressing the attractive force between permanent magnets 63 and magnetic materials 71 to low level. Therefore, an optimal range of the area ratio of permanent magnet 67 to permanent magnet 63 is between ½ or more and 2 or less.

[Fourth Embodiment]

Figure 45:
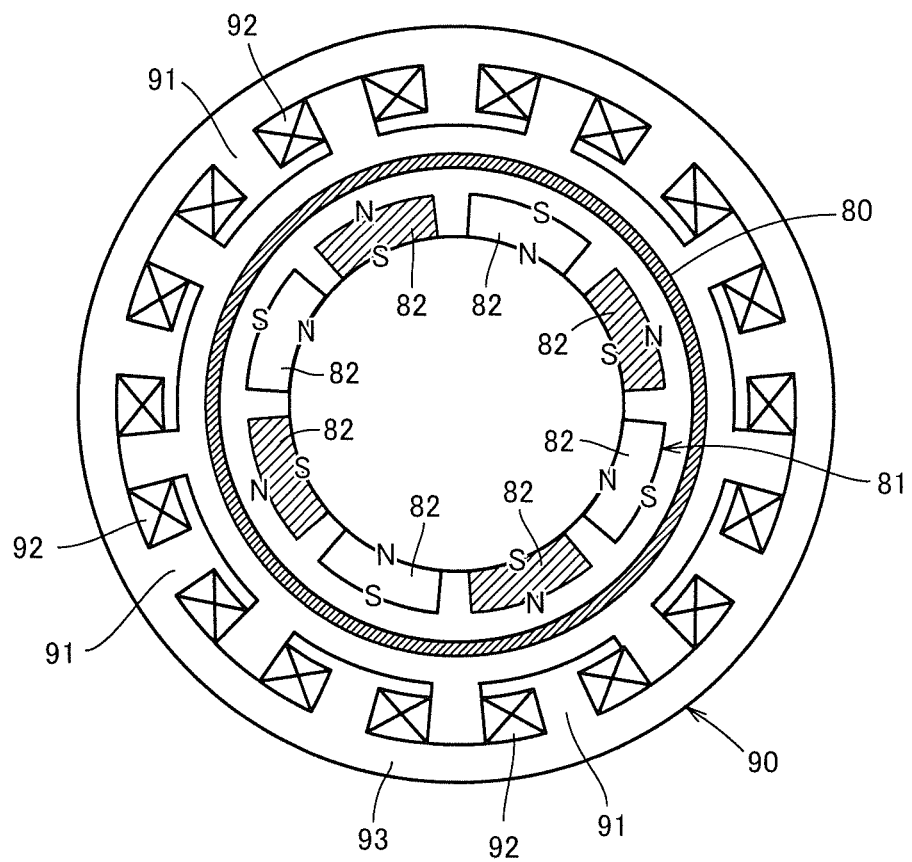
FIG. 45 shows a structure of a radial gap type motor according to a fourth embodiment of the present invention.

FIG. 45 is a plan view showing a substantial part of a radial gap type motor according to a fourth embodiment of the present invention.

In FIG. 45, this radial gap type motor has a structure similar to that of the axial gap type motor in FIG. 39, and includes first and second chambers (not shown) partitioned from each other by a cylindrical diaphragm 80. The first chamber on an inner side relative to diaphragm 80 includes a cylindrical rotor 81 rotatably provided along diaphragm 80, and the second chamber on an outer side relative to diaphragm 80 includes a stator 90 for driving rotor 81 to rotate with diaphragm 80 interposed therebetween.

Rotor 81 includes a cylindrical support member (not shown) made of a nonmagnetic material, and a plurality of (e.g., eight) permanent magnets 82 fixed to the support member. The plurality of permanent magnets 82 are aligned with a gap therebetween in a rotation direction of rotor 81. Each permanent magnet 82 is magnetized in a direction (radial direction) orthogonal to the rotation direction of rotor 81. Two adjacent permanent magnets 82 have magnetic polarities different from each other. Stator 90 includes a plurality of (e.g., six) magnetic materials 91 arranged to face the plurality of permanent magnets 82, and a plurality of coils 92 wound around the plurality of magnetic materials 91, respectively, for generating a rotating magnetic field. The plurality of magnetic materials 91 are fixed to an inner circumferential surface of a cylindrical yoke 93. Rotor 81 can be rotated by applying voltages to the plurality of coils 92 by the power distribution system shifted by 120 degrees.

Figure 46:
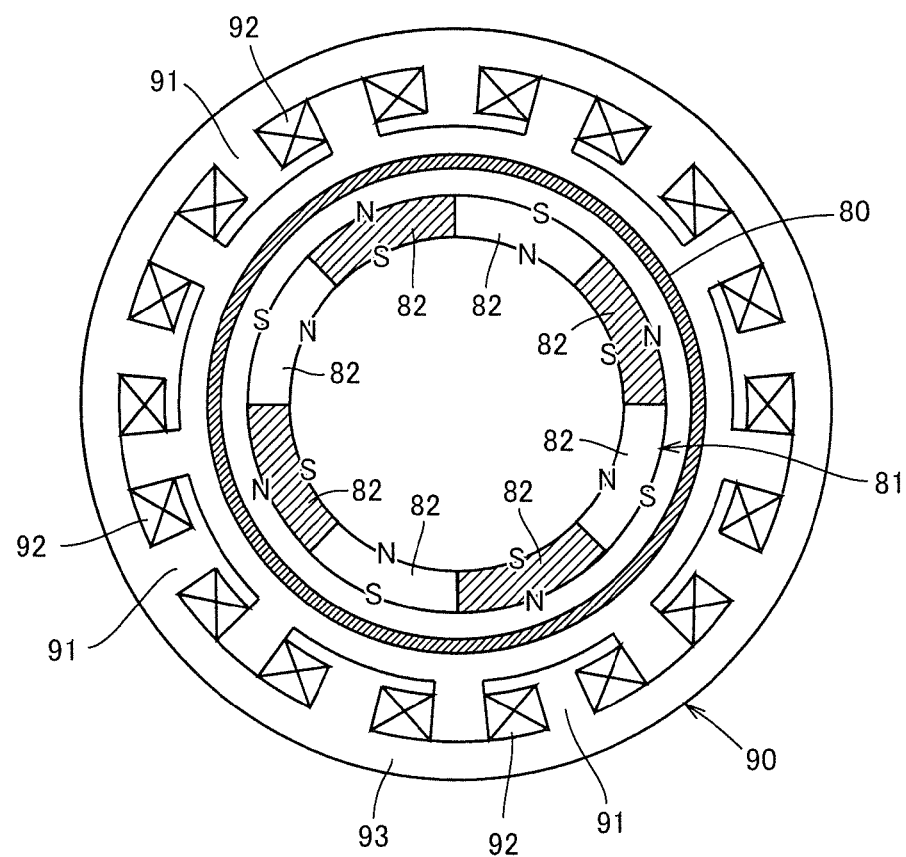
FIG. 46 shows a comparative example of the fourth embodiment.

The effect of the fourth embodiment will now be described. FIG. 46 shows a comparative example of the fourth embodiment, which is compared to FIG. 45. Referring to FIG. 46, this comparative example is different from the fourth embodiment in that there is no gap between the plurality of permanent magnets 82.

As shown in FIG. 14 (a) and (b), when permanent magnet 82 in the fourth embodiment and permanent magnet 82 in the comparative example have the same weight, magnetic flux density between permanent magnets 82 and 82 is higher in the fourth embodiment, and a magnetic field around permanent magnets 82 is stronger in the fourth embodiment. In the fourth embodiment, therefore, a magnetic coupling force between permanent magnets 82 in rotor 81 and magnetic materials 91 and coils 92 in stator 90 can be increased. Accordingly, the rotational torque of rotor 81 can be increased while maintaining small device dimensions.

Figure 47:
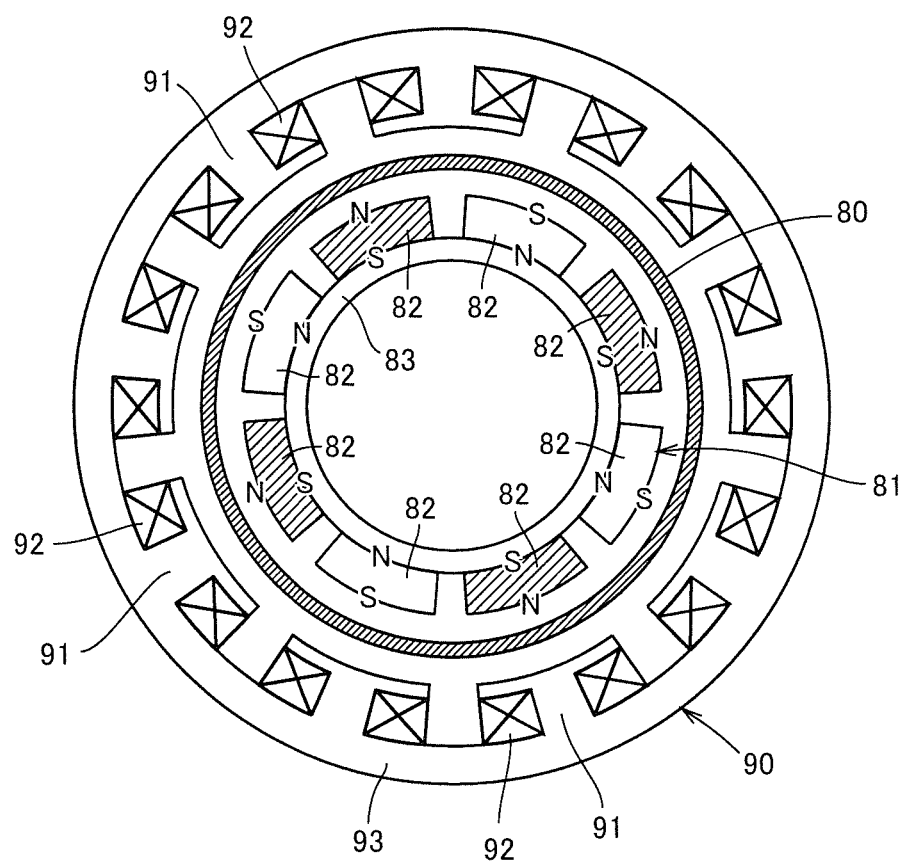
FIG. 47 shows a modification of the fourth embodiment.

Various modifications of the fourth embodiment will now be described. In a modification of FIG. 47, the plurality of permanent magnets 82 and a cylindrical magnetic material 83 are provided in rotor 81. The plurality of permanent magnets 82 are arranged with a gap therebetween at equiangular intervals along a single circle such that adjacent magnetic polarities are different from each other. Magnetic material 83 serves as a back yoke of the plurality of permanent magnets 82. In other words, permanent magnet 82 having the N-pole oriented to diaphragm 80 and permanent magnet 82 having the S-pole oriented to diaphragm 80 are alternately arranged with a gap therebetween at equiangular intervals along a single circle. A surface of permanent magnet 82 opposite to a surface closer to diaphragm 80 is attracted to an outer circumferential surface of cylindrical magnetic material 83 by a magnetic force, so that the plurality of permanent magnets 82 are magnetically coupled to magnetic material 83. Thus, a magnetic field around the surfaces of permanent magnets 82 closer to diaphragm 80 is stronger than in the fourth embodiment (see FIG. 16). Accordingly, the rotational torque of rotor 81 can be increased while maintaining small device dimensions. Further, copper loss that occurs in coils 92 can be reduced, thereby enhancing energy efficiency in driving rotor 81 to rotate.

Figure 48:
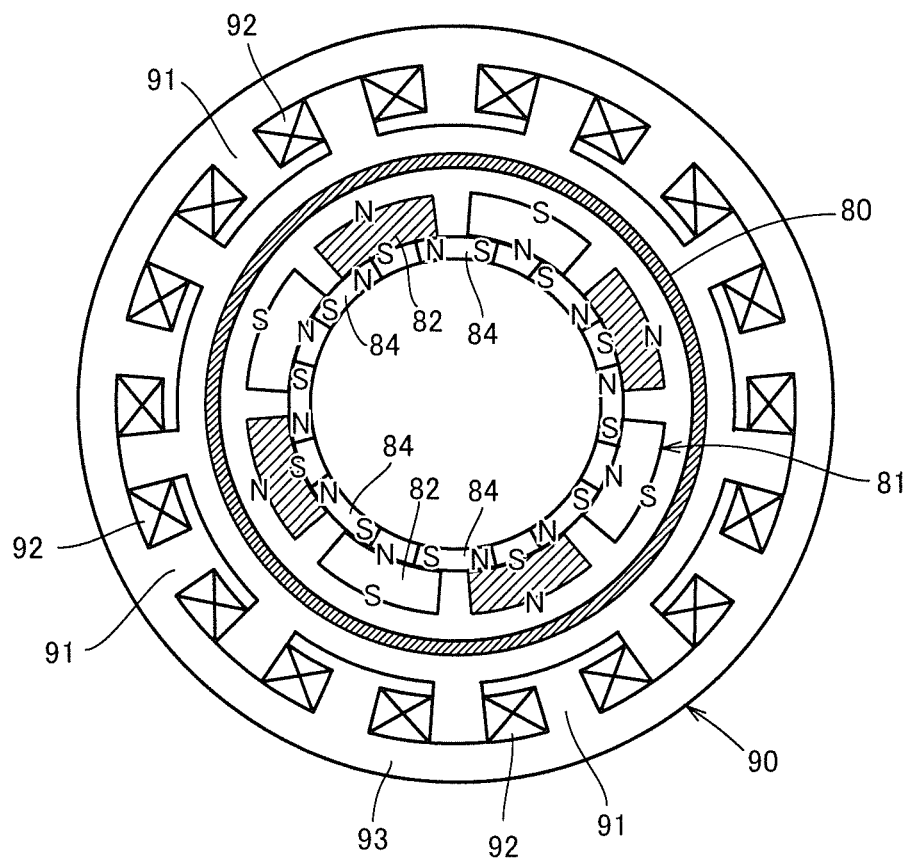
FIG. 48 shows another modification of the fourth embodiment.

In a modification of FIG. 48, the plurality of permanent magnets 82 and a plurality of permanent magnets 84 are provided in rotor 81. The number of permanent magnets 84 is equal to the number of permanent magnets 82. The plurality of permanent magnets 84 are provided on the side of the plurality of permanent magnets 82 opposite to the side closer to diaphragm 80, and are aligned in the rotation direction of rotor 81 along the plurality of permanent magnets 82. Each permanent magnet 84 is provided correspondingly to a gap between every two adjacent permanent magnets 82 to cover the corresponding gap from the side opposite to diaphragm 80, and is magnetized in the rotation direction of rotor 81. Each magnetic polarity of each permanent magnet 84 is identical to an adjacent magnetic polarity of permanent magnet 84, and is different from a corresponding magnetic polarity of permanent magnet 82. Each permanent magnet 84 is attracted to two corresponding permanent magnets 82 by a magnetic force, so that the plurality of permanent magnets 82 are magnetically coupled to the plurality of permanent magnets 84. Thus, a magnetic field around the surfaces of permanent magnets 82 closer to diaphragm 80 is stronger than in the modification of FIG. 47 (see FIG. 17). Again, in this modification, the rotational torque of rotor 81 can be increased while maintaining small device dimensions, thereby enhancing energy efficiency in driving rotor 81 to rotate.

Figure 49:
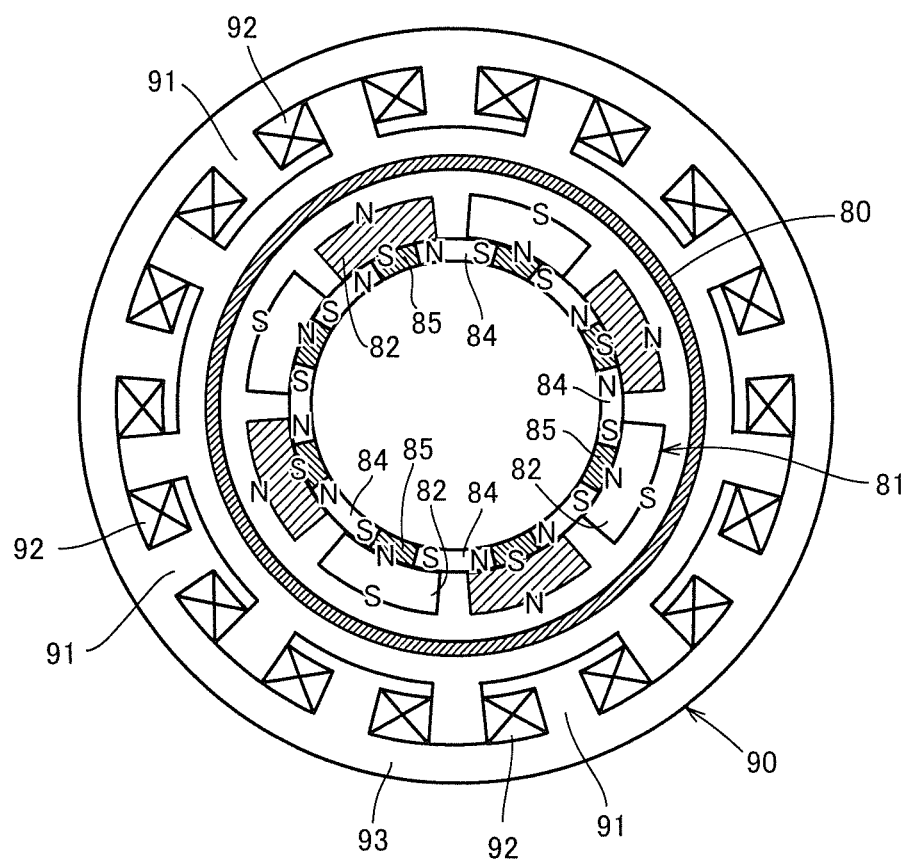
FIG. 49 shows yet another modification of the fourth embodiment.

As shown in FIG. 49, a magnetic material 85 may be inserted in a gap between every two adjacent permanent magnets 84 and each permanent magnet 82 (see FIG. 18).

Figure 50:
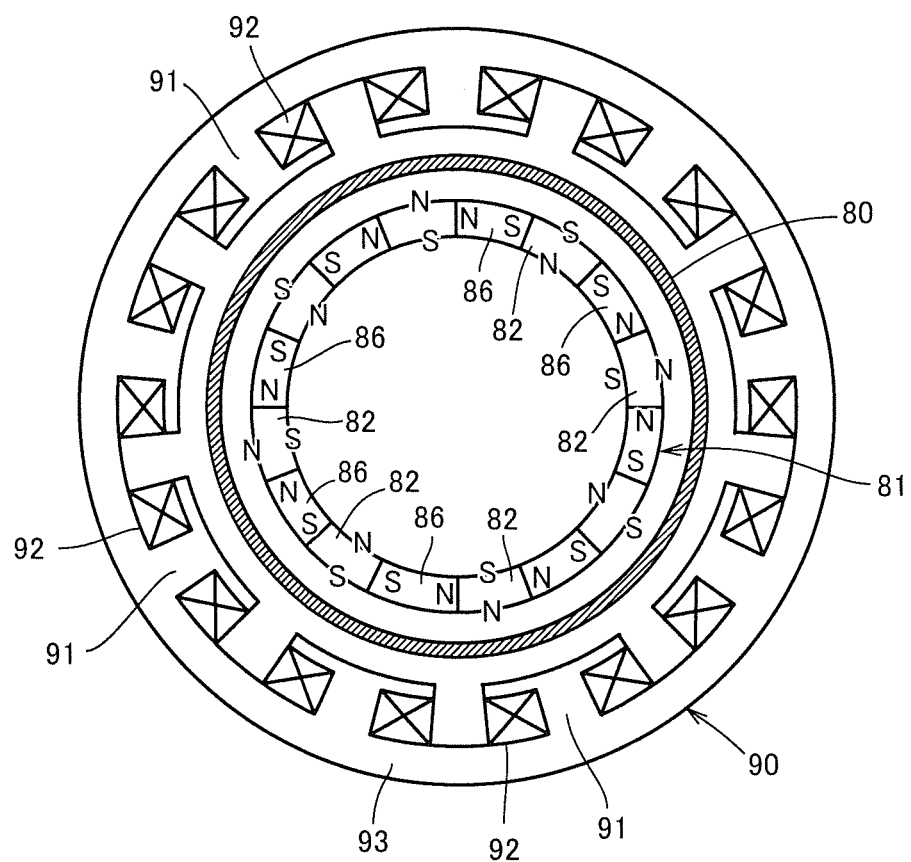
FIG. 50 shows yet another modification of the fourth embodiment.

In a modification of FIG. 50, the plurality of permanent magnets 82 and a plurality of permanent magnets 86 are provided in rotor 81. The number of permanent magnets 86 is equal to the number of permanent magnets 82. Permanent magnets 86 are magnetized in a circumferential direction (the rotation direction of rotor 81). Each of the plurality of permanent magnets 82 and each of the plurality of permanent magnets 86 are alternately arranged in the Halbach array at equiangular intervals along a single circle. In other words, permanent magnet 82 having the N-pole oriented to diaphragm 80 and permanent magnet 82 having the S-pole oriented to diaphragm 80 are alternately arranged with a gap therebetween at equiangular intervals along a single circle. The N-pole of each permanent magnet 86 is arranged toward permanent magnet 82 having the N-pole oriented to diaphragm 80, and the S-pole of each permanent magnet 86 is arranged toward permanent magnet 82 having the S-pole oriented to diaphragm 80. The plurality of permanent magnets 82 have the same shape, and the plurality of permanent magnets 86 have the same shape. Permanent magnets 82 and permanent magnets 86 may have the same shape or different shapes. In this modification, an attractive force between permanent magnets 82 and magnetic materials 91 can be suppressed and a magnetic flux that causes torque can be increased, thereby minimizing the permanent magnets (see FIG. 19). Namely, the weight of rotor 81 can be minimized, and energy efficiency can be enhanced even with a wide motor gap.

Furthermore, with a ratio between a surface area of permanent magnet 82 facing diaphragm 80 and a surface area of permanent magnet 86 facing diaphragm 80, the attractive force between permanent magnets 82 and magnetic materials 91 and the magnetic flux that causes torque can be adjusted. As shown in FIG. 20, when the area ratio of permanent magnet 86 to permanent magnet 82 is set in a range from ½ or more and 2 or less, the rotational torque of rotor 81 can be increased while suppressing the attractive force between permanent magnets 82 and magnetic materials 91 to low level. Therefore, an optimal range of the area ratio of permanent magnet 86 to permanent magnet 82 is between ½ or more and 2 or less.

It should be understood that the embodiments disclosed herein are illustrative and non-restrictive in every respect. The scope of the present invention is defined by the terms of the claims, rather than the description above, and is intended to include any modifications within the scope and meaning equivalent to the terms of the claims.

REFERENCE SIGNS LIST 1, 41 pump unit; 2 housing; 3 body portion; 4 blood inlet port; 5 blood outlet port; 6, 60, 80 diaphragm; 7 blood chamber; 8 motor chamber; 10 impeller; 10a through hole; 11, 12 shroud; 13 vane; 14 blood passage; 15 to 17, 29, 31, 63, 65, 67, 82, 84, 86 permanent magnet; 18, 28, 30, 35, 37 to 39, 64, 66, 71, 83, 85, 91 magnetic material; 19, 36, 73, 93 yoke; 20, 72, 92 coil; 21, 22 groove for hydrodynamic bearing; 25, 42 controller; 26, 43 motor control circuit; 27, 32, 33, 44 to 46 power amplifier; 32, 47 switch; 48 comparator; 49 position operation unit; 50 rotation speed operation unit; 51 position determination unit; S magnetic sensor.

The invention claimed is:

1. A rotation drive device including a housing having first and second chambers partitioned from each other by a diaphragm, a rotor rotatably provided in said first chamber along said diaphragm, and a drive unit provided in said second chamber for driving said rotor to rotate with said diaphragm interposed therebetween, said rotor comprising a plurality of first permanent magnets, the first permanent magnets having an angular spacing between each magnet,
   each of said first permanent magnets being magnetized in a direction orthogonal to said rotation direction of said rotor,
   every two adjacent ones of the first permanent magnets having magnetic polarities different from each other, said drive unit including:
   a plurality of first magnetic materials arranged to face said plurality of first permanent magnets,
   a plurality of coils wound around said plurality of first magnetic materials, respectively, for generating a rotating magnetic field;
   wherein a plurality of second permanent magnets is provided in said rotor and magnetically coupled to said plurality of first permanent magnets, wherein each of said second permanent magnets is provided correspondingly to a gap between every two adjacent ones of the first permanent magnets, and is magnetized in said rotation direction of said rotor,
   wherein each of said second permanent magnets is inserted in a corresponding gap, each of said second permanent magnets has a first magnetic polarity oriented to one of the two adjacent first permanent magnets having the first magnetic polarity oriented to the diaphragm, and each of said second permanent magnets has a second magnetic polarity oriented to the other of the two adjacent first permanent magnets having the second magnetic polarity oriented to the diaphragm; and
   wherein a ratio of a surface area of each of said second permanent magnets facing said diaphragm to a surface area of each of said first permanent magnets facing said diaphragm is set to be ½ or more and 2 or less.

2. The rotation drive device according to claim 1, further comprising a second magnetic material provided in said rotor, arranged on a side of said plurality of first permanent magnets opposite to a side closer to said diaphragm, and magnetically coupled to said plurality of first permanent magnets.

3. The rotation drive device according to claim 1, wherein each of said second permanent magnets is arranged to cover a corresponding gap from a side opposite to said diaphragm, and each magnetic polarity of each of said second permanent magnets is identical to an adjacent magnetic polarity of the second permanent magnet, and is different from a corresponding magnetic polarity of the first permanent magnet.

4. The rotation drive device according to claim 3, further comprising a plurality of second magnetic materials provided in said rotor and inserted in the plurality of gaps between said plurality of second permanent magnets, respectively.

5. The rotation drive device according to claim 1, wherein said diaphragm is formed in a cylindrical shape, and said rotor and said drive unit are arranged with a gap therebetween in a radial direction of said rotor.

6. The rotation drive device according to claim 1, wherein said diaphragm is formed in a plane shape, and said rotor and said drive unit are arranged with a gap therebetween in a direction in which a rotation central axis of said rotor extends.

7. A centrifugal pump apparatus comprising the rotation drive device according to claim 6, wherein said rotor is an impeller for delivering liquid by a centrifugal force during rotation.

8. The centrifugal pump apparatus according to claim 7, wherein said liquid is blood, and said centrifugal pump apparatus is used for circulating said blood.

9. A centrifugal pump apparatus including a housing having first and second chambers partitioned from each other by a diaphragm, an impeller rotatably provided in said first chamber along said diaphragm for delivering liquid by a centrifugal force during rotation, and a drive unit provided in said second chamber for driving said impeller to rotate with said diaphragm interposed therebetween, said centrifugal pump apparatus comprising:
   a first magnetic material provided in one surface of said impeller;
   a second magnetic material provided in an inner wall of said first chamber facing the one surface of said impeller, for attracting said first magnetic material; and
   a plurality of first permanent magnets provided in the other surface of said impeller, the first permanent magnets having an angular spacing between each magnet,
   each of said first permanent magnets being magnetized in a direction in which a rotation central axis of said impeller extends,
   every two adjacent ones of the first permanent magnets having magnetic polarities different from each other,
   a plurality of second permanent magnets magnetically coupled to said plurality of first permanent magnets, wherein each of said second permanent magnets is provided correspondingly to a gap between every two adjacent ones of the first permanent magnets, and is magnetized in a rotation direction of said impeller,
   wherein each of said second permanent magnets is inserted in a corresponding gap, each of said second permanent magnets has a first magnetic polarity oriented to one of the two adjacent first permanent magnets having the first magnetic polarity oriented to the diaphragm, and each of said second permanent magnets has a second magnetic polarity oriented to the other of the two adjacent first permanent magnets having the second magnetic polarity oriented to the diaphragm,
   wherein a ratio of a surface area of each of said second permanent magnets facing said diaphragm to a surface area of each of said first permanent magnets facing said diaphragm is set to be ½ or more and 2 or less,
   said drive unit including
   a plurality of third magnetic materials arranged to face said plurality of first permanent magnets, and
   a plurality of coils provided correspondingly to said plurality of third magnetic materials and wound around corresponding ones of the third magnetic materials, respectively, for generating a rotating magnetic field,
   during rotation of said impeller, a first attractive force between said first and second magnetic materials and a second attractive force between said plurality of first permanent magnets and said plurality of third magnetic materials being balanced with each other substantially in a center of a movable range of said impeller in said first chamber, and
   first grooves for hydrodynamic bearing being formed in the one surface of said impeller or in the inner wall of said first chamber facing the one surface, and second grooves for hydrodynamic bearing being formed in the other surface of said impeller or in said diaphragm facing the other surface.

10. The centrifugal pump apparatus according to claim 9, wherein said liquid is blood, and said centrifugal pump apparatus is used for circulating said blood.

* * * * *